United States Patent
Barnvos et al.

(10) Patent No.: US 9,661,830 B2
(45) Date of Patent: May 30, 2017

(54) APPETIZING AND DENTALLY EFFICACIOUS ANIMAL CHEWS

(71) Applicants: Donald R. Barnvos, Huntington Beach, CA (US); John F. Berry, Simi Valley, CA (US); Melinda S. Cope, Stevenson Ranch, CA (US); Mark Donatucci, Manhattan Beach, CA (US); Davor Juravic, San Pedro, CA (US); Oscar Ortiz, Hawthorne, CA (US); Sergio Alberto Jimenez-Marquez, El Segundo, CA (US)

(72) Inventors: Donald R. Barnvos, Huntington Beach, CA (US); John F. Berry, Simi Valley, CA (US); Melinda S. Cope, Stevenson Ranch, CA (US); Mark Donatucci, Manhattan Beach, CA (US); Davor Juravic, San Pedro, CA (US); Oscar Ortiz, Hawthorne, CA (US); Sergio Alberto Jimenez-Marquez, El Segundo, CA (US)

(73) Assignee: Big Heart Pet, Inc., Orrville, OH (US)

( * ) Notice: Subject to any disclaimer, the term of this patent is extended or adjusted under 35 U.S.C. 154(b) by 681 days.

(21) Appl. No.: 13/833,424

(22) Filed: Mar. 15, 2013

(65) Prior Publication Data

US 2013/0273125 A1     Oct. 17, 2013

Related U.S. Application Data

(60) Provisional application No. 61/625,598, filed on Apr. 17, 2012.

(51) Int. Cl.
*A61K 9/00*     (2006.01)
*A01K 29/00*    (2006.01)
(Continued)

(52) U.S. Cl.
CPC ............ *A01K 29/00* (2013.01); *A01K 15/026* (2013.01); *A23K 10/26* (2016.05); *A23K 10/30* (2016.05);
(Continued)

(58) Field of Classification Search
CPC .................................................. A61K 9/0056
See application file for complete search history.

(56) References Cited

U.S. PATENT DOCUMENTS

| 3,184,381 A | 5/1965 | Ashmead et al. |
| 3,325,289 A | 6/1967 | Lyons |

(Continued)

FOREIGN PATENT DOCUMENTS

| CN | 2739960 | 11/2005 |
| CN | 301125470D | 2/2010 |

(Continued)

OTHER PUBLICATIONS

Extended Search Report dated Aug. 3, 2016 in corresponding European Patent Application No. 16167549.

(Continued)

*Primary Examiner* — Benjamin Packard
(74) *Attorney, Agent, or Firm* — Michael A. Olshavsky

(57) ABSTRACT

Described herein are chewable articles intended to be provided to animals for purposes including dental cleaning, breath freshening, nutrition, administration to the animal of beneficial agents, satisfaction of the animal's urge to chew, and general enjoyment by the animal. The chews are made to be appetizing to the animal, to satisfy an urge to chew, to effect abrasive cleaning of the animal's teeth, to deliver one or more active agents to the oral cavity of the animal, or a combination of these. The chews have a resilient, chewable texture and are shaped to facilitate dental cleaning, to facilitate oral grasping by the animal, to appeal to human (Continued)

owners of the animal, to enhance the human-animal bond, or a combination of these. Also disclosed are apparatus and methods for making such chewable articles and for formulating and using them to effect dental health in animals.

36 Claims, 31 Drawing Sheets
(8 of 31 Drawing Sheet(s) Filed in Color)

(51) Int. Cl.

| | |
|---|---|
| A61K 8/02 | (2006.01) |
| A61Q 11/00 | (2006.01) |
| A01K 15/02 | (2006.01) |
| A61K 8/64 | (2006.01) |
| A61K 8/73 | (2006.01) |
| A23N 17/00 | (2006.01) |
| A23K 40/20 | (2016.01) |
| A23K 10/26 | (2016.01) |
| A23K 10/30 | (2016.01) |
| A23K 20/174 | (2016.01) |
| A23K 20/179 | (2016.01) |
| A23K 20/147 | (2016.01) |
| A23K 20/163 | (2016.01) |
| A23K 20/10 | (2016.01) |
| A23K 20/20 | (2016.01) |
| A23K 20/26 | (2016.01) |
| A23K 50/42 | (2016.01) |

(52) U.S. Cl.
CPC ............ *A23K 20/10* (2016.05); *A23K 20/147* (2016.05); *A23K 20/163* (2016.05); *A23K 20/174* (2016.05); *A23K 20/179* (2016.05); *A23K 20/20* (2016.05); *A23K 20/26* (2016.05); *A23K 40/20* (2016.05); *A23K 50/42* (2016.05); *A23N 17/005* (2013.01); *A61K 8/02* (2013.01); *A61K 8/645* (2013.01); *A61K 8/732* (2013.01); *A61K 9/0056* (2013.01); *A61Q 11/00* (2013.01)

(56) References Cited

U.S. PATENT DOCUMENTS

| | | | |
|---|---|---|---|
| 4,006,266 | A | 2/1977 | Bone et al. |
| 4,039,689 | A | 8/1977 | Bone |
| 4,041,181 | A | 8/1977 | Burrows et al. |
| 4,044,158 | A | 8/1977 | Burkwall, Jr. |
| 4,076,846 | A † | 2/1978 | Nakatsuka |
| 4,143,171 | A | 3/1979 | Buckley et al. |
| 4,233,290 | A | 11/1980 | Ferrari et al. |
| 4,284,652 | A | 8/1981 | Christensen |
| 4,330,562 | A | 5/1982 | Nassar |
| 4,384,009 | A | 5/1983 | Lewis et al. |
| 4,454,163 | A | 6/1984 | Gellman et al. |
| 4,777,058 | A | 10/1988 | Chandler et al. |
| 4,842,885 | A | 6/1989 | Hamilton et al. |
| 4,889,712 | A | 12/1989 | Gaffar et al. |
| 4,904,494 | A | 2/1990 | Spanier |
| 4,910,038 | A | 3/1990 | Ducharme |
| 4,960,043 | A | 10/1990 | vanLengerich |
| 4,989,604 | A | 2/1991 | Fang |
| 5,092,272 | A | 3/1992 | O'Rourke |
| 5,155,946 | A | 10/1992 | Domann |
| 5,174,243 | A | 12/1992 | O'Rourke |
| 5,215,038 | A | 6/1993 | O'Rourke |
| RE34,352 | E | 8/1993 | Markham et al. |
| 5,262,190 | A | 11/1993 | Cunningham et al. |
| 5,263,436 | A | 11/1993 | Axelrod |
| D343,262 | S | 1/1994 | Axelrod |
| 5,296,209 | A | 3/1994 | Simone |
| 5,296,217 | A | 3/1994 | Stookey |
| 5,358,727 | A | 10/1994 | Yates et al. |
| 5,407,661 | A | 4/1995 | Simone et al. |
| 5,431,927 | A | 7/1995 | Hand et al. |
| 5,460,802 | A | 10/1995 | Asami et al. |
| 5,500,239 | A | 3/1996 | Hayward |
| 5,532,010 | A | 7/1996 | Spanier et al. |
| 5,565,234 | A | 10/1996 | Teraguchi et al. |
| D376,449 | S | 12/1996 | Axelrod |
| 5,618,518 | A | 4/1997 | Stookey |
| 5,647,302 | A | 7/1997 | Shipp |
| 5,857,431 | A | 1/1999 | Peterson |
| 5,865,146 | A | 2/1999 | Markham |
| 5,922,379 | A | 7/1999 | Wang |
| 5,967,154 | A | 10/1999 | Anderson |
| 5,989,604 | A | 11/1999 | Wolf et al. |
| 5,997,934 | A | 12/1999 | Geromini et al. |
| D418,639 | S | 1/2000 | Simon |
| 6,044,800 | A | 4/2000 | Kubo et al. |
| 6,050,224 | A | 4/2000 | Owens |
| 6,054,166 | A | 4/2000 | Dupart |
| 6,080,419 | A | 6/2000 | Stookey |
| 6,116,191 | A | 9/2000 | Suchowski et al. |
| 6,117,477 | A | 9/2000 | Paluch et al. |
| 6,136,679 | A | 10/2000 | Yu et al. |
| 6,148,771 | A | 11/2000 | Costello |
| 6,156,355 | A | 12/2000 | Shields, Jr. et al. |
| 6,178,922 | B1 | 1/2001 | Denesuk et al. |
| 6,223,693 | B1 | 5/2001 | Perlberg et al. |
| 6,228,402 | B1 | 5/2001 | Wolf et al. |
| 6,261,591 | B1 | 7/2001 | Kealy |
| 6,261,620 | B1 | 7/2001 | Leadbeater |
| 6,277,420 | B1 | 8/2001 | Andersen et al. |
| D450,894 | S | 11/2001 | Suchowski et al. |
| 6,312,746 | B2 | 11/2001 | Paluch |
| D451,651 | S | 12/2001 | Kaplan |
| D453,242 | S | 1/2002 | Kaplan |
| 6,349,166 | B1 | 2/2002 | Kaliszek et al. |
| 6,355,229 | B1 | 3/2002 | Adamy |
| 6,379,725 | B1 | 4/2002 | Wang et al. |
| 6,387,381 | B2 | 5/2002 | Christensen |
| 6,405,681 | B1 | 6/2002 | Ward |
| 6,431,996 | B1 | 8/2002 | Wright et al. |
| 6,455,083 | B1 | 9/2002 | Wang |
| 6,495,176 | B1 | 12/2002 | McGenity et al. |
| D475,816 | S | 6/2003 | Adamson |
| 6,576,246 | B1 | 6/2003 | Denesuk |
| 6,584,938 | B2 | 7/2003 | Sherrill et al. |
| 6,586,027 | B2 | 7/2003 | Axelrod |
| 6,586,031 | B1 | 7/2003 | Kelly |
| 6,601,539 | B1 | 8/2003 | Snook |
| 6,610,276 | B2 | 8/2003 | Melman |
| 6,620,353 | B2 | 9/2003 | Abrams |
| 6,652,279 | B2 | 11/2003 | Santacruz |
| 6,652,892 | B2 | 11/2003 | McGenity et al. |
| 6,672,252 | B2 | 1/2004 | Levin |
| 6,685,916 | B1 | 2/2004 | Holme et al. |
| 6,723,358 | B1 | 4/2004 | vanLengerich |
| 6,739,287 | B1 | 5/2004 | Sarantis |
| 6,776,123 | B2 | 8/2004 | Homan et al. |
| D496,773 | S | 10/2004 | Tepper et al. |
| 6,811,802 | B2 | 11/2004 | Van Esbroeck |
| 6,815,000 | B2 | 11/2004 | Kesler |
| 6,841,178 | B2 | 1/2005 | Cupp et al. |
| 6,896,924 | B2 | 5/2005 | Hernandez et al. |
| 6,904,870 | B2 | 6/2005 | Russell-Maynard |
| 6,916,497 | B2 | 7/2005 | Axelrod |
| 6,935,275 | B2 | 8/2005 | Jia et al. |
| D511,030 | S | 10/2005 | Byrne |
| 6,972,133 | B1 | 12/2005 | Denesuk |
| D515,275 | S | 2/2006 | Leiweke et al. |
| 7,017,523 | B2 | 3/2006 | Handelsman |
| 7,025,020 | B2 | 4/2006 | Brown |
| 7,063,044 | B2 | 6/2006 | Handelsman et al. |
| 7,067,150 | B2 | 6/2006 | Farber et al. |
| 7,074,446 | B2 | 7/2006 | Heywood et al. |
| 7,087,260 | B2 | 8/2006 | Axelrod |
| D529,667 | S | 10/2006 | Axelrod |
| 7,125,574 | B2 | 10/2006 | Cupp et al. |
| D534,694 | S | 1/2007 | Pozzoni |

(56) References Cited

U.S. PATENT DOCUMENTS

| | | |
|---|---|---|
| D534,706 S | 1/2007 | Cuadrado |
| 7,250,186 B2 | 7/2007 | Pfaller et al. |
| 7,282,235 B2 | 10/2007 | Lombard et al. |
| 7,288,275 B2 | 10/2007 | Axelrod |
| 7,332,188 B2 | 2/2008 | Axelrod |
| 7,390,520 B2 | 6/2008 | Dempsey et al. |
| D578,726 S | 10/2008 | Edwards |
| 7,449,204 B2 * | 11/2008 | Stookey .............. A01K 15/026 426/132 |
| D586,976 S | 2/2009 | Lundwall |
| 7,490,579 B2 | 2/2009 | Axelrod |
| 7,497,189 B2 | 3/2009 | Torney et al. |
| 7,592,031 B2 | 9/2009 | Cupp et al. |
| 7,662,414 B1 † | 2/2010 | Lawlor |
| 7,678,406 B2 | 3/2010 | Heydtmann et al. |
| 7,691,424 B2 | 4/2010 | Axelrod |
| 7,691,426 B2 | 4/2010 | Axelrod et al. |
| 7,722,911 B2 | 5/2010 | Liu |
| 7,810,455 B2 | 10/2010 | Axelrod et al. |
| 7,846,482 B2 | 12/2010 | Cupp et al. |
| 7,879,377 B2 | 2/2011 | Dahl et al. |
| 7,914,835 B2 | 3/2011 | Keehn et al. |
| D636,948 S | 4/2011 | Axelrod et al. |
| 7,930,996 B2 | 4/2011 | Axelrod et al. |
| 8,057,838 B2 | 11/2011 | Levin |
| D655,056 S | 2/2012 | Blair |
| 8,119,169 B2 | 2/2012 | Worrell et al. |
| 8,137,731 B2 | 3/2012 | Pater |
| 8,158,179 B2 | 4/2012 | Bouvier et al. |
| D658,823 S | 5/2012 | Viola |
| D658,824 S | 5/2012 | Viola |
| D658,847 S | 5/2012 | Wylie |
| 8,168,161 B2 | 5/2012 | Scherl |
| 8,227,007 B2 | 7/2012 | Gajria |
| 8,231,920 B2 | 7/2012 | Axelrod |
| 8,367,144 B2 | 2/2013 | Pater |
| 8,394,438 B2 | 3/2013 | Gajria |
| 8,455,005 B2 | 6/2013 | Cupp et al. |
| 8,697,174 B2 | 4/2014 | Teconchuk et al. |
| 2001/0027755 A1 | 10/2001 | Denesuk et al. |
| 2002/0102338 A1 | 8/2002 | Knudsen |
| 2003/0168020 A1 † | 9/2003 | Levin |
| 2003/0175387 A1 | 9/2003 | English |
| 2004/0005392 A1 | 1/2004 | Filipi et al. |
| 2004/0043131 A1 | 3/2004 | Fumita |
| 2004/0086616 A1 | 5/2004 | Nie |
| 2004/0126462 A1 | 7/2004 | Tepper et al. |
| 2004/0142081 A1 | 7/2004 | Durand et al. |
| 2004/0197455 A1 | 10/2004 | Nie |
| 2004/0234654 A1 | 11/2004 | Levin |
| 2004/0241293 A1 | 12/2004 | Isern et al. |
| 2005/0003050 A1 | 1/2005 | Agnew |
| 2005/0074541 A1 | 4/2005 | Tsengas |
| 2005/0084563 A1 | 4/2005 | Cupp |
| 2005/0123585 A1 | 6/2005 | Cox et al. |
| 2005/0139167 A1 | 6/2005 | Leo |
| 2005/0214349 A1 | 9/2005 | Nie et al. |
| 2005/0233038 A1 | 10/2005 | Weinberg |
| 2006/0102099 A1 | 5/2006 | Edwards |
| 2006/0105025 A1 | 5/2006 | Hill et al. |
| 2006/0105098 A1 | 5/2006 | Merrick |
| 2006/0118611 A1 | 6/2006 | Michelsen et al. |
| 2006/0141105 A1 | 6/2006 | Derriey et al. |
| 2006/0150919 A1 * | 7/2006 | Thomason .......... A01K 15/026 119/710 |
| 2006/0165854 A1 † | 7/2006 | Levin |
| 2006/0188611 A1 † | 8/2006 | Unlu |
| 2006/0188632 A1 | 8/2006 | Nie et al. |
| 2006/0193959 A1 † | 8/2006 | Nie |
| 2006/0204623 A1 | 9/2006 | Levin |
| 2006/0292288 A1 | 12/2006 | Maynard |
| 2007/0015100 A1 | 1/2007 | Morris |
| 2007/0031555 A1 | 2/2007 | Axelrod et al. |
| 2007/0101946 A1 | 5/2007 | Penny |
| 2007/0148104 A1 | 6/2007 | Goettert et al. |
| 2007/0148282 A1 | 6/2007 | Zubair et al. |
| 2007/0224131 A1 | 9/2007 | McCollum et al. |
| 2007/0234965 A1 | 10/2007 | Aguilar et al. |
| 2007/0237806 A1 | 10/2007 | Melman |
| 2007/0254077 A1 | 11/2007 | Germano et al. |
| 2007/0269572 A1 | 11/2007 | Turner |
| 2008/0003270 A1 | 1/2008 | Martinez et al. |
| 2008/0035071 A1 | 2/2008 | Veloce |
| 2008/0063775 A1 † | 3/2008 | Liu |
| 2008/0069862 A1 | 3/2008 | Hurwitz |
| 2008/0160067 A1 | 7/2008 | Boeckh |
| 2008/0160157 A1 | 7/2008 | Rutishauser et al. |
| 2008/0187642 A1 | 8/2008 | Ekanayake et al. |
| 2008/0254168 A1 | 10/2008 | Mueller et al. |
| 2008/0299286 A1 | 12/2008 | Josephson et al. |
| 2008/0314333 A1 | 12/2008 | Hurwitz |
| 2009/0078214 A1 | 3/2009 | Mann |
| 2009/0110778 A1 | 4/2009 | Muscroft et al. |
| 2009/0202700 A1 | 8/2009 | Bunke et al. |
| 2009/0311390 A1 | 12/2009 | Phelps et al. |
| 2010/0003393 A1 | 1/2010 | Torney |
| 2010/0136162 A1 | 6/2010 | Cupp |
| 2010/0136201 A1 | 6/2010 | Bigeard et al. |
| 2010/0183523 A1 | 7/2010 | Wagner |
| 2010/0224138 A1 | 9/2010 | Axelrod et al. |
| 2010/0303968 A1 | 12/2010 | Sunvold et al. |
| 2010/0310750 A1 | 12/2010 | She et al. |
| 2010/0311874 A1 | 12/2010 | Mentink et al. |
| 2011/0011351 A1 | 1/2011 | Simoni |
| 2011/0052661 A1 | 3/2011 | Weiss |
| 2011/0076366 A1 | 3/2011 | Pater |
| 2011/0081453 A1 | 4/2011 | Axelrod |
| 2011/0086130 A1 | 4/2011 | Axelrod |
| 2011/0139087 A1 | 6/2011 | Lang et al. |
| 2011/0217422 A1 | 9/2011 | Suttle et al. |
| 2011/0229609 A1 | 9/2011 | Lin |
| 2011/0290197 A1 | 12/2011 | Koo |
| 2011/0300197 A1 | 12/2011 | McGenity et al. |
| 2012/0021104 A1 | 1/2012 | Van Esbroeck |
| 2012/0045560 A1 | 2/2012 | Axelrod |
| 2012/0058227 A1 | 3/2012 | Keehn et al. |
| 2012/0111284 A1 | 5/2012 | Berger |
| 2012/0157416 A1 | 6/2012 | Kumiega et al. |
| 2012/0201914 A1 | 8/2012 | Huang et al. |
| 2012/0213889 A1 | 8/2012 | Chiang |
| 2012/0234259 A1 | 9/2012 | Xu |
| 2012/0237641 A1 | 9/2012 | Jia et al. |
| 2012/0279460 A1 | 11/2012 | Pang et al. |
| 2013/0101648 A1 | 4/2013 | Axelrod et al. |
| 2013/0104810 A1 | 5/2013 | Haakansson et al. |
| 2013/0108561 A1 | 5/2013 | Axelrod et al. |
| 2013/0122168 A1 | 5/2013 | Van Esbroeck |
| 2013/0251872 A1 | 9/2013 | Axelrod |
| 2013/0273225 A1 | 10/2013 | Moulton |
| 2013/0287930 A1 | 10/2013 | Bramoulle et al. |

FOREIGN PATENT DOCUMENTS

| | | |
|---|---|---|
| CN | 301136481D | 2/2010 |
| CN | 301358063 | 10/2010 |
| EP | 1800545 | 6/2007 |
| GB | 2413503 | 2/2005 |
| WO | WO 02/49657 A1 | 6/2002 |
| WO | WO02078462 A1 | 10/2002 |
| WO | WO2012/052425 | 4/2012 |

OTHER PUBLICATIONS

Partial Supplementary Search Report dated Jan. 15, 2016 in corresponding European Patent Application No. 13777648.
Final Office Action dated Dec. 1, 2016 in corresponding U.S. Appl. No. 14/657,566.

\* cited by examiner
† cited by third party

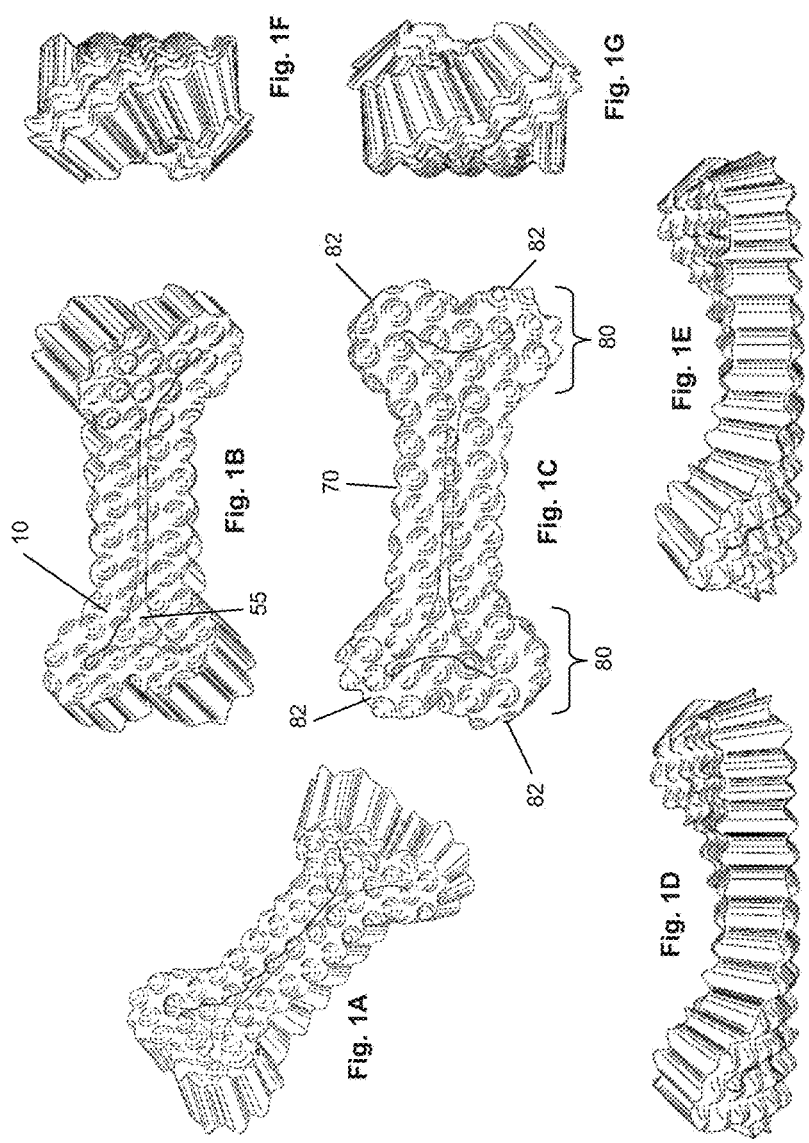

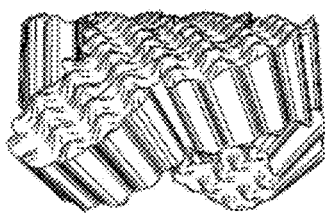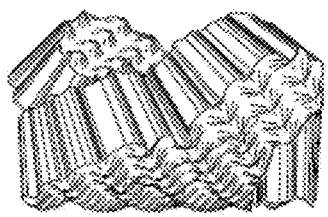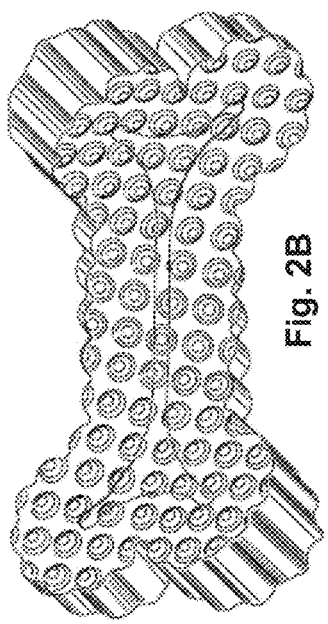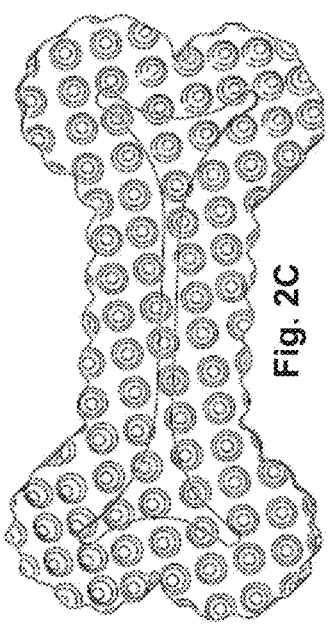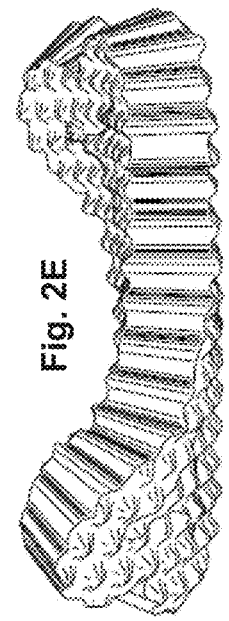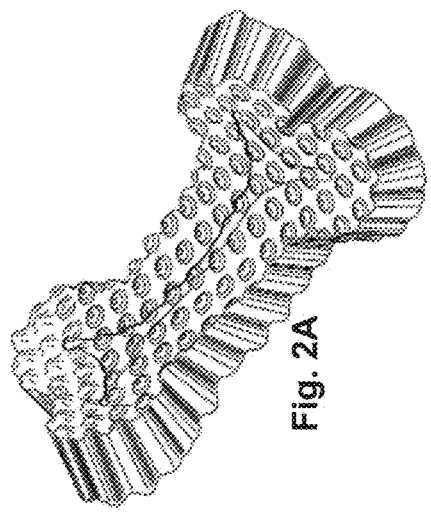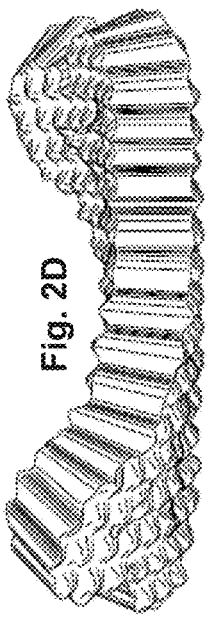

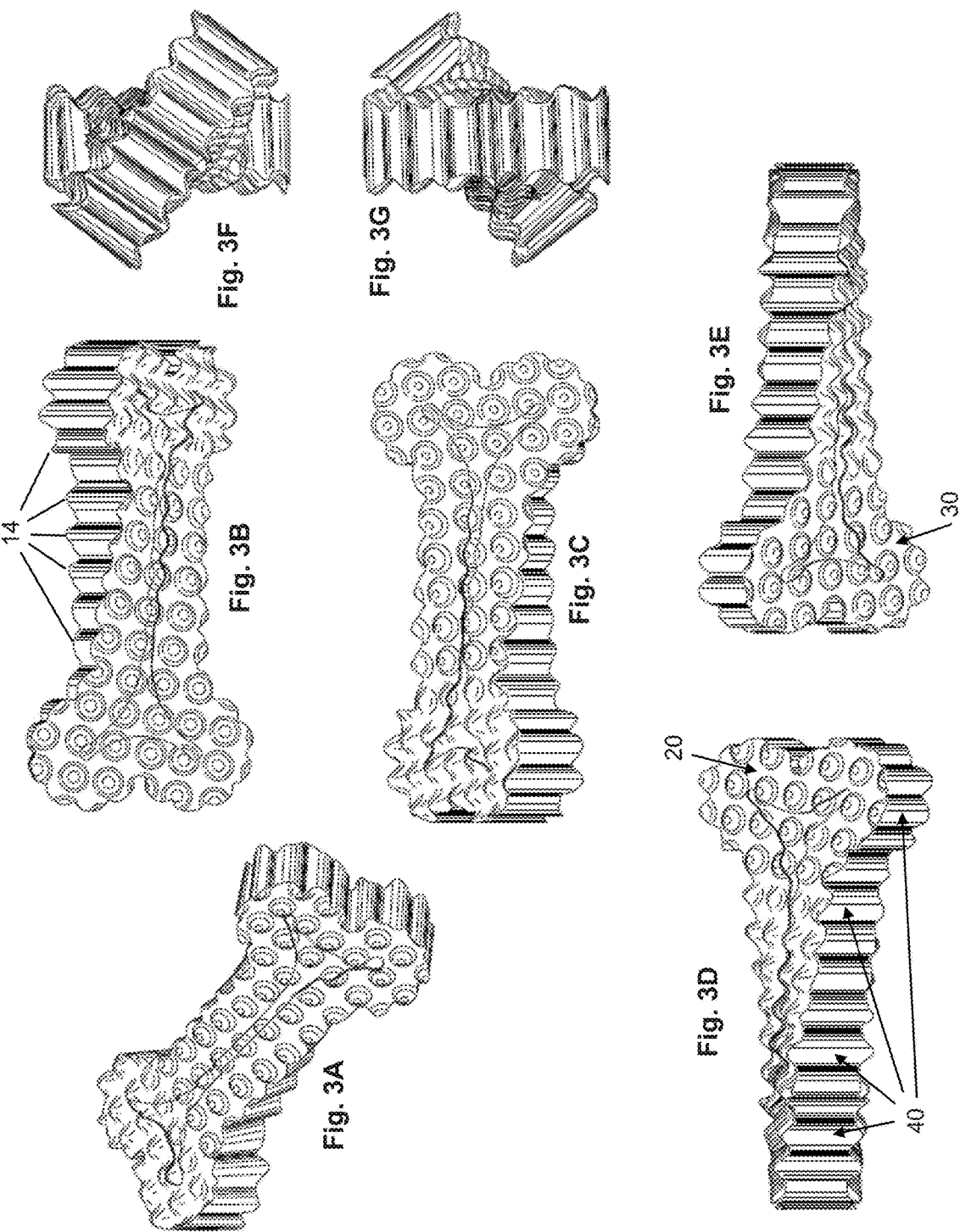

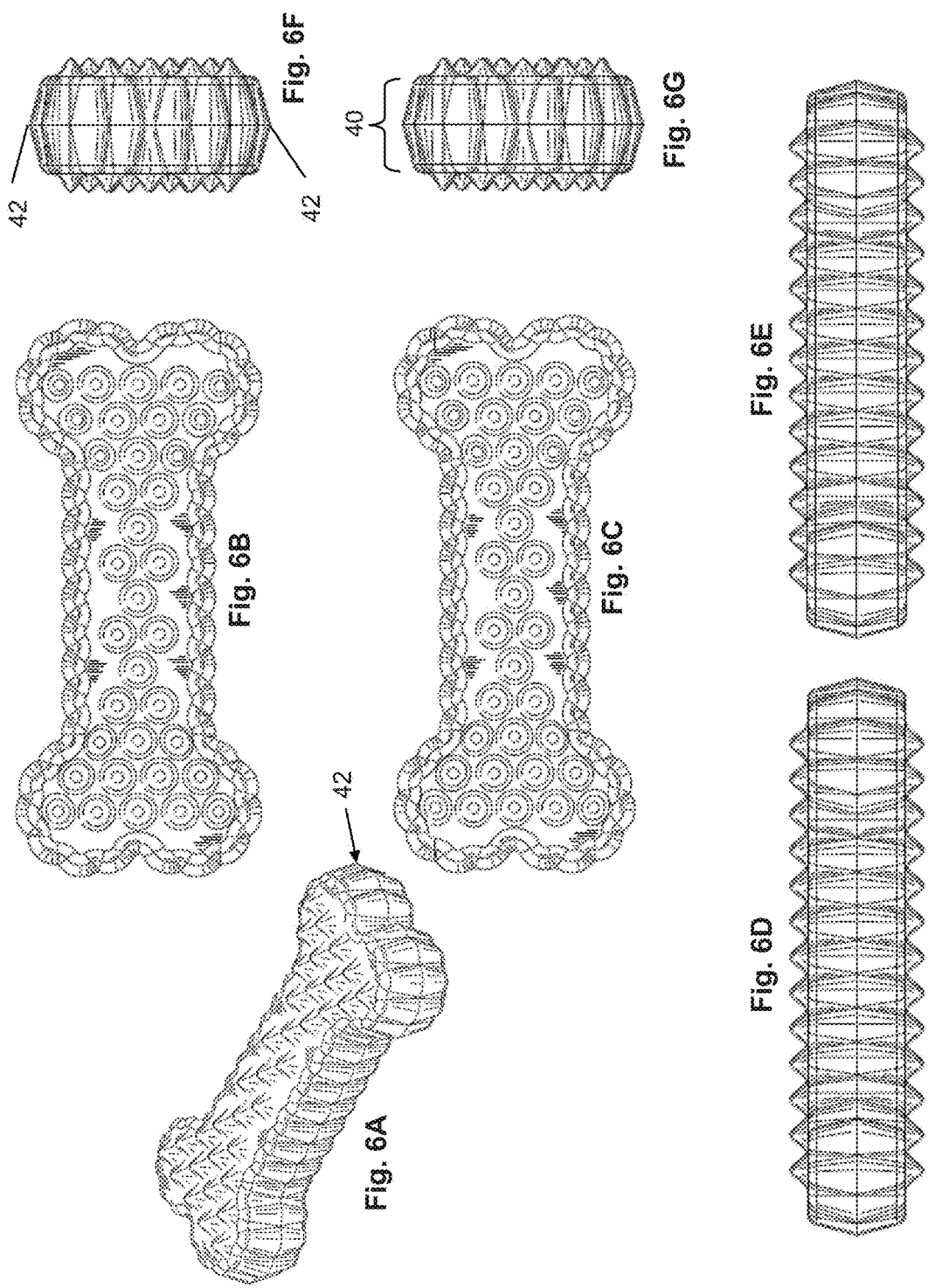

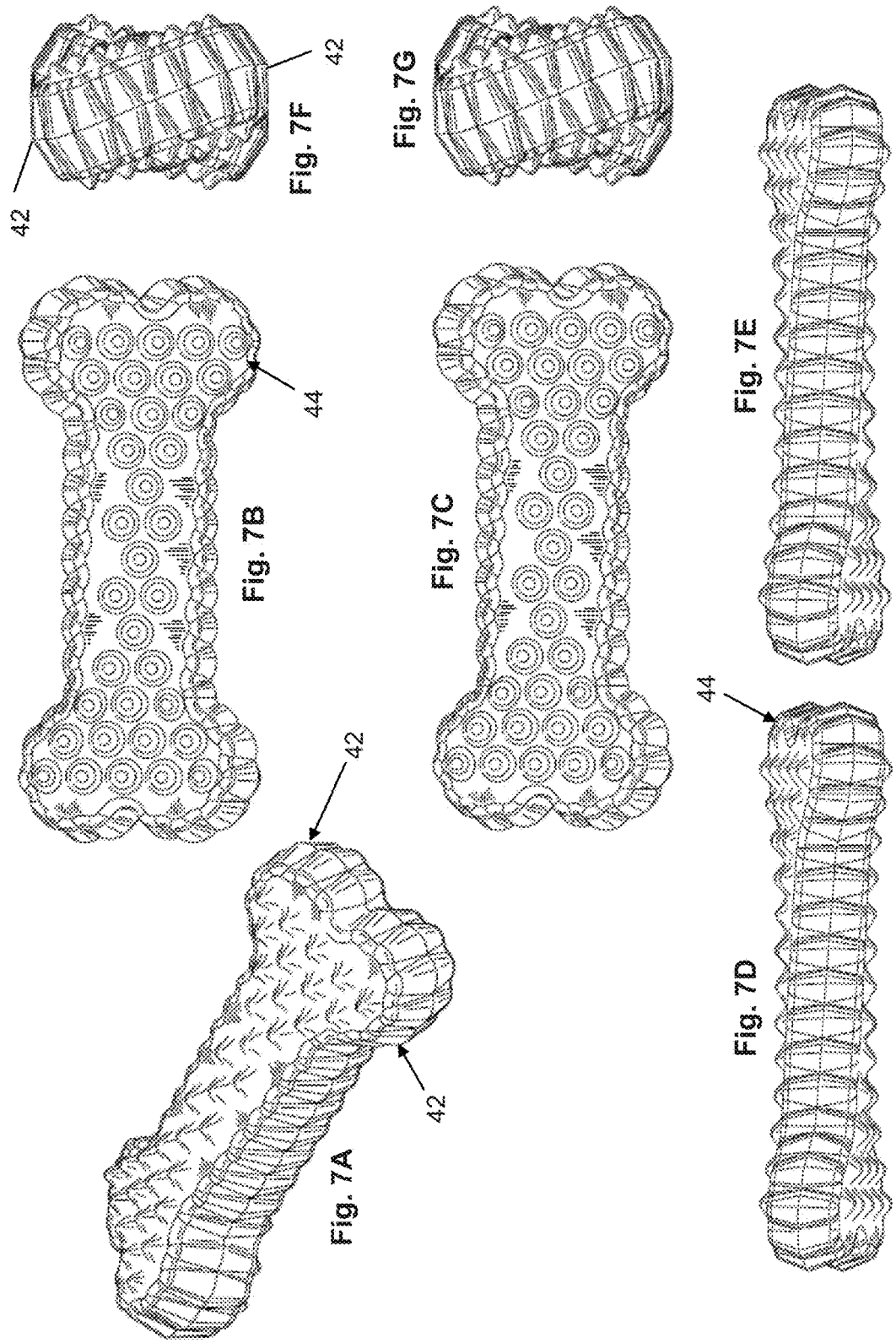

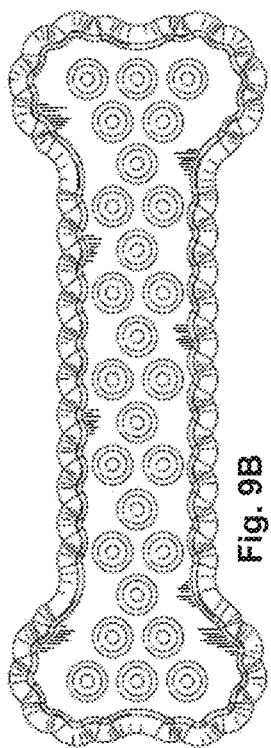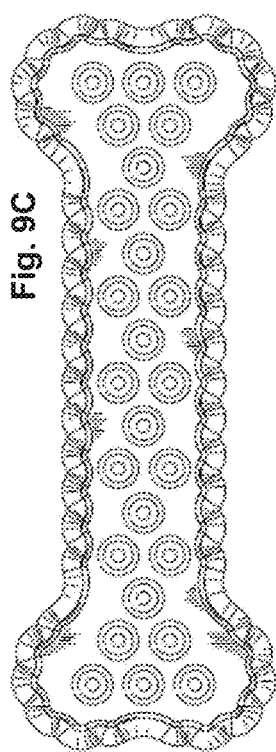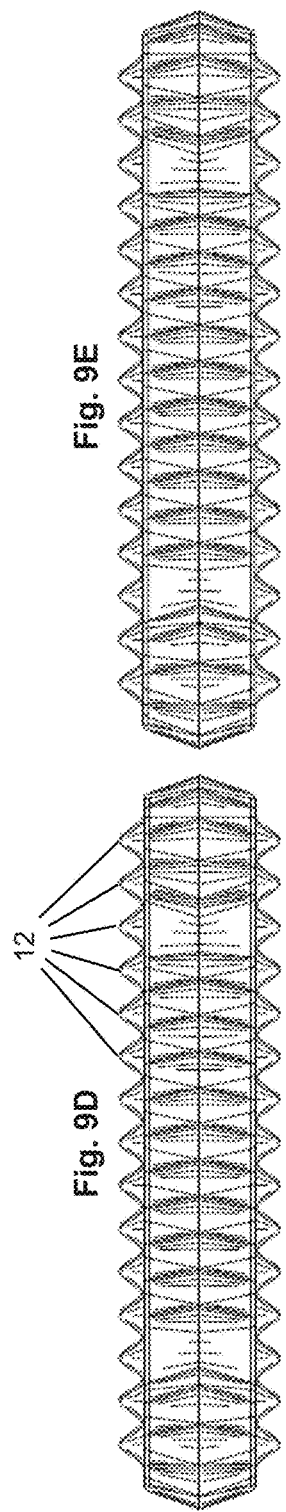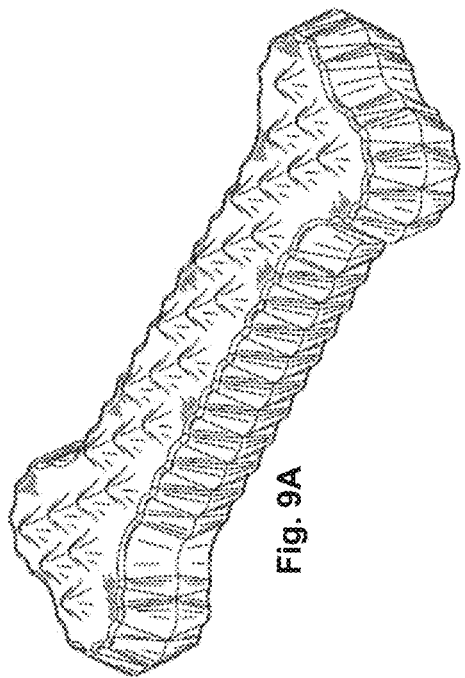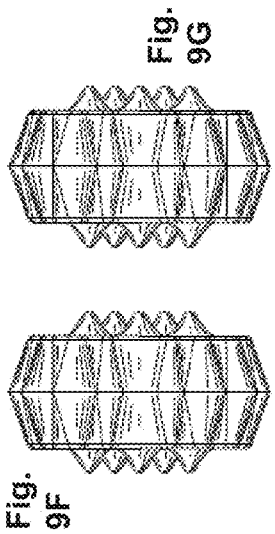

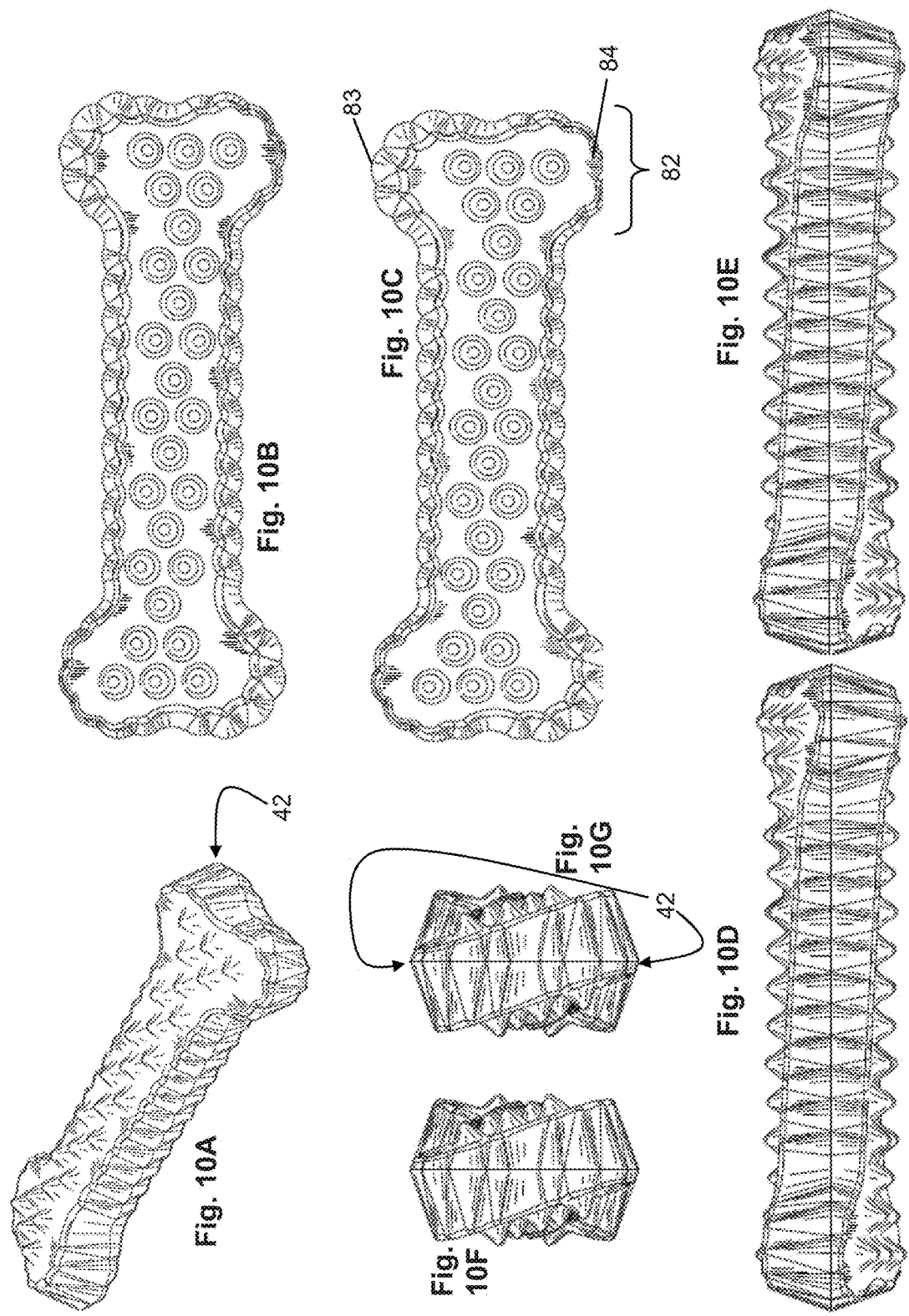

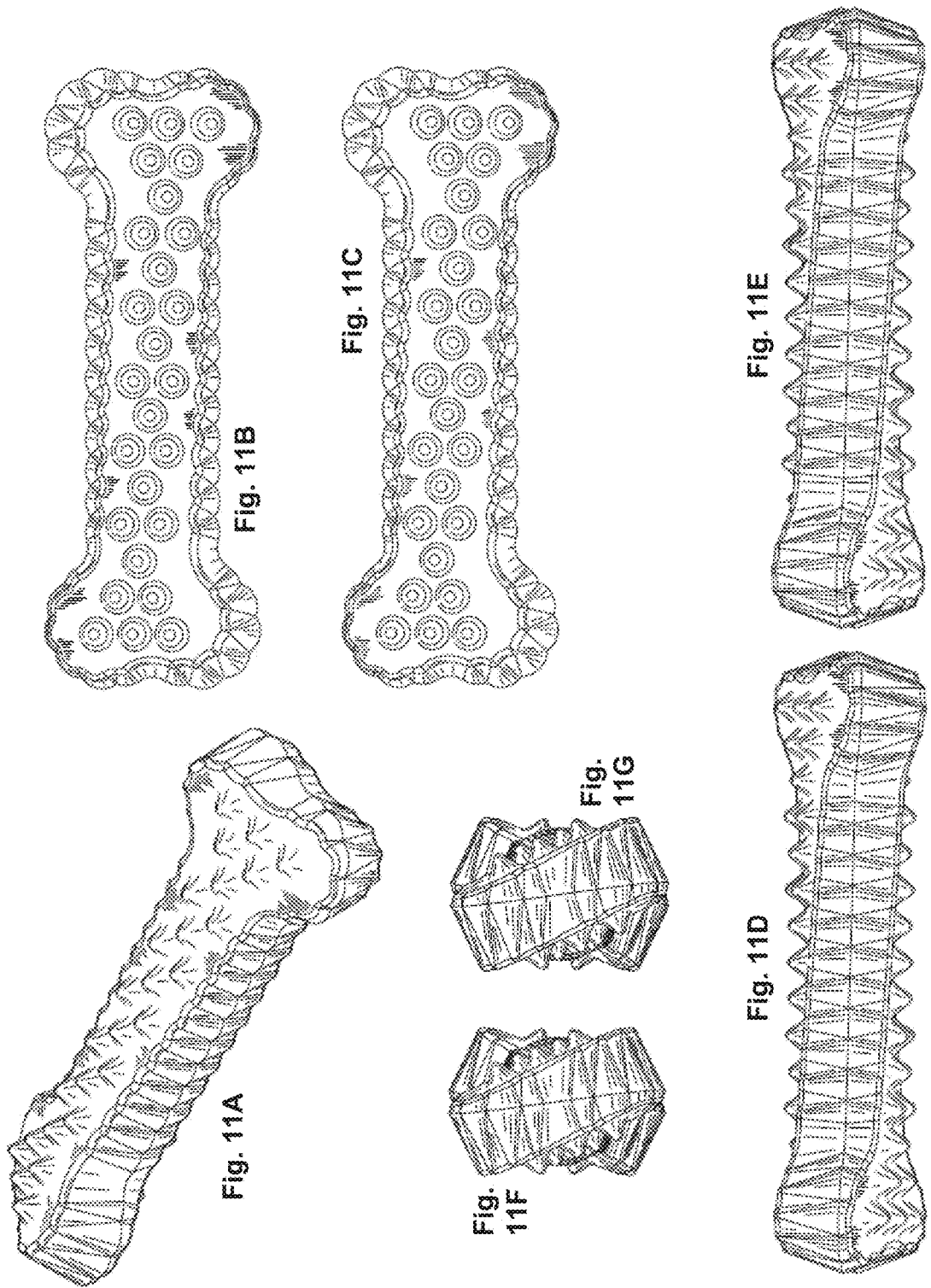

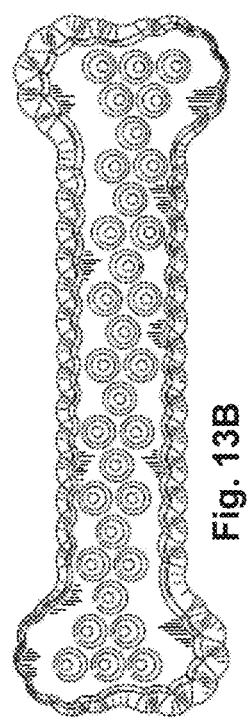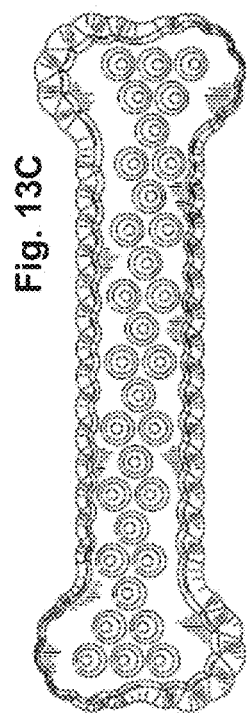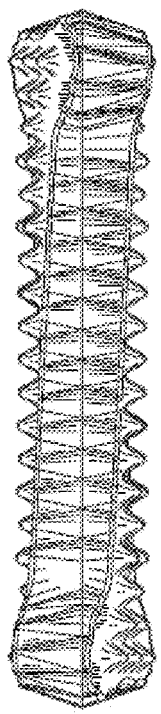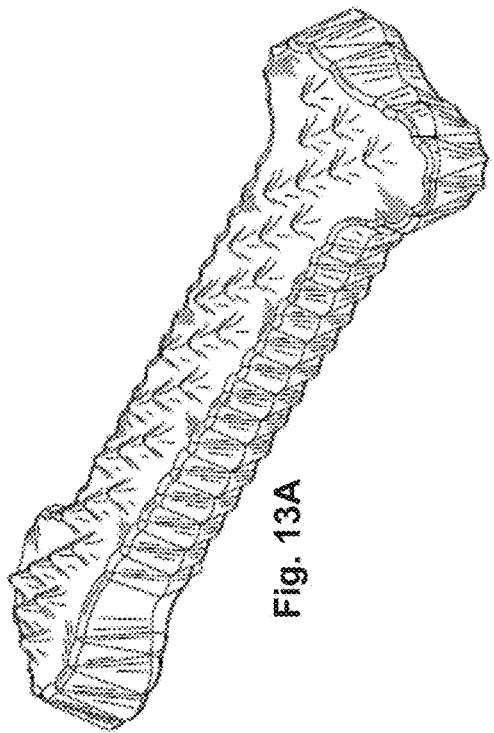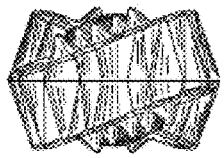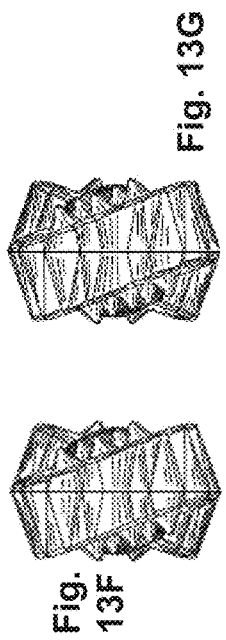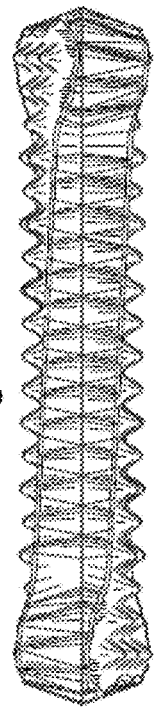

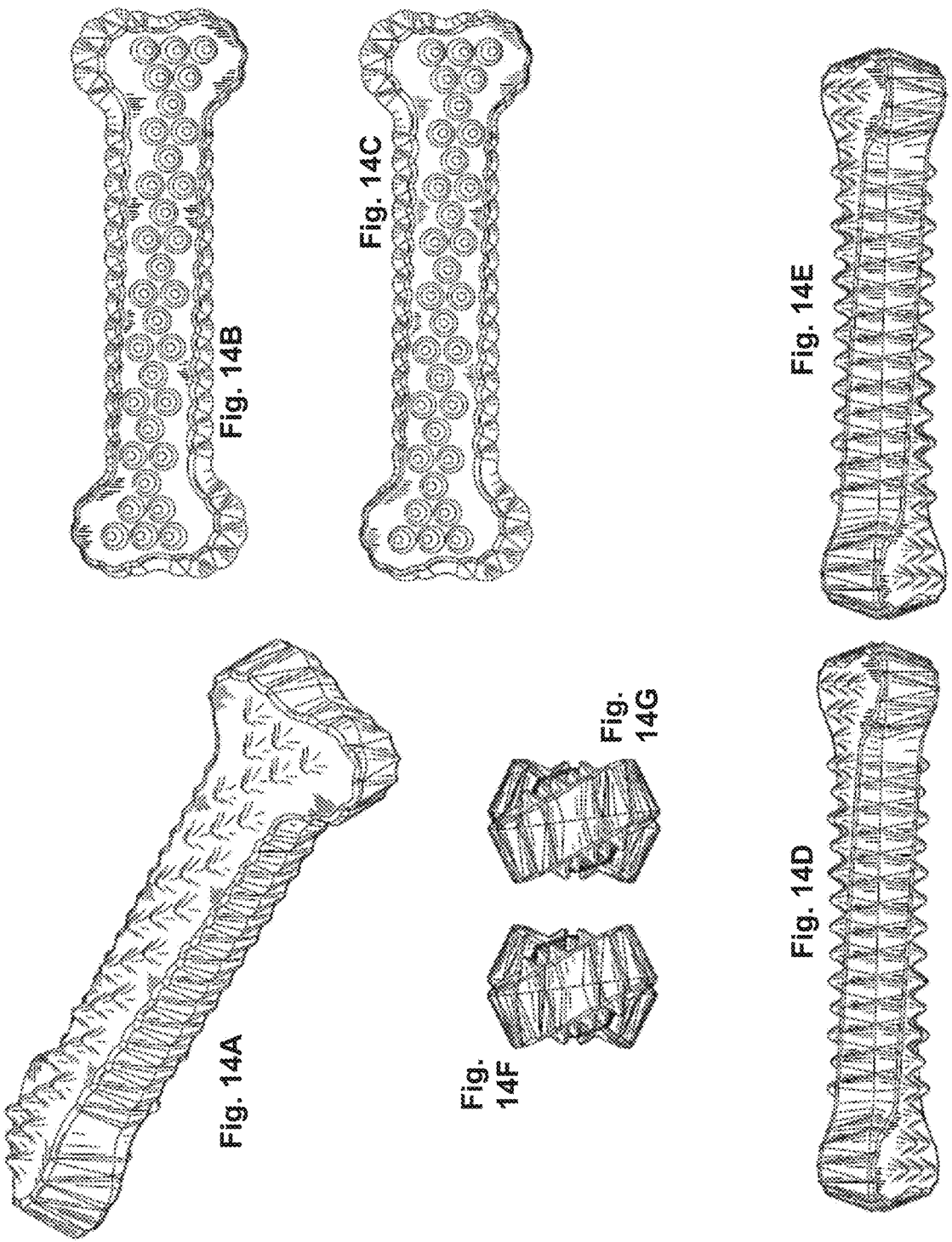

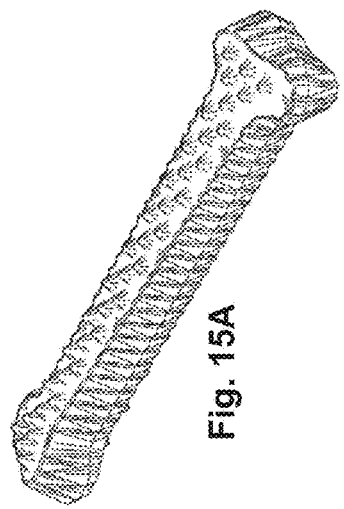
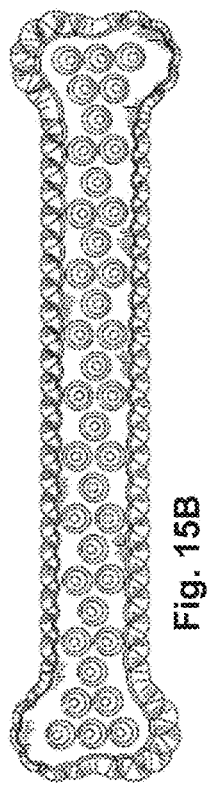
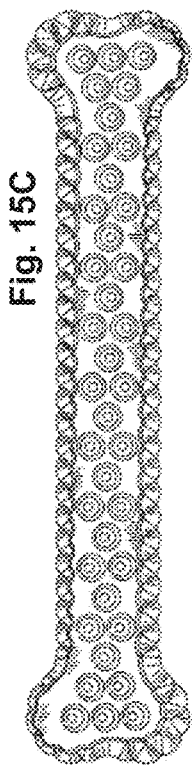
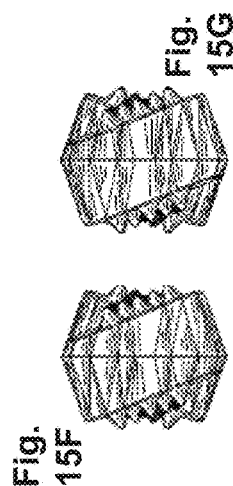
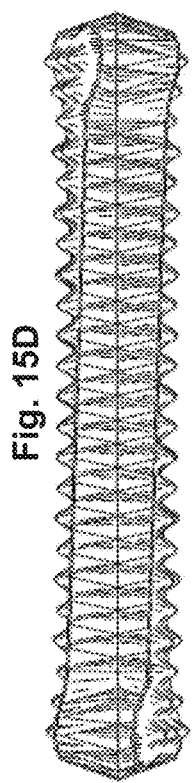
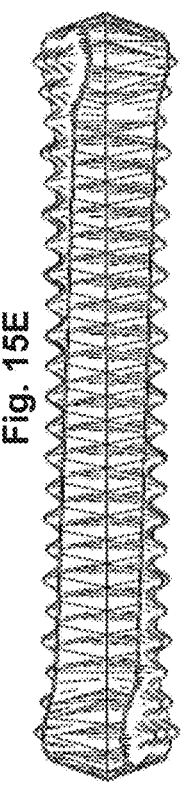
Fig. 15A
Fig. 15B
Fig. 15C
Fig. 15D
Fig. 15E
Fig. 15F
Fig. 15G

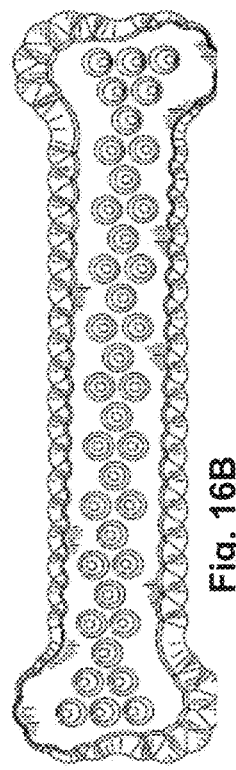
Fig. 16B
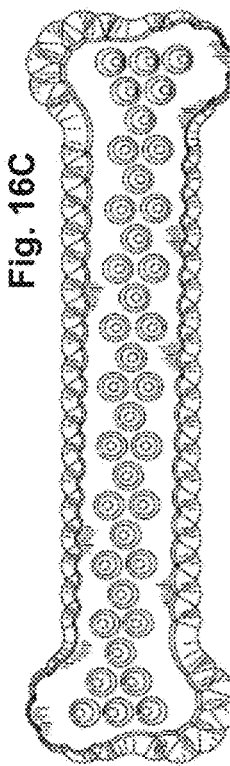
Fig. 16C
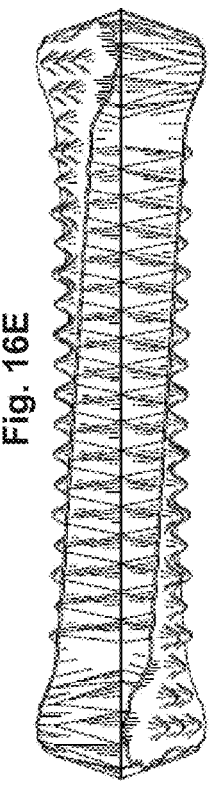
Fig. 16E
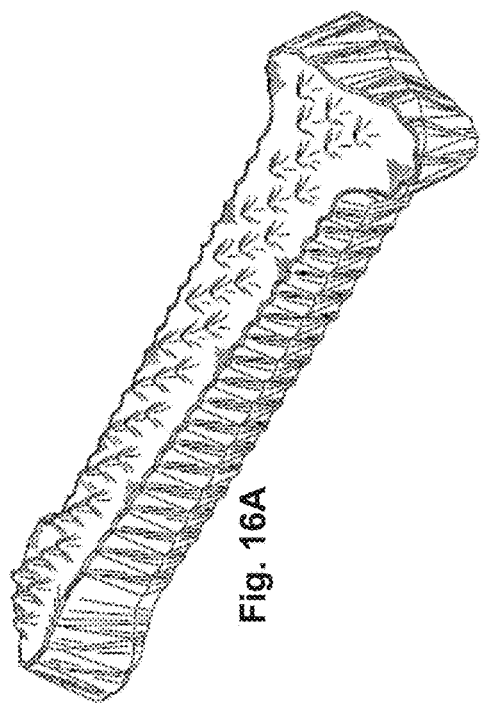
Fig. 16A
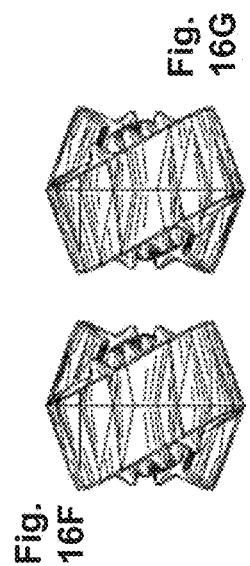
Fig. 16F
Fig. 16G
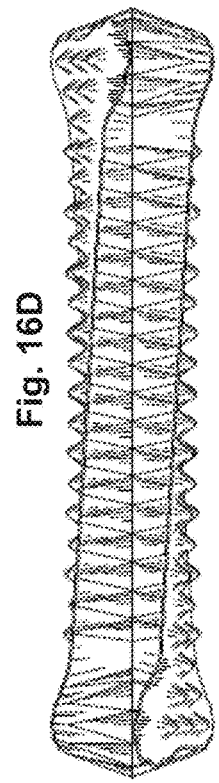
Fig. 16D

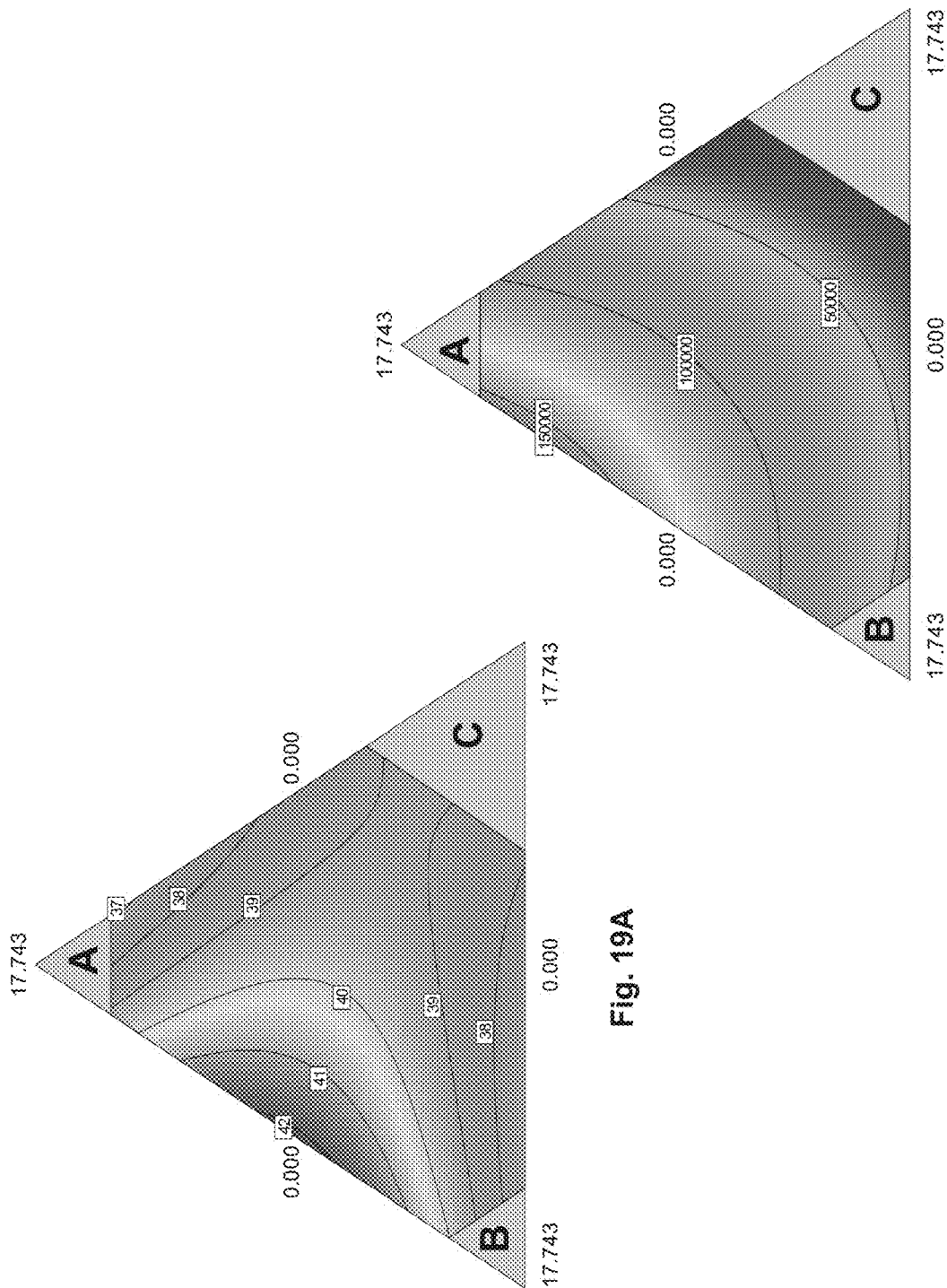

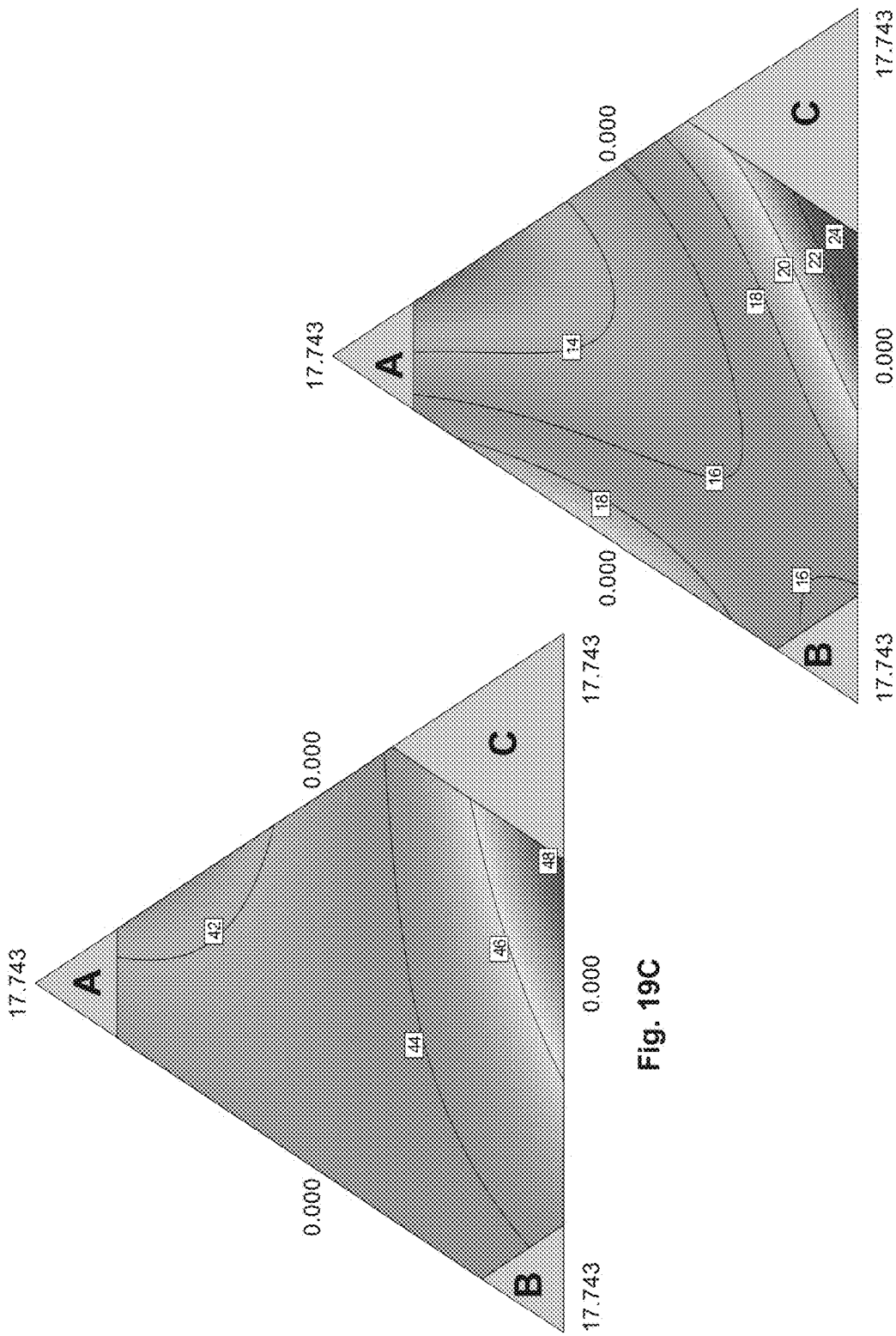

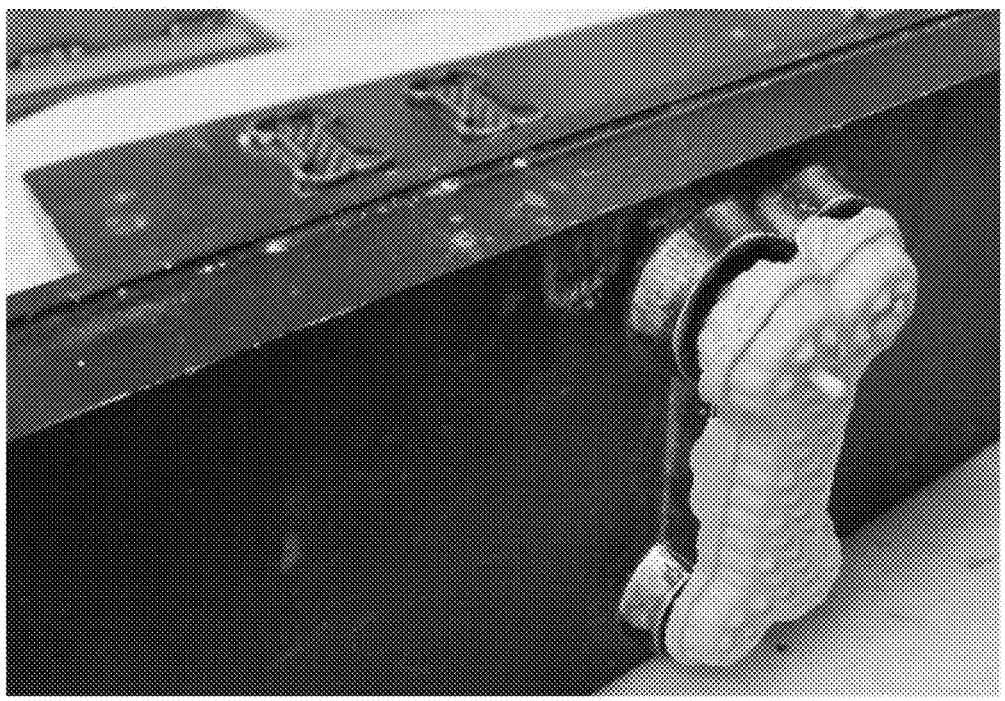
Fig. 20B
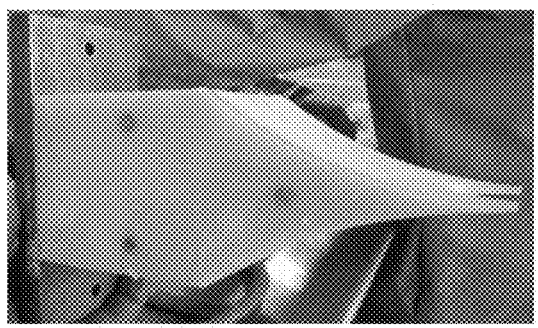 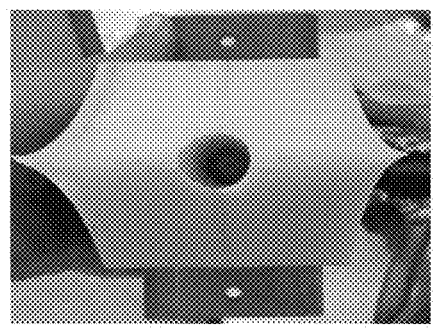
Fig. 21B  Fig. 21C

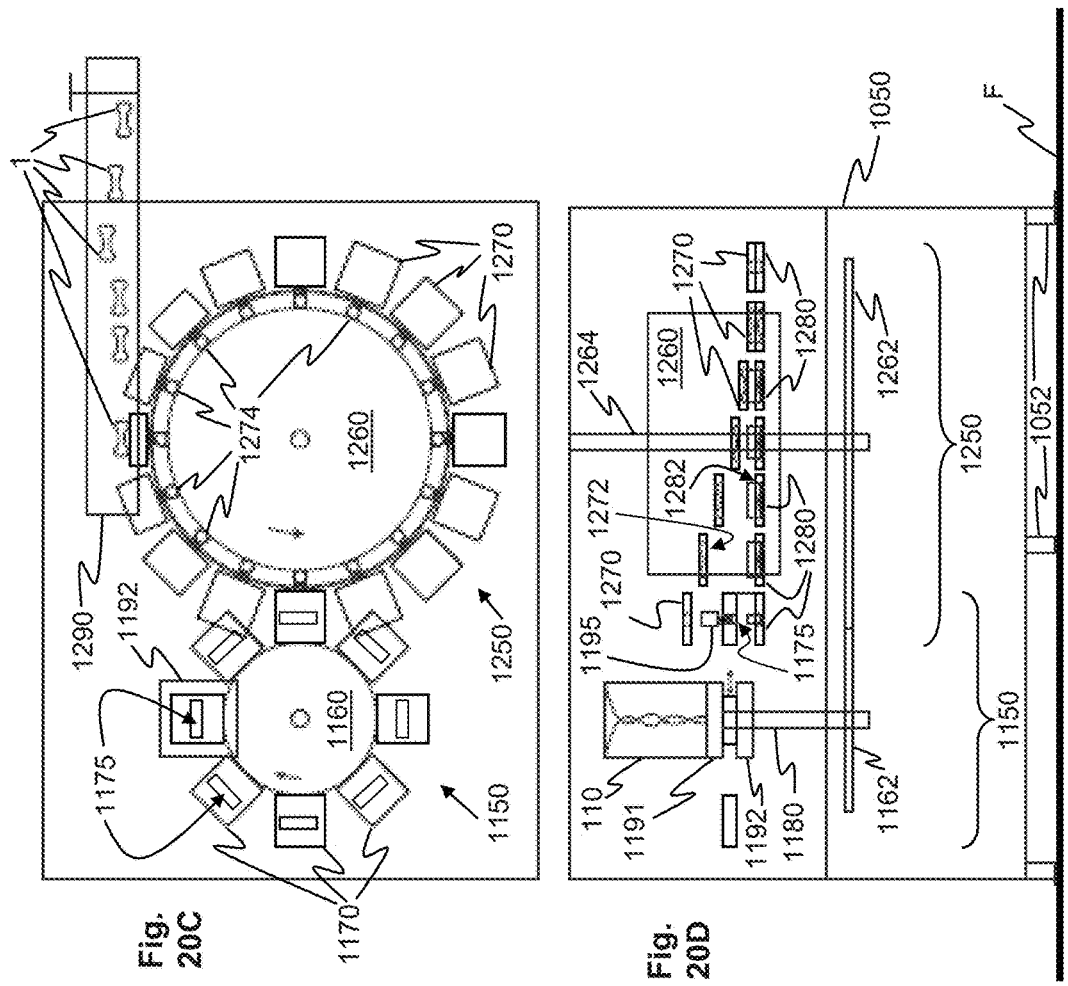

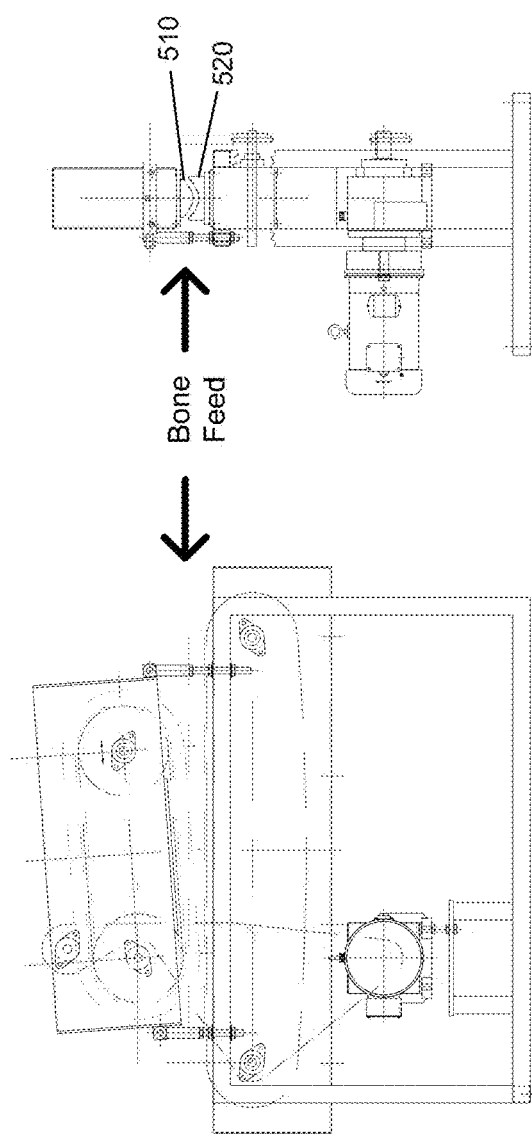
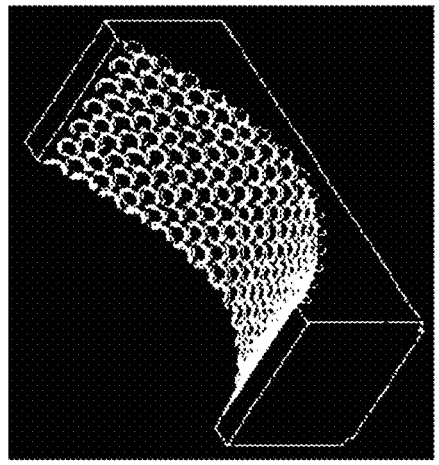
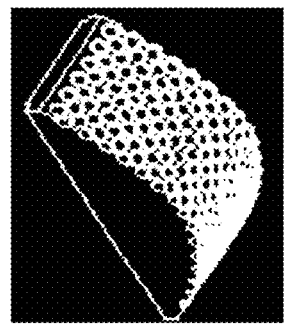
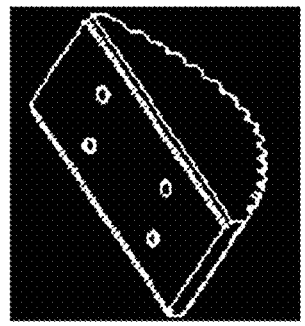

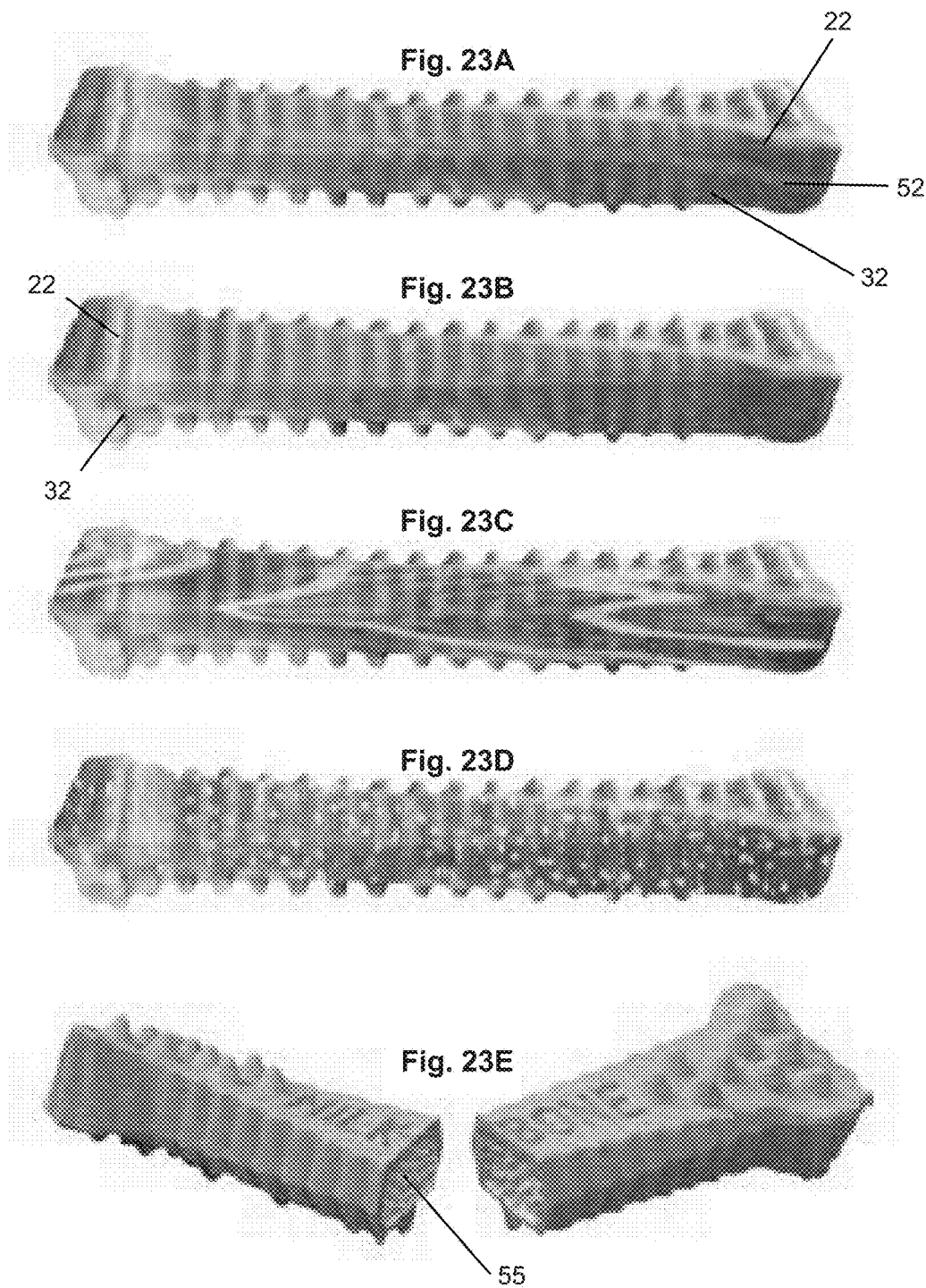

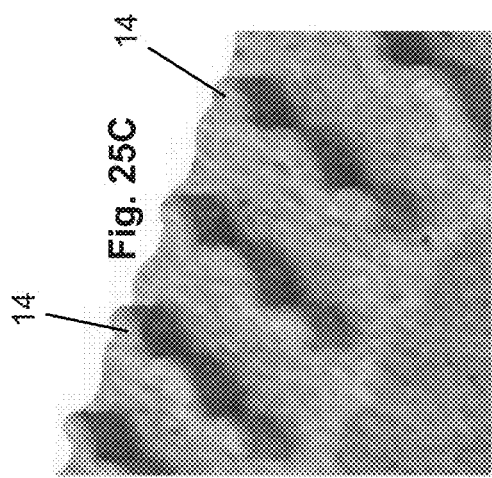
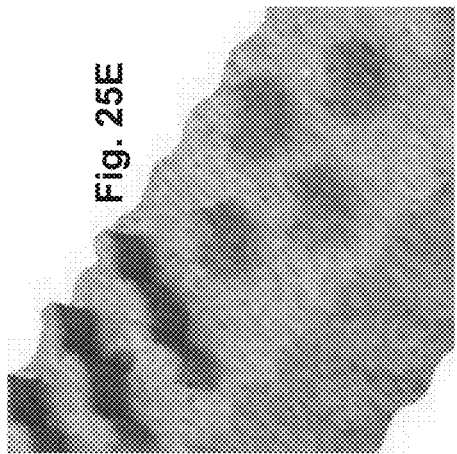
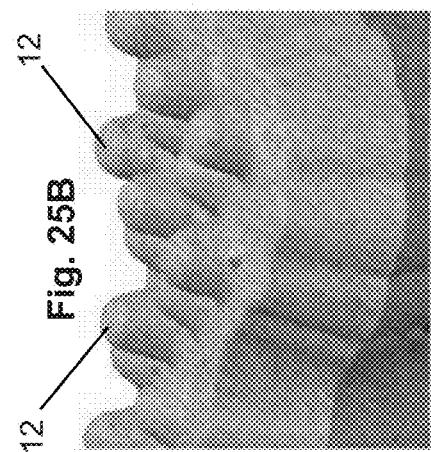
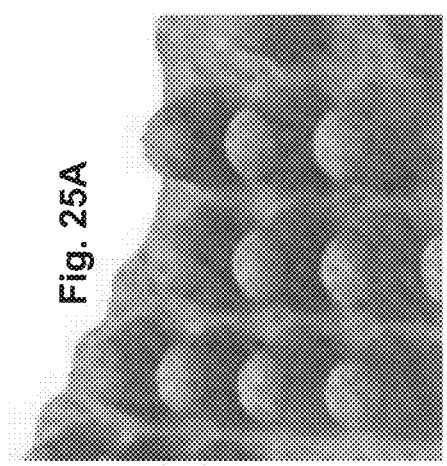
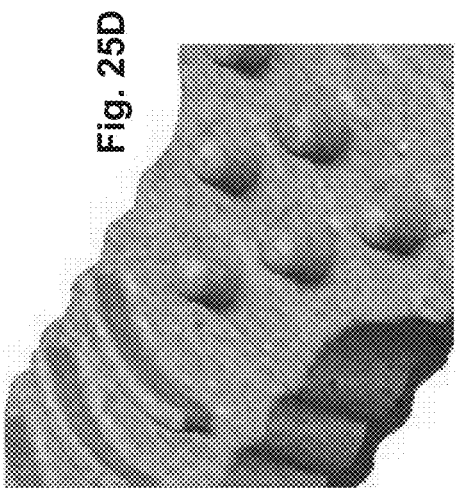

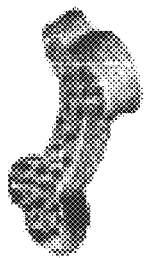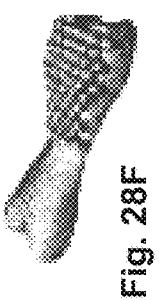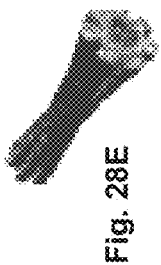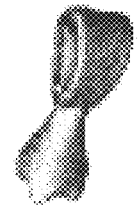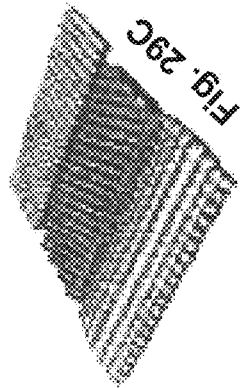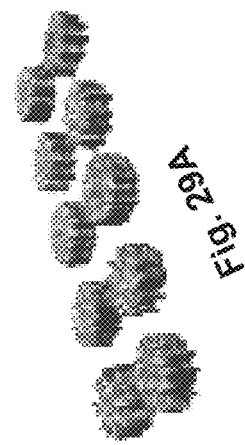

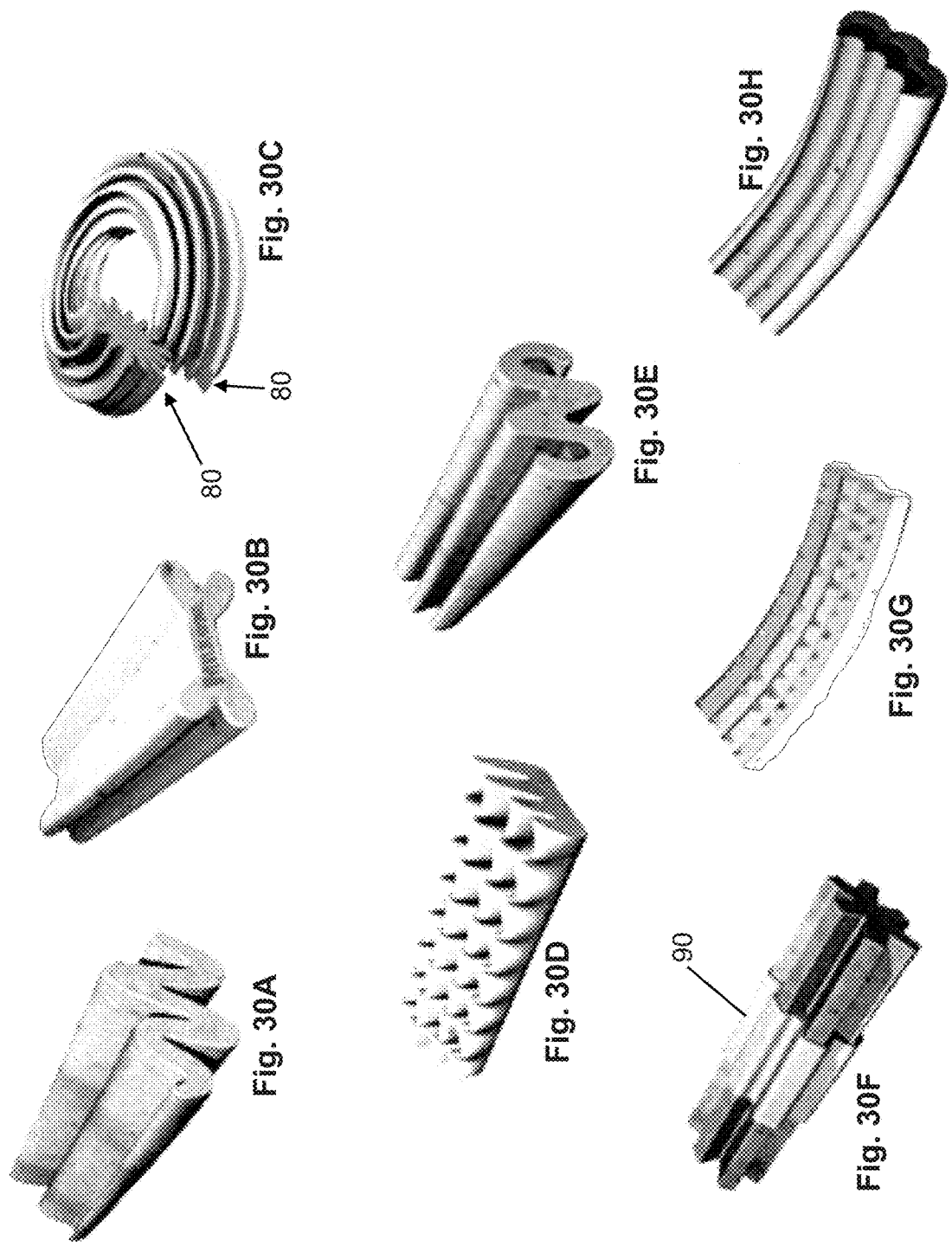

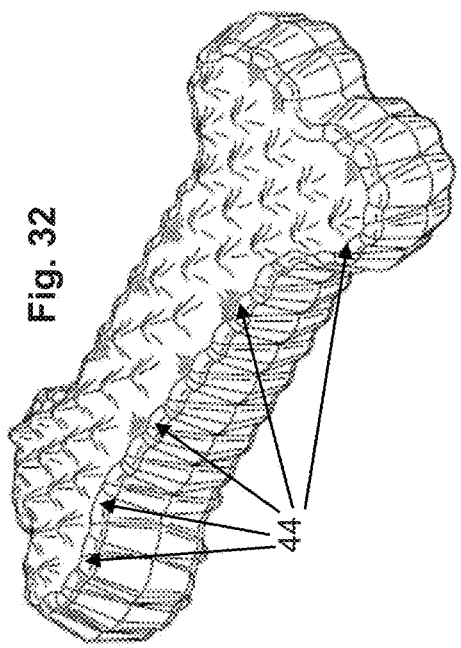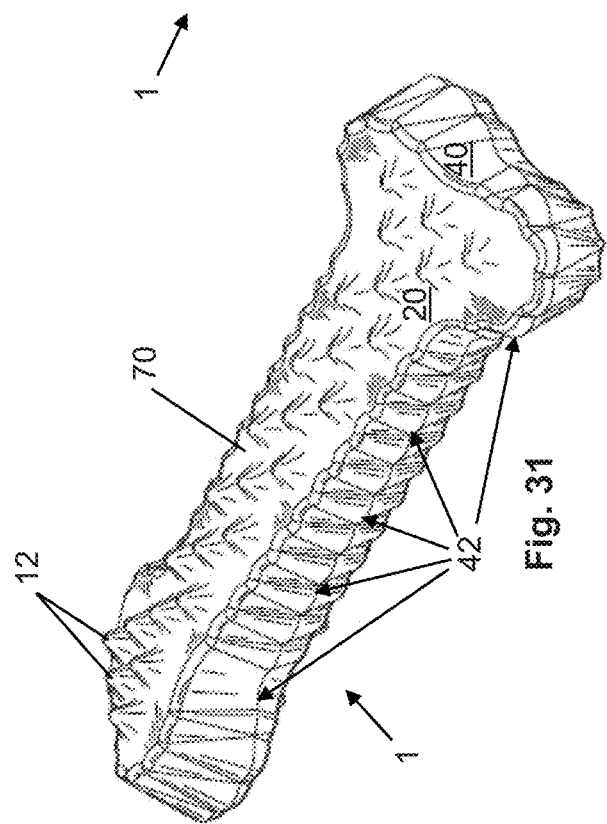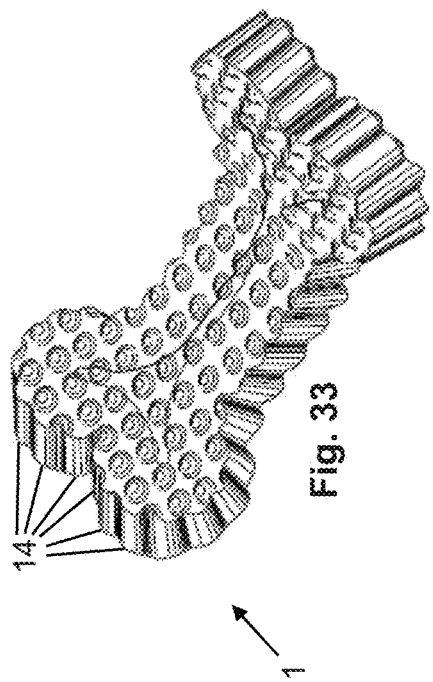

APPETIZING AND DENTALLY EFFICACIOUS ANIMAL CHEWS

CROSS-REFERENCES TO RELATED APPLICATIONS

This application is entitled to priority pursuant to 35 U.S.C. §119(e) to U.S. provisional patent application 61/625,598, which was filed on 17 Apr. 2012.

BACKGROUND OF THE DISCLOSURE

The disclosure relates generally to the field of chewable products for animals, such as pet treats, that promote engagement and oral health.

Certain animals, especially dogs, but also including horses, ruminants, and rodents, are known to chew various articles for purposes other than food consumption. It is believed that such chewing behavior satisfies an animal's urge to chew and that such chewing can have beneficial effects for the dental health and hygiene of the animal.

A wide variety of products are commercially available that can be chewed by animals, especially for domesticated dogs kept as pets. Many of these products are designed to be appetizing to dogs, such as by inclusion of flavorants or aromants that simulate the flavors or aromas of foods enjoyed by dogs. Many of these products are also designed to be consumable, as well as to provide at least some limited dental benefits, such as frictional wiping of tooth surfaces. However, existing animal chew products have several shortcomings.

Such products provide relatively limited dental health benefits, in that abrasion and wiping effects exerted by such chews on animal teeth tend to be substantially limited to primary biting surfaces (e.g., tips of incisors and canine teeth and grinding surfaces of molars and premolars). Some available chews soften substantially upon chewing or fracture into large or sharp fragments, presenting risks of injuries to the throat and other parts of the digestive system. Portions of some animal chew products (e.g., especially dough-based or biscuit-like products) dissolve or become pasty when they absorb liquid, such as saliva, and can leave stains and other residue on surfaces when a wet product contacts the surface, Target animals tend to lack interest in some available animal chew products, whether because of insufficiently enticing taste or smell, objectionable texture or consistency, cumbersome or non-appealing size and shape, disproportionate portion size, or other reasons.

A need exists for improved animal chews which can confer benefits to animals having an urge to chew. The subject matter disclosed herein relates to animal chews which improve upon or overcome one or more of the shortcomings of previously-known products.

BRIEF SUMMARY OF THE DISCLOSURE

This disclosure relates to animal chews that have a consumable portion. The consumable portion includes a chewable matrix and has dimensions selected to fit within the oral cavity of an animal such as a dog. The composition of the chewable matrix includes i) about 9-17 wt % protein, ii) about 40-50 wt % starch, and iii) water. The composition optionally includes a humectant, such as one or both of glycerol and propylene glycol. The water and (if present) the humectant(s) confer chewable plasticity to the chewable matrix in combination with its other components. The chewable matrix should also include an orally active ingredient, such as one or more of dental prophylactic ingredients, breath agents, and pharmaceutical agents. The matrix preferably includes at least one orally active ingredient in an amount that is temporally efficacious (i.e., exerts its desired effect during the time the chew can be expected to remain in the animal's mouth during chewing).

The precise identity, form, and nature of the starch in the chew is not critical. However, some starches and starch combinations can be more beneficial than others for the uses set forth herein. For example, it is preferable that the chewable matrix includes 10-20 wt % amylose. Similarly, it can be desirable if at least about 50 wt % of the starch in the chewable matrix is gelatinized and even more desirable if at least about 80 wt % of the starch is gelatinized. Edible starch obtained from a variety of sources can be used. One suitable source is rice, and a chewable matrix that includes 30-40 wt % starch obtained from rice (e.g., in the form of ground brewer's rice) has beneficial properties. Other suitable sources of starches include wheat, corn, other cereals, sago palm, potatoes, sweet potatoes, tapioca, and yucca.

Also useful are modified starches, such as those generally described as modified food starches. For example, the chewable matrix can include 4-8 wt % of an acid-thinned starch, a dextrin, or a combinations of these.

As with starches, the precise identity, form, and properties of any humectant included in the chewable matrix is not critical. For example, the humectant can be one or more of glycerol, propylene glycol, or other known humectants, and can be present in the chewable matrix in an amount that is about 4-12 wt % of its total composition. In one suitable embodiment, the chewable matrix includes 2-10 wt % of at least one humectant and 14-18 wt % water.

Of course, the chewable matrix can include ingredients other than proteins, starches, water, humectants, and orally active ingredients. Any of a wide variety of agents known to be desirable in animal chews, foods, or medicaments can be included. Examples of suitable additional ingredients include vitamins, minerals, flavorants, aromants, colorants, and preservatives.

A variety of orally active ingredients can be included in the chewable matrix. They can be contained within one or move cavities within the matrix, coated on the outside of the matrix, dispersed in discrete (ordered or random) portions of the matrix, or dispersed substantially homogenously throughout the chewable matrix. Examples of suitable orally active ingredients include dental prophylactic ingredients, breath agents, pharmaceutical agents, and combinations of these.

Dental prophylactic ingredients include various abrasives, such as particulate and fibrous abrasives. Such abrasives preferably exhibit a hardness lower than the hardness of teeth of the animal to which the chew will be given (i.e., so as to avoid harming the enamel or other tooth surfaces), but is preferably harder than substances that undesirably adhere to teeth. Such undesirably adherent materials include plaque, tartar, odorous substances, and biological agents (e.g., bacteria and biofilms) that can induce diseases (e.g., gingivitis) or undesirable conditions (e.g., halitosis). The chewable matrix can include 2-10 wt % of at least one abrasive, for example. Suitable particulate abrasives include a mineral powders (e.g., one or more of gypsum, titanium dioxide, silica, and calcium carbonate), naturally-occurring polymers such as powdered cellulose, and synthetic polymers. Plant particles (e.g., ground husks, brans, or hulls) can be used as particulate abrasives as well. Suitable fibrous abrasives include natural fibers such as plant fibers that are indigestible by the animal (e.g., cellulose) and synthetic fibers such as nylons.

Important classes of dental prophylactic ingredient include anti-plaque agents, anti-tartar agents, and tooth-strengthening agents (e.g., fluoride salts). Examples of suitable anti-tartar agents include metal chelating agents (e.g., polyphosphates such as one or more of sodium tripolyphosphate, tetrasodium pyrophosphate, and sodium hexametaphosphate).

Another important class of orally active ingredients is breath agents, such as one or more of plants, plant extracts, and bicarbonate salts.

Yet another important class of orally active ingredients is pharmaceutical agents. The animal chews described herein are suitable for delivering pharmaceutical agents intended for administration to a gastrointestinal (GI) tract locus proximal to the stomach, such as an oral tissue (e.g., gingival pockets) or the esophagus. Pharmaceutical agents that can be delivered using the chews include antibiotics, anti-inflammatory agents, and topical analgesics, for example. The chews can also be used to administer to an animal pharmaceutical agents intended for systemic administration by way of absorption through mucosa of the upper GI tract. Chews which include bad-tasting ingredients (e.g., many pharmaceutical agents) can include a taste-masking ingredient in an amount sufficient to render the chewable matrix palatable to the animal.

An important characteristic of the animal chews described herein is that they can be readily manufactured in a wide variety of sizes, shapes, colors, and configurations. Such characteristics can be selected to appeal to one or both of an animal and a human that owns or cares for an animal. By way of example, chews intended for dogs can have size, shape, and texture characteristics that dogs find appealing while having visual characteristics that appeal to dog owners. A chew having a 'bone-shaped' conformation including an elongate shaft interposed between two flattened bi-lobed ends, for example, can appeal both to humans (who associate 'bone' chewing with dogs) and to dogs (which may be less interested in the 'bone' shape of the chew than in the sensations associated with chewing it). Color, shape, and surface indicia (or ornamentation) can also be used as indicators of the flavor, texture qualities, or components of the chews. For example, two chews differing in added flavorants aromants can be made to have different colors (e.g., so that human purchasers can differentiate the chews without tasting or smelling them). Further by way of example, chews which include a pharmaceutical agent can have the identity of the agent, dosing instructions, or other relevant information printed upon or imprinted into the chew. Such indicia can also identify functional properties (e.g., breath freshening or tartar scouring) of the chews.

Apart from cosmetic and informational functionality, the shape of the chews described herein can enhance the dental efficacy of the chews and their attractiveness as chewing substrates for animals. For example, nubs, ridges, and other surface features can serve to scour tooth and gum surfaces as an animal gnaws or bites the chew. The shape and topography of the chews can also encourage chewing thereupon by animals such as dogs. By way of example, a 'bone' shaped chew having flattened ends that are rotationally offset from one another (e.g., by 30, 45, 60, or 90 degrees) about the axis of the shaft of the 'bone' can be held between the front paws of a dog while it gnaws on the opposite end of the chew. Surface features present on the shaft or on the gnawed end can scour the dog's teeth, lips, and gums as it does so. For example, the consumable portion of an animal chew can have a plurality of nubs extending outwardly from it. The nubs can have dimensions compatible with being interposed between teeth of the animal when the animal grasps the chew in its mouth.

In a conformation preferred for use with dogs, the chew has a 'bone-shaped' conformation including an elongate shall interposed between two flattened bi-lobed ends that are rotationally offset from one another about the axis of the shaft. The chew has two opposed, twisted, generally parallel flat faces each extending across the ends and shaft, and each of the faces bears nubs thereon. The chew can have ridges on the transitional faces interposed between the two flat faces.

The textural qualities of the animal chew described herein are also important. The texture of the chew can contribute to its functionality, to its appeal as a chewing substrate for animals, and to its desirability to humans for use as a food, health-enhancing product, or toy for animals. In one embodiment, the chewable matrix of the chew exhibits sufficient friability that substantially all of the consumable portion of the chew can be consumed by the animal in not more than four hours of composite chewing time. In another embodiment, the chewable matrix of the chew exhibits sufficient integrity that a substantial portion of the consumable portion of the chew remains non-consumed by the animal after at least one minute of composite chewing time. In yet another embodiment, the chewable matrix of the chew exhibits sufficient rigidity that the chewable matrix does not fracture until it has been chewed at least about 25 times by the animal. In still another embodiment, the chewable matrix of the chew exhibits sufficient ductility that the animal is able to leave a visible indentation in the surface of the chewable matrix upon biting the chew one time. The chew described herein can have a resilient portion fixedly attached to a consumable portion of the chew at an attachment site. In this embodiment, the resilient portion is substantially not consumable by the animal and can prevent the animal from swallowing the remnant that remains after the bulk of the chew has been consumed by the animal.

The favorable characteristics of the chews described herein can complement one another. By way of example, the texture and shape of the chewable matrix and the content of the orally active ingredient in the chew can be selected so that daily consumption of a chew by an animal limits plaque accumulation on the teeth of an animal to a degree that is approximately equivalent to limits on plaque accumulation that are achievable through brushing the animal's teeth using a veterinary dentifrice every other day. Similarly, the chews can be designed to have anti-tartar, disease (e.g., gingivitis) preventive, or breath freshening functionality equivalent to that achievable through other means.

In addition to being objects that animals find desirable to bite and/or gnaw, the animal chews described herein can exhibit dental efficacy, such as tooth-cleaning functionality. The chews can be used to clean the teeth of an animal by providing the chew to the animal. Chews used for this purpose should, of course be designed to include one or more orally active tooth cleaning ingredients (e.g., dentifrices, abrasives, or anti-tartar agents) to effect cleaning of the animal's teeth during the expected residence time (or expected number of chews prior to consumption) that can be expected for the animal to which the chew is given. Chews that contain veterinary pharmaceutical agents can be used to deliver those agents to animals that gnaw upon or consume the chews.

Disclosed herein are a variety of methods of making the animal chew described herein, including its chewable matrix for an animal chew. Generally speaking, these methods include the steps of 1) combining the to form a substantially homogenous mixture: i) about 5-20 wt % protein, ii) about 30-60 wt % starch, iii) about 24-30 wt % water, optionally including a humectant in this amount, and iv) an orally active ingredient;

2) heating the mixture above the gelatinization temperature of the starch to form a melt;

shaping a portion of the melt into a matrix having dimensions selected to fit within the oral cavity of the animal; and cooling the matrix below the gelatinization temperature to yield the chewable matrix.

In these methods, the proportions water and humectant should be selected in amounts sufficient to confer chewable plasticity to the cooled chewable matrix, taking into account any drying of the cooled matrix that will be performed (or performing such drying to achieve a desired final moisture content). The amount of the orally active ingredient should selected such that the chewable matrix comprises a temporally efficacious amount of the ingredient.

A variety of manufacturing methods can be used to practice these methods. For example, the melt can be portioned into billets prior to shaping the billets, for example, by compression molding.

In one embodiment of a compression molding process of this type, the melt is portioned into billets in a portioner and the billets are thereafter shaped in a rotary molder.

In this method, the portioner includes a plurality of portioner plates, each which bears a void extending through the portioner plate. Each portioner plate is circumferentially attached to a rotatable huh at a position at which rotation of the hub causes the portioner plate to pass between a top plate that closely opposes one face of the portioner plate and a bottom plate that closely opposes the opposite face of the portioner plate. A billet volume is thereby defined by the void, as limited by the opposition between the top and portioner plates, and by the opposition between the bottom and portioner plates. The hub of the portioner is spaced apart from a nozzle that communicates with the void in each portioner plate as the plate rotates about the hub. As the void passes the nozzle at a filling position, melt is expelled through the nozzle and passes into the void. The filled portioner plate is rotated from the filling position, past the top and bottom plates, into a discharge position. There, the void contains a billet of melt that is equal to the billet volume. At the discharge position, a knock-out device displaces the billet from the void, transferring the billet to the rotary mold.

In this method, the rotary mold includes multiple opposed pairs of upper mold plates and lower mold plates. These opposed pairs of plates are circumferentially attached to a rotatable hub. The opposed upper and lower mold plates are movable with respect to one another in the direction parallel to the axis of the hub (i.e., one or both of these plates can be moved toward and away from the other). Each upper mold plate bears an upper molding cavity on the face opposite the lower mold plate, and each lower mold plate bears a lower molding cavity on the face opposite the upper mold plate. Each of the upper and lower mold plates is also inclinable between a lowered position substantially perpendicular to the axis of the hub and a raised position substantially parallel to the axis of the hub. Each pair of upper and lower mold plates being sequentially rotatable between at least five positions:

i) a filling position in which the upper and lower mold plates are spaced apart from one another and at least one of the upper and lower molding cavities is positioned to receive the billet as it is displaced from the void in the portioner plate, ii) one or more compression positions in which both the upper and lower mold plates are in their respective lowered positions and at least one of the upper and lower mold plates is moved toward the other;

iii) a closed position in which the upper and lower mold plates are closely opposed against one another and the cavity defined by the upper and lower molding plates defines the form into which each billet is shaped;

iv) one or more casting positions in which the upper and lower mold plates remain closely opposed against one another as the hub rotates; and v) a discharge position in which at least one of the upper and lower mold plates is in its raised position.

In this method, the portioner portions the melt into billets which are displaced from the portioner, received in a mold plate of the rotary molder, and thereafter shaped in and discharged from the rotary molder.

In alternative manufacturing methods the melt can be substantially simultaneously portioned and shaped, such as by using a rotary mold or by injection molding.

In the manufacturing methods described herein, the temperature of the melt is preferably maintained below the boiling point of the melt prior to shaping it. One or more of the additional ingredients described herein can be added to the melt prior to shaping it, either prior to melt formation or thereafter.

Also disclosed herein is an apparatus for forming molded foodstuffs from a moldable extrudate. The apparatus includes a portioner and a rotary molder.

In this apparatus, the portioner includes multiple portioner plates, each bearing a void extending therethrough. Each portioner plate is circumferentially attached to a rotatable hub at a position at which rotation of the hub causes the portioner plate to pass between a top plate that closely opposes one face of the portioner plate and a bottom plate that closely opposes the opposite face of the portioner plate. A billet volume is thereby defined by the void, by the opposition between the top and portioner plates, and by the opposition between the bottom and portioner plates. The hub is spaced away from a nozzle that communicates with the void in each portioner plate as the plate rotates about the hub past the nozzle. At a position designated the filling position, extrudate expelled through the nozzle can pass into the void. Portioner plates are rotatable from the filling position, past the top and bottom plates, into a discharge position. There, the void contains a billet of extrudate that is roughly equal in volume to the billet volume. The apparatus includes a knock-out device for displacing the billet from the void at the discharge position.

In this apparatus, the rotary mold includes multiple opposed pairs of upper mold plates and lower mold plates circumferentially attached to a rotatable hub. Each pair of upper and tower mold plates is movable with respect to one another in the direction parallel to the axis of the hub (i.e., opposed faces of the plates can be moved toward and away from one another, although only one plate need be able to so move to effect such relative movement). Each upper mold plate bears an upper molding cavity on the face opposite the lower mold plate, and each lower mold plate bearing a lower molding cavity on the face opposite the upper mold plate. Each of the upper and lower mold plates is inclinable between a lowered position substantially perpendicular to the axis of the hub and a raised position substantially parallel to the axis of the hub (i.e., the pair can be opened outwardly away from the shaft, like a clam shell attached to the hub at its hinge). Each pair of upper and tower mold plates is sequentially rotatable between at least five positions:

i) a filling position in which the upper and lower mold plates are spaced apart from one another and at least one of the upper and lower molding cavities is positioned to receive the billet as it is displaced from the void in the portioner plate, ii) a series of compression positions in which both the upper and lower mold plates are in their respective lowered positions and at least one of the upper and lower mold plates is moved toward the other;

iii) a closed position in which the upper and lowest mold plates are closely opposed against one another and the cavity defined by the upper and lower molding plates defines the form of the foodstuff into which each billet is shaped;

iv) a series of casting positions in which the upper and lower mold plates remain closely opposed against one another as the hub rotates; and v) a discharge position in which at least one of the upper and lower mold plates is in its raised position.

The portioner portions the extrudate into billets which are displaced from the portioner, received in a mold plate of the rotary molder, and thereafter shaped in and discharged from the rotary molder.

Disclosed herein is a method of enhancing the emotional bond between a human and an animal. This method involves the human repeatedly visibly providing the animal chew described herein to the animal in response to the need by the animal for the article. The bond between the human and the animal is thereby enhanced.

BRIEF SUMMARY OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

FIG. 1, consisting of FIGS. 1A, 1B, 1C, 1D, 1E, 1F, and 1G, is a collection of views of an embodiment of an animal chew described herein. FIG. 1A is a perspective view, in which the front, side, and bottom of the chew can be seen. Other views shown are front elevation (FIG. 1B), rear elevation (FIG. 1C), top plan (FIG. 1D), bottom plan (FIG. 1E), side elevation (FIG. 1F), and opposite side elevation (FIG. 1G) views.

FIG. 2, consisting of FIGS. 2A, 2B, 2C, 2D, 2E, 2F, and 2G, is a collection of views of an embodiment of an animal chew described herein. FIG. 2A is a perspective view, in which the front, side, and bottom of the chew can be seen. Other views shown are front elevation (FIG. 2B), rear elevation (FIG. 2C), top plan (FIG. 2D), bottom plan (FIG. 2E), side elevation (FIG. 2F), and opposite side elevation (FIG. 2G) views.

FIG. 3, consisting of FIGS. 3A, 3B, 3C, 3D, 3E, 3F, and 3G, is a collection of views of an embodiment of an animal chew described herein, FIG. 3A is a perspective view, in which the front, side, and bottom of the chew can be seen. Other views shown are front elevation (FIG. 3B), rear elevation (FIG. 3C), top plan (FIG. 3D), bottom plan (FIG. 3E), side elevation (FIG. 3F), and opposite side elevation (FIG. 3G) views.

FIG. 6, consisting of FIGS. 6A, 6B, 6C, 6D, 6E, 6F, and 6G, is a collection of views of an embodiment of an animal chew described herein. FIG. 6A is a perspective view, in which the front, side, and bottom of the chew can be seen. Other views shown are front elevation (FIG. 6B), rear elevation (FIG. 6C), top plan (FIG. 6D), bottom plan (FIG. 6E), side elevation (FIG. 6F), and opposite side elevation (FIG. 6G) views.

FIG. 7, consisting of FIGS. 7A, 7B, 7C, 7D, 7E, 7F, and 7G, is a collection of views of an embodiment of an animal chew described herein. FIG. 7A is a perspective view, in which the front, side, and bottom of the chew can be seen. Other views shown are front elevation (FIG. 7B), rear elevation (FIG. 7C), top plan (FIG. 7D), bottom plan (FIG. 7E), side elevation (FIG. 7F), and opposite side elevation (FIG. 7G) views.

FIG. 5A is a perspective view, in which the front, side, and bottom of the chew can be seen. Other views shown are front elevation (FIG. 8B), rear elevation (FIG. 8C), top plan (FIG. 8D), bottom plan (FIG. 8E), side elevation (FIG. 8F), and opposite side elevation (FIG. 8G) views.

FIG. 9, consisting of FIGS. 9A, 9B, 9C, 9D, 9E, 9F, and 9G, is a collection of views of an embodiment of an animal chew described herein, FIG. 9A is a perspective view, in which the front, side, and bottom of the chew can be seen. Other views shown are front elevation (FIG. 9B), rear elevation (FIG. 9C), top plan (FIG. 9D), bottom plan (FIG. 9E), side elevation (FIG. 9F), and opposite side elevation (FIG. 9G) views.

FIG. 10, consisting of FIGS. 10A, 10B, 10C, 10D, 10E, 10F, and 10G, is a collection of views of an embodiment of an animal chew described herein. FIG. 10A is a perspective view, in which the front, side, and bottom of the chew can be seen. Other views shown are front elevation (FIG. 10B), rear elevation (FIG. 10C), top plan (FIG. 10D), bottom plan (FIG. 10E), side elevation (FIG. 100, and opposite side elevation (FIG. 10G) views.

FIG. 11, consisting of FIGS. 11A, 11B, 11C, 11D, 11E, 11F, and 11G, is a collection of views of an embodiment of an animal chew described herein. FIG. 11A is a perspective view, in which the front, side, and bottom of the chew can be seen. Other views shown are front elevation (FIG. 11B), rear elevation (FIG. 11C), top plan (FIG. 11D), bottom plan (FIG. 11E), side elevation (FIG. 11F), and opposite side elevation (FIG. 11G) views.

FIG. 13, consisting of FIGS. 12A, 13B, 13C, 3D, 13E, 13F, and 13G, is a collection of views of an embodiment of an animal chew described herein. FIG. 13A is a perspective view, in which the front, side, and bottom of the chew can be seen. Other views shown are front elevation (FIG. 13B), rear elevation (FIG. 13C), top plan (FIG. 13D), bottom plan (13E), side elevation (FIG. 13F), and opposite side elevation (FIG. 13G) views.

FIG. 14, consisting of FIGS. 14A, 14B, 14C, 14D, 14E, 14F, and 14G, is a collection of views of an embodiment of an animal chew described herein. FIG. 14A is a perspective view, in which the front, side, and bottom of the chew can be seen. Other views shown are front elevation (FIG. 14B), rear elevation (FIG. 14C), top plan (FIG. 14D), bottom plan (FIG. 14E), side elevation (FIG. 14F), and opposite side elevation (FIG. 14G) views.

FIG. 15, consisting of FIGS. 15A, 15B, 15C, 15D, 15E, 15F, and 15G, is a collection of views of an embodiment of an animal chew described herein, FIG. 15A is a perspective view, in which the front, side, and bottom of the chew can be seen. Other views shown are front elevation (FIG. 15B), rear elevation (FIG. 15C), top plan (FIG. 15D), bottom plan (FIG. 15E), side elevation (FIG. 15F), and opposite side elevation (FIG. 15G) views.

FIG. 16, consisting of FIGS. 16A, 16B, 16C, 16D, 16E, 16F, and 16G, is a collection of views of an embodiment of an animal chew described herein. FIG. 16A is a perspective view, in which the front, side, and bottom of the chew can be seen. Other views shown are front elevation (FIG. 16B), rear elevation (FIG. 16C), top plan (FIG. 16D), bottom 115 plan (FIG. 16E), side elevation (FIG. 16F), and opposite side elevation (FIG. 16G) views.

FIG. 19 consists of FIGS. 19A, 19B, 19C, and 19D, and is a quartet of diagrams that show the effect of composition on setting time (FIGS. 19A and 19C), hardness (FIG. 19B), and moisture retention (FIG. 19D) for animal chew formulations made as described herein. In FIG. 19, "A," "B," and "C" represent content values (wt %) for "Starch A", "Starch B," and cellulose powder as described herein. Because each of the compositions tested included additional ingredients (e.g., about 38% brewers' rice) in amounts that totaled about 47 wt % of the composition, the diagrams show only the varied components, which constitute the remaining ca. 53 wt % of the composition.

FIG. 20 consists of FIGS. 20A, 20B, 20C, and 20D. FIG. 20B is an image of a mold useful for molding such chews. In the image, a molded chew is shown emerging from a molding plate used to shape one side of the chew. The mold used to mold the exposed side of the chew has been removed and is visible behind the mold from which the chew is emerging. FIGS. 20C and 20D are top and side views of an apparatus described herein for use in a compression molding process for producing animal chews.

FIG. 21 consists of FIGS. 21A, 21B, and 21C. FIGS. 21B and 21C are images of a manifold used to facilitate delivery of extruded materials from the outlet of an extruder to the opposed molding cavities carried by a pair of rollers. In the side view of the manifold shown in FIG. 21B, the curved portions that are opposed against the faces of the rollers are visible. The image in FIG. 21C is a view taken from the 115 right side of the manifold shown in FIG. 21B, and the bore extending through the manifold (corresponding to the notch in the curved surfaces visible in FIG. 21B) is visible. Extruded materials are carried through this bore and emerge into the opposed molding cavities at the surfaces of the rollers opposed against the curved surface.

FIG. 22 consists of FIGS. 22A, 22B, 22C, 22Ci, 22Cii, and 22Ciii. FIGS. 22B and 22C are front and side view, respectively of an embodiment of the forming conveyor 500 depicted in the process shown in FIG. 22A, the forming conveyor 500 comprising at least one convex shaping member 510 and at least one concave shaping member 520 having a complementary shape, so that material introduced between the two members (as indicated by "Bone Feed" in FIGS. 22B and 22C) can be shaped and have its surface molded as the two members are urged against each other. FIGS. 22Ci and 22Cii are views of the convex shaping member 510, FIG. 22Cii showing the shaping surface of the member and FIG. 22Ci showing a face of the member that can be attached to a conveyor mechanism. FIG. 22C iii is a view of the concave shaping member 520 showing its shaping surface.

FIG. 25 consists of FIGS. 25A, 25B, 25C, 25D, and 25E. Each of these figures is an image that depicts surface features of embodiments of chews described herein. FIG. 25A depicts rounded conical projections from a surface of a chew, the projections having approximately the same size and height (the distance from the surface to the apex of the projection). FIG. 25B depicts rounded conical projections from a surface of a chew, the projections having varying sizes and heights (two sizes and heights in this image). FIG.

25C depicts a chew surface having protruding therefrom ridges that have a wavy shape and that are approximately parallel to one another. FIG. 25D depicts a surface having both rounded conical projections and 'C'-shaped ridges projecting therefrom. FIG. 25E depicts a surface having both rounded conical projections and wave-shaped ridges projecting therefrom.

FIG. 27 consists of FIGS. 27A, 27B, 27C, 27D, 27E, 27F, 27G, and 27H and depicts a variety of shapes in which the animal chews described herein can be formed.

FIG. 28 consists of FIGS. 28A, 28B, 28C, 28D, 28E, and 28F and depicts a variety of shapes in which the animal chews described herein can be formed.

FIG. 29 consists of FIGS. 29A, 29B, and 29C and depicts a variety of shapes in which the animal chews described herein can be formed.

FIG. 30 consists of FIGS. 30A, 30B, 30C, 30D, 30E, 30F, 30G, and 30H and depicts a variety of shapes in which the animal chews described herein can be formed.

FIG. 31 is a view of an embodiment of an animal chew described herein.

FIG. 32 is a view of an embodiment of an animal chew described herein.

FIG. 33 is a view of an embodiment of an animal chew described herein.

DETAILED DESCRIPTION

Figure 4F:
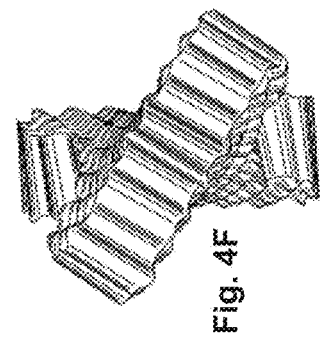
FIG. 4, consisting of FIGS. 4A, 4B, 4C, 4D, 4E, 4F, and 4G, is a collection of views of an embodiment of an animal chew described herein.
FIG. 4A is a perspective view, in which the front, side, and bottom of the chew can be seen. Other views shown are front elevation (FIG. 4B), rear elevation (FIG. 4C), top plan (FIG. 4D), bottom plan (FIG. 4E), side elevation (FIG. 4F), and opposite side elevation (FIG. 4G) views.
Figure 4G:
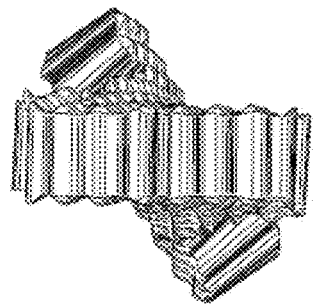
Figure 4B:
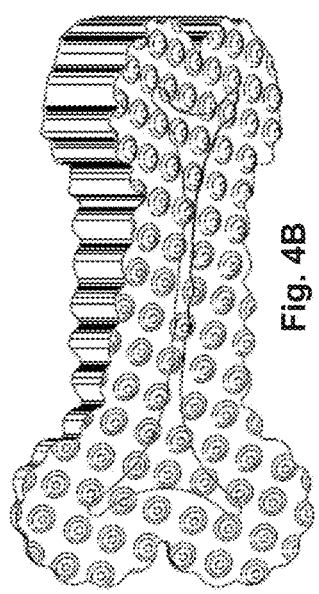
Figure 4C:
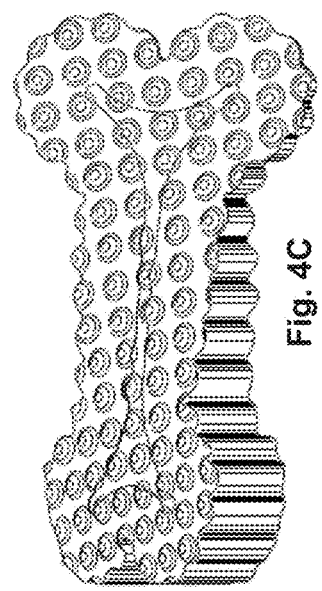
Figure 4E:
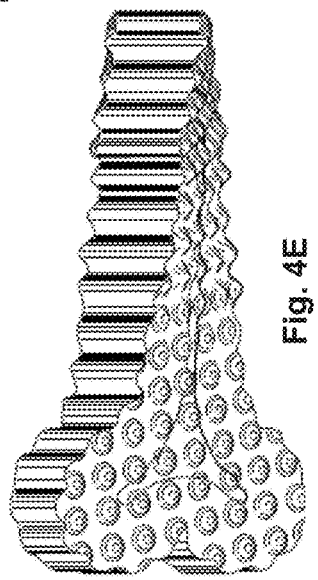
Figure 4A:
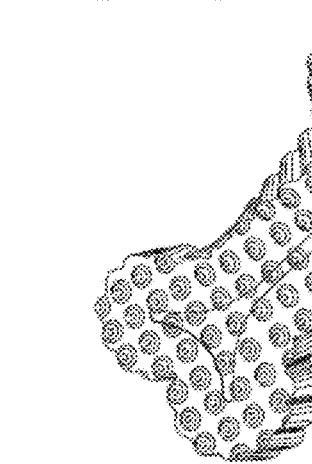
Figure 4D:
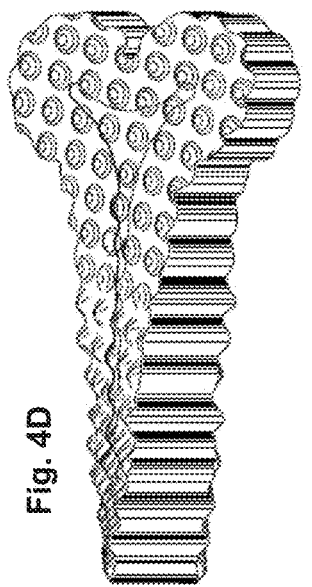
Figure 5F:
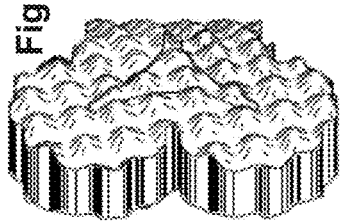
FIG. 5, consisting of FIGS. 5A, 5B, 5C, 5D, 5E, 5F, and 5G, is a collection of views of an embodiment of an animal chew described herein.
FIG. 5A is a perspective view, in which the front, side, and bottom of the chew can be seen. Other views shown are front elevation (FIG. 5B), rear elevation (FIG. 5C), top plan (FIG. 5D), bottom plan (FIG. 5E), side elevation (FIG. 5F), and opposite side elevation (FIG. 5G) views.
Figure 5G:
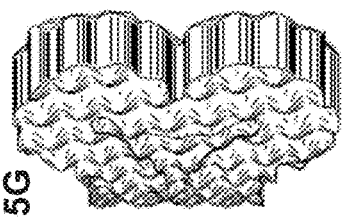
Figure 5B:
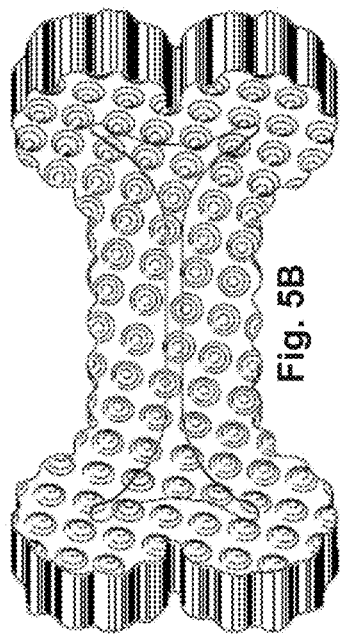
Figure 5C:
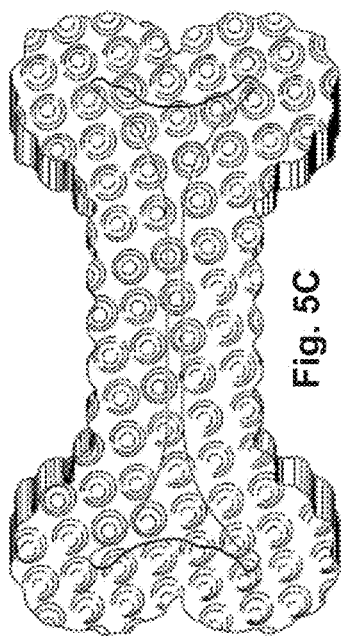
Figure 5E:
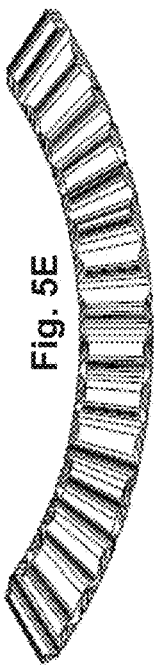
Figure 5A:
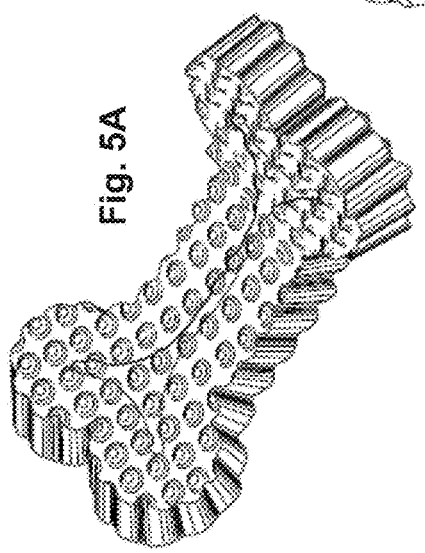
Figure 5D:
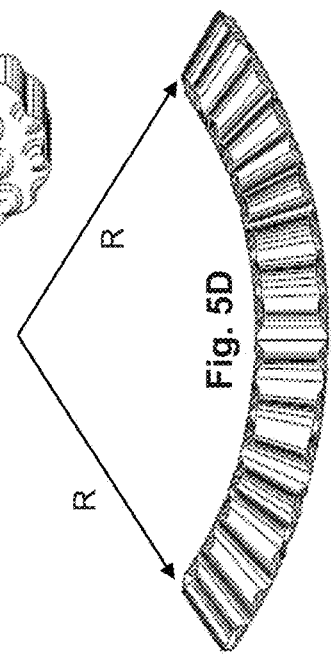
Figure 8B:
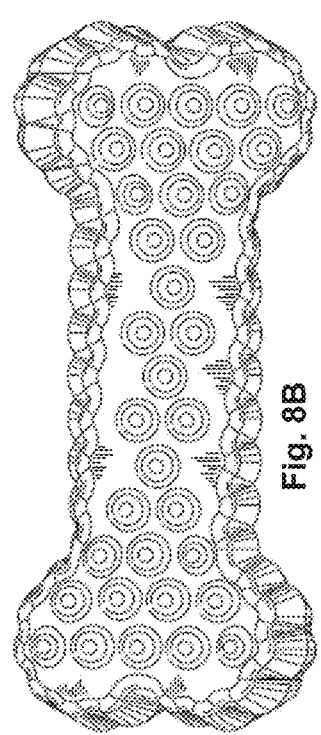
FIG. 8, consisting of FIGS. 8A, 8B, 8C, 8D, 8E, 8F, and 8G, is a collection of views of an embodiment of an animal chew described herein.
Figure 8C:
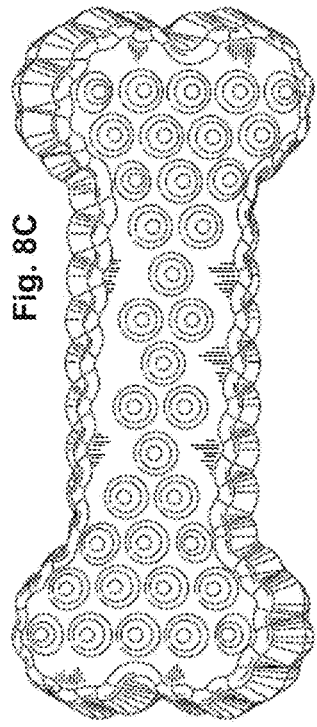
Figure 8E:
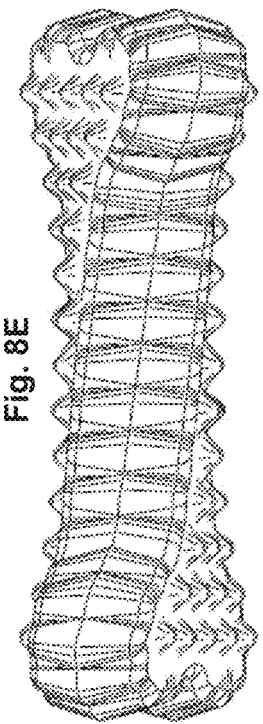
Figure 8A:
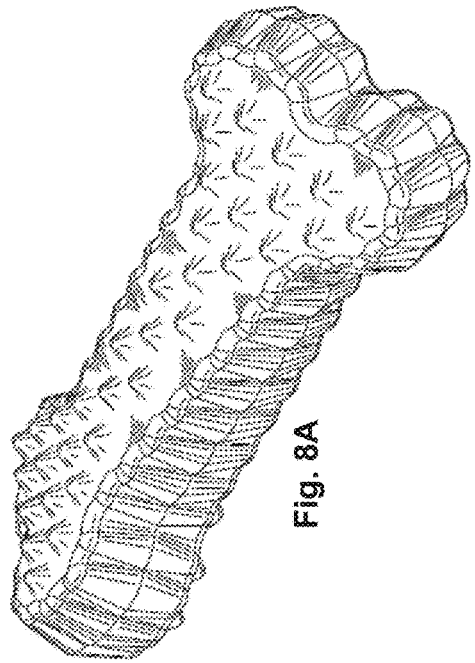
Figure 8G:
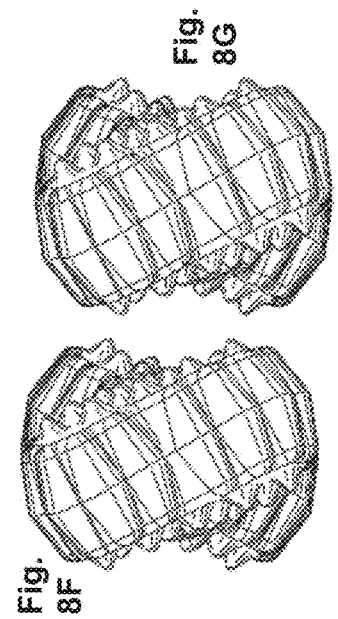
Figure 8F:
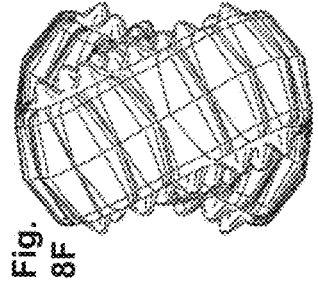
Figure 8D:
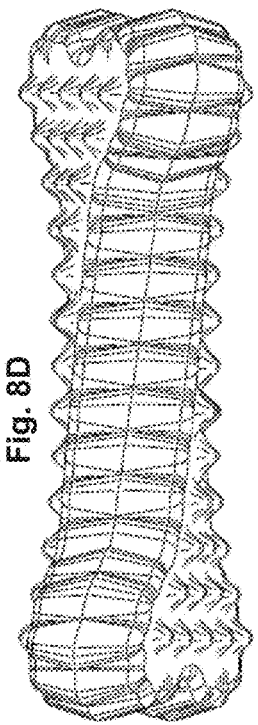
Figure 12B:
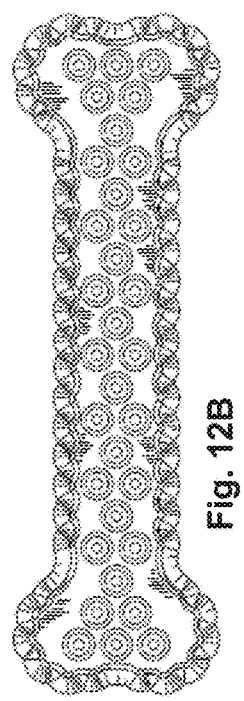
FIG. 12, consisting of FIGS. 12A, 12B, 12C, 12D, 12E, 12F, and 12G, is a collection of views of an embodiment of an animal chew described herein.
FIG. 12A is a perspective view, in which the front, side, and bottom of the chew can be seen. Other views shown are front elevation (FIG. 12B), rear elevation (FIG. 12C), top plan (FIG. 12D), bottom plan (FIG. 12E), side elevation (FIG. 12F), and opposite side elevation (FIG. 12G) views.
Figure 12C:
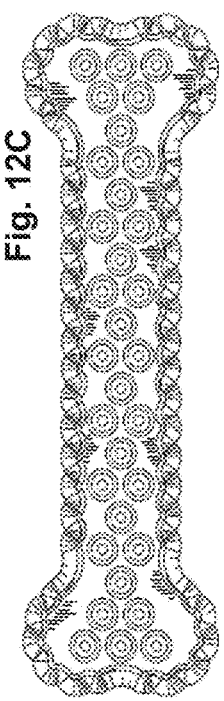
Figure 12E:
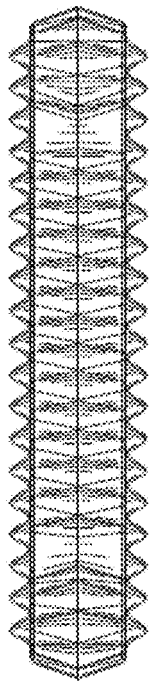
Figure 12A:
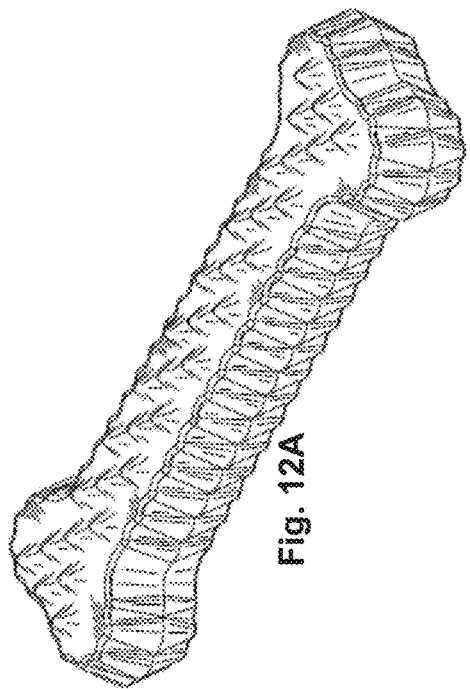
Figure 12G:
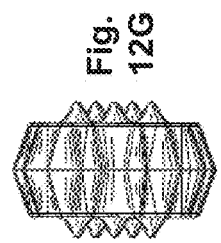
Figure 12F:
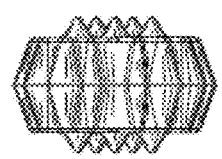
Figure 12D:
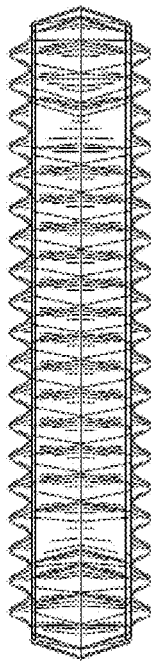

Individuals often seek to provide for both the well-being and the happiness of animals within their care. Animals that tend to chew their food can obtain both of these benefits from chewable articles. Such articles can provide nutrition and functional ingredients that are effective to maintain or improve the animal's medical health. The articles can also provide tactile sensations, tastes, and aromas that, apart from any potential medical or nutritional benefit, improve the subjective or psychological well-being of the animal.

Animals, such as pets, and their human care-givers can develop strong bonds of affection. A significant factor in development of such affection is provision by the human of food and pleasing stimuli to the animals. Apart from recognition of a human as a merely functional source of food and pleasure, it is widely believed that animals are capable of forming psychological bonds with humans akin to those of inter-human friendship and love. Dogs, in particular, are believed to be capable of feeling and expressing intense emotional attachment for their care-givers. Human care-givers also derive satisfaction from their canine interactions.

Individuals who seek to cultivate affection with an animal can facilitate its development by being a regular source of food and pleasing stimuli. In the context of pet care, it is beneficial for a product to be capable of satisfying multiple needs of an animal. Thus, it is beneficial if a dog chew, for example, can satisfy more than one of a dog's urge to chew, a dog's desire to obtain an edible article, a dog's desire to manipulate a plaything, and a dog's wish to share with (or at least obtain from) its care-giver a desirable object, while simultaneously providing a nutritional, veterinary, or hygienic benefit to the dog.

Described herein are animal chews that can be provided to an animal by an individual to enhance the health, happiness, and well-being of the animal and to strengthen the emotional bond between the animal and one who provides for its care.

DEFINITIONS

As used herein, each of the following terms has the meaning associated with it in this section.

A "target animal" simply refers to an animal of the type for which an animal chew product described herein is intended to be used. By way of example, several of the animal chew products described herein are intended to be used by dogs and provided to dogs by their care-givers; a dog is thus the target animal for such products.

An animal chew product or a portion thereof is "chewable" if it is has rheological and other texture and organoleptic properties which tend to promote chewing upon the article by a target animal. Generally speaking, a chewable matrix will exhibit i) sufficient ductility that it is at least slightly malleable when bitten by the target animal, ii) sufficient rigidity that it substantially retains its shape before-and-after a single bite by the animal, even though it may deform or degrade over the course of multiple bites, iii) sufficient integrity that it does not crumble when bitten by the animal the first time, even though it will crumble, break, or both over the course of multiple bites, and iv) sufficient palatability that the target animal is not deterred by its taste from biting it multiple times. By contrast, "chewable" does not mean merely that an article can be chewed by an animal (i.e., it does not mean merely that some portion of the article will fit within an animal's mouth sufficiently to permit engagement of the animal's teeth against the portion).

An "orally active" ingredient is one which exhibits a characteristic property, functionality, or activity after it has been delivered to the oral cavity of an animal.

A "temporally efficacious amount" of an orally active ingredient of an animal chew described herein means an amount that can be expected to exhibit its characteristic property, functionality, or activity during the cumulative period of time during which a target animal can normally be expected to chew upon the animal chew prior to consuming the animal chew.

A "resilient" portion of an animal chew means a portion that is significantly less-quickly-consumable by chewing performed by a target animal than a consumable portion thereof.

A "chew-resistant" portion of an animal chew means a portion that is even less-quickly consumable, such that substantially no part of a chew-resistant portion would be consumed during a normal period of chewing for the target animal.

A "flavorant" is a chemical compound or combination of compounds that imparts a desired taste to a composition to which the flavorant is added.

An "aromant" is a chemical compound or combination of compounds that imparts a desired scent or odor to a composition to which the aromant is added.

The "gelatinization temperature" or "gelatinization point" of a starch has its art-accepted meaning, namely the temperature at which starch granules begin to absorb water and lose birefringence. Qualitatively, it is the temperature at which starch chains become solvated by surrounding water and available to interact with other compounds dissolved or suspended in the water. It is recognized that different regions (e.g., amylose-rich versus amylopectin-dense regions) of individual starch granules can exhibit different gelatinization temperatures.

DETAILED DESCRIPTION

Described herein are chewable articles intended to be provided to animals ("animal chews") for purposes including dental cleaning, breath freshening, nutrition, administration to the animal of beneficial agents, satisfaction of the animal's urge to chew, and general enjoyment by the animal. The articles are believed to represent advances over previously-known animal chews in several respects.

Broadly speaking, the animal chews described herein have a form that includes a chewable matrix having a shape and dimensions selected to facilitate mastication of individual animal chews by an animal. The animal chew can have a non-consumable portion (e.g., a non-consumable rope connecting two consumable matrix portions), but is preferably consumable in its entirety by the animal (like a traditional dough-based biscuit or rawhide chew).

The composition of the chewable matrix includes one or more ingredients that renders it appetizing to the animal (i.e., a flavorant or aromant that tends to induce the animal to chew upon it). The matrix also includes structural ingredients that confer a chewable texture to the matrix, meaning that it exhibits at least deformability (i.e., it is detectably compressible, ductile, or both, to the animal) and sufficient toughness (i.e., resilience, integrity, or both) to endure chewing by the animal for at least a couple of minutes, and preferably for substantially longer. In one embodiment, one or more flavorants and aromants is incorporated that renders the chew appetizing to an animal (e.g., a dog) but unappetizing to humans (e.g., a child).

Depending on the selected ingredients and characteristics of the chewable matrix, the animal chew will not be completely consumed by the animal until it has been chewed for a period of minutes (e.g., 2-60 minutes or longer, such as hours or even days). A consequence of this sustained chewability of the animal chew is that the chewable matrix can be expected to remain in physical contact, in fluid communication, or both, with the oral cavity of the animal for an extended period. For that reason, one or more ingredients that are included in the chewable matrix can be contacted with a surface or fluid in the animal's oral cavity for some or all of the chewing period (at least during periods of active chewing). Thus, the animal chews described herein can be used to deliver active ingredients to the oral cavity of the animal.

The animal chews described herein can be designed so that prolonged chewing by an animal will physically degrade the chewable matrix sufficiently that it can be broken up by the animal into crumbs or parts smaller than the original chew. The broken parts of the chewable matrix can be further broken down or consumed by the animal, contributing to its nutrition and delivering an ingredient present in the chewable matrix to the stomach of the animal. The animal chews thus can be used to deliver substantially any active agent known for oral delivery to the animal, such as medicaments and nutrients. Furthermore, agents that exert a beneficial effect upon an animal owing to mechanical interactions, rather than chemical ones, (e.g., abrasives that scour an animal's teeth or a non-digestible fiber that enhances productivity and regularity of defecation by the animal can be included in the chewable matrix.

The animal chews can be formulated to include in the chewable matrix an ingredient that is beneficial to the health or hygiene of the animal when the chew is masticated by the animal. Hygiene-benefiting ingredients include dentally efficacious ingredients such as abrasives, anti-plaque, and anti-tartar agents, and breath-freshening agents. Health-benefiting ingredients include veterinary pharmaceutical ingredients intended for topical administration in the mouth (e.g., topical analgesics or antibiotics intended to treat an oral lesion) or for systemic or gastrointestinal administration via the oral cavity (e.g., systemic analgesics or anti-helminthic agents). Pharmaceutical ingredients that are useful for facilitating or improving healing or repair of gums vitamin C and various known probiotic agents are among the ingredients that can be beneficially incorporated into the chews, Chews including such ingredients can be used as a mechanism for enhancing compliance by veterinary pharmaceutical subjects.

The animal chews can be made in a wide variety of shapes and sizes. Shapes can be selected to be pleasing to the animal or to its care-giver. Significantly, shapes of the chews, and especially of the chewable matrix, can be selected to enhance the functionality of the chew. Chews intended for dental cleaning effected by abrasion of the animal's teeth against the chewable matrix can be formed with shapes selected to enhance contact between the chew and non-biting portions of the animals' teeth, Chews intended for delivery of an agent with an unpleasant taste can be formed as a hollow chewable shape in which the agent is contained within the hollow in a softer, readily-swallowed composition. The shape selected for the chew can also facilitate grasping and handling of the chew by the animal, such as a twisted shape that will not lie flat against a flat surface such as a floor, Shapes can also be selected to be whimsical having the appearance of a snake or a pretzel) or to simulate the shape of an alternative chewing article (e.g., a bone).

Compositions and properties of, desirable shapes and uses for, and methods of making the animal chews described herein are described in sections below.

Composition of the Animal Chew

The composition of the animal chew (and, in particular, the chewable matrix thereof) is not critical. Animal chews having the shapes and properties described herein can be manufactured from substantially any material capable of assuming and retaining the shapes and exhibiting the properties described herein. Such materials should result in an animal chew product having a chewable matrix that is appealing to the target animal and which can be chewed by the target animal for at least one minute or longer without being substantially completely degraded. The chewable matrix should also not yield sharp-edged or acutely-pointed fragments when chewed by the animal (in order to avoid injury to the animal from chewing of such fragments). The chewable matrix preferably can be degraded upon chewing by the animal to yield relatively blunt "crumbs" of a size amenable to swallowing by the animal (potentially after further chewing of larger fragments). The matrix should be sufficiently digestible that crumbs that are swallowed by the animal can be degraded sufficiently by digestion in the animal's gut that the crumbs do not present a substantial risk of intestinal blockage (e.g., upon swelling of swallowed crumbs induced by absorption of liquid within the gut) or other injury.

The material used to make the chewable matrix is preferably palatable to the animal, and is more preferably perceived by the animal as being appetizing. By way of example, the chewable matrix material can include a foodstuff (e.g., a meat or grain meal) that is generally perceived as appetizing by the animal, a flavorant, an aromant, or a combination of these, in an amount that induces the animal to chew upon the matrix when it is presented with the chew.

The materials and methods used to make the chewable matrix should be selected to yield a matrix that, in addition to being chewable, is digestible by the animal to which the chew described herein is given. Digestibility of the matrix is desirable for portions of the matrix that may be dissolved or suspended in the animal's saliva, for small flecks or crumbs of the matrix that are swallowed, and for larger chunks of the matrix that may be swallowed before being chewed completely to crumbs. Digestibility of the matrix can reduce the likelihood that swallowed materials will be regurgitated by the animal, cause stomach discomfort or upset to the animal, and adversely affect stool formation or defecatory function.

Digestibility of the chewable matrix can be assessed by observing animals who consume the chews. Alternatively, digestibility can be assessed in model systems, such as a stirred beaker filled with simulated animal gastric fluid at the body temperature of the animal. The matrix is preferably sufficiently digestible that crumbs (e.g., ca. 5 millimeter-diameter pellets prepared by grinding or crushing the matrix) are substantially reduced to their insoluble components (e.g., insoluble fiber, ash, and insoluble minerals) within at least about 2 hours of stirring in simulated dog gastric fluid at 101 degrees Fahrenheit and preferably within at least about 60, 45, 30, 20, 10, 5, or 2 minutes of such treatment. Alternatively, digestibility of the chewable matrix can be assessed using an in vitro model system in which the matrix (crumbled or ground) is mixed with a fluid containing digestive enzymes (e.g., pancreatin) representative of those that occur in the digestive tract of animals (e.g., dogs) for which the chews are intended. In a third alternative, ground or broken-up pieces of the animal chew can be contacted with a simulated gastric fluid and then contacted with a simulated (digestive enzyme-containing) intestinal fluid to model passage through the gut of an animal. In each of these test systems, the pH, ionic strength, temperature, and enzyme content of the fluid can be selected to approximate those present in gastric and intestinal fluids of the target animal.

Digestibility of the chewable matrix is influenced by the composition of the matrix (generally, more digestible components yield a more digestible matrix, as will a matrix that can be more easily mechanically broken up by an animal). Digestibility of the matrix is also influenced by the degree to which the melt used to form the matrix is mechanically worked (e.g., the mechanical energy input conferred to the melt by the extruder), by the degree to which the melt is heated or cooked, and the water (or other liquid) content of the melt (greater liquid content can decrease digestibility, presumably by 'lubricating' the melt components and inhibiting energy transfer through mechanical working thereof). Without being bound by any particular theory of operation, the degree of starch gelatinization achieved during melt extrusion is believed to influence the digestibility of the matrix. Starch occurs naturally in a condensed, largely crystalline form that is more resistant to digestion by animals than gelatinized forms of the same starch. Heating and mechanical working of the starch in the presence of sufficient hydration can reduce the crystalline nature of a starch and increase the fraction of starch that is gelatinized.

Highly crystalline starch tends to exhibit low digestibility, most likely because crystalline starch regions are not vulnerable to enzymatic cleavage or other starch-lytic agents in fluids. Highly gelatinized starch tends to be highly digestible to soluble cleavage products in the gut. In order to enhance digestibility of the animal chew described herein, it can be desirable to heat and/or mechanically work (i.e., input mechanical energy into) the starch-containing melt sufficiently that at least about 50% (on a weight basis) of the starch present in the melt assumes a gelatinized form. Preferably, such heating, working, or both, achieves a starch gelatinization level in the melt of at least about 80%.

Even though the identity of the chewable matrix material is not critical, a variety of compositions are described herein of which the chewable matrix of the animal chew is preferably made. These compositions preferably have one or more of the following characteristics:

i) relatively high ratio of starch-to-protein (e.g., starch being present in a two to five-fold excess relative to protein, on a weight basis);

ii) in the starch fraction, an excess of amylose to amylopectin (e.g., a 1.5- to three-fold excess of amylose relative to amylopectin, on a weight basis);

iii) inclusion of one or both of an acid-thinned starch and a low-melting starch e.g., a high-amylose starch, such as sago palm starch);

iv) a low fat content (e.g., a fat content not greater than 5 wt % of the chewable matrix, and preferably not greater than 3 wt %); and v) a substantial content (e.g., about 2-6 wt % of the chewable matrix) of a dentally-efficacious abrasive ingredient, such as one or both of a hard particulate agent and a fiber.

One embodiment of a suitable chewable matrix has a composition that includes about 9-17 wt % protein, about 40-50 wt % starch, water (and, optionally, a humectants) in amounts sufficient to confer chewable plasticity to the chewable matrix after it is melted and formed, and a temporally efficacious amount of an orally active ingredient. The balance of this formula can be substantially any other ingredient that does not materially affect the properties of the ingredients described herein. For example, those other ingredients can include flavorants, aromants, colorants, vitamins, minerals, nutrients, fillers, and preservatives. The ingredients of this matrix formula can be combined, heated above the getting point of the starch (or at least a portion of the starch), and thereafter shaped into the chewable article. Chewable articles thus formed can exhibit the properties disclosed herein.

The identities and proportions of these ingredients are not critical. They can be as specified herein. A skilled artisan will recognize permissible variations in ingredient identities and proportions that can be made for chewable matrices that exhibit the properties disclosed herein.

An important consideration in selecting the ingredients and their proportions for the chewable matrix is that the animal chew formed therefrom (i.e., after heating the mixed ingredients above the gelatinization point of at least some of the starch, forming and shaping of the chew, and cooling to approximately 20 degrees Celsius), should exhibit sufficient friability that substantially all of the consumable portion of the chew can be consumed by the animal in not more than four hours of composite chewing time (i.e., the summed duration of all discrete chewing periods). Although this characteristic will depend on the size and shape of the chew that is selected, the friability of the chew can be selected so that the matrix of an individual can be consumed in less time, such as in two hours, one hour, 30, 20, 10, 5, 4, 3, or 2 minutes, for example, and preferably more than 30 or 60 seconds.

Another important consideration in selecting the ingredients and their proportions is that the animal chew formed therefrom should exhibit sufficient integrity that a substantial portion of the consumable portion of the chew will remain non-consumed by the animal after at least one minute of composite chewing time. Although this characteristic will depend on the size and shape of the chew that is selected, the integrity of the chew can be selected so that the matrix of an individual will remain non-consumed for a greater period of time, such as for 2, 5, 10, 20, 30, 60, 90, or 120 minutes, for example.

The amount of time required for an animal to consume a chew described herein by chewing it will depend on a number of factors that can be selected to achieve a desired chew time. Such factors include, for example, the moisture content of the chew, the amount of pressure applied to the chew during its manufacture, the temperature to which the chew material is heated during manufacture and the amount of time it is maintained at that temperature, the degree to which gas pockets are removed from the chew material during processing (e.g., by application of a vacuum to the molten chew material or by compression), the content of starch and other 'chewy' materials incorporated into the material, the amount of minerals (e.g., gypsum) in the material, and the shape and size of the chew. Different animals will also exhibit different chew times for the same treat (e.g., a large, healthy dog will generally consume the same chew more quickly than a small, unhealthy dog).

Another important consideration in selecting the ingredients and their proportions is how resistant the chew is to fracture upon chewing. It is desirable that the chew ultimately fracture (preferably into relatively small crumbs), and that the pieces be consumable by the animal. However, in order to increase the period of time during which a dentally-efficacious ingredient in the matrix can exert its effects upon the animal's teeth, it is desirable that the chew be sufficiently tough and resilient that the animal must bite the product numerous times before it is reduced to consumable pieces. By way of example, it can be desirable that the chewable matrix exhibits sufficient rigidity that the chewable matrix does not substantially fracture (or, at least, is not reduced to pieces that will be routinely swallowed by the animal) until it has been chewed at least about 25 times by the animal. The ingredients and proportions can be selected so that a greater or lesser number of bites is necessary to fracture or crumble it, such as about 10, about 100, about 500, or about 2000 bites.

Yet another important consideration in selecting the ingredients and their proportions is that the animal chew formed therefrom should exhibit sufficient ductility that the animal finds chewing of the matrix to be desirable. By way of example, the chew should be formed so that the animal is able to leave a visible indentation in the surface of the chewable matrix upon biting the chew with a force less than the maximum bite force that the animal can exert upon the chew. For animals (e.g., aged animals) that can be anticipated to have more fragile teeth than another, healthier animal of the same species and breed, a more ductile chew can be desirable for the aged animal than for the healthier animal.

An important consideration, related to chew time, in selecting the ingredients and their proportions is that residence time of the animal chew in the mouth of the animal. It is desirable that certain ingredients of the chew (e.g., anti-tartar agents and veterinary pharmaceutical agents) be available in the animal's oral cavity (e.g., in its saliva) for a time sufficient to exert a desired effect. For example, it is desirable that teeth of an animal be contacted with an anti-tartar agents for at least 30 to 60 seconds, and preferably 1, 2, 3, 4, or 5 or more minutes. Similarly, pharmaceutical agents intended to act within the oral cavity of the animal typically must be present for a sufficient time (the time depending on the concentration of the agent) to exert a desired physiological or pharmacological effect. The chew time and the appetizing character of the animal chew described herein should be sufficient to achieve an oral residence time of the chew sufficient to permit the action of any such agent(s) included in the composition of the chew.

Animal chews can be made as described herein so that they exhibit one or more (and preferably all) of the friability, integrity, resistance-to-fracture; and ductility characteristics described herein.

Starch

The animal chew preferably includes about 40-50 wt % starch in the chewable matrix thereof. The type and source of the starch are not critical, so long as the other properties of the animal chew are exhibited by the formulation used. To the extent the starch content of the formulation of the chewable matrix is altered beyond this range, starch derivatives and compounds which exhibit starch-like properties can be used. By, way of example, dextrins, pectins, starch hydrolysates, and other natural polysaccharides can be used in place of at least a small proportion of the starch (e.g., 0-5 wt % of the chewable matrix formulation), so long as the replacement exhibits properties like those of the starch it replaces. Furthermore, pregelatinized starches can be included in the materials used to form the matrix.

Modified starches also can be used in the formulation as a part of the overall starch content of the formulation. By way of example, the chewable matrix composition can include no, 2 wt %, or 6 wt % acid-thinned starch, no, 2 wt %, or 6 wt % high-amylose starch, or a combination of these two.

The source from which the starch is obtained is not critical, so tong as the starch is suitable for consumption by the target animal. Considerations of availability, cost, and processability of the starch source can influence selection of an appropriate source. Whole grains, broken grains, flours, roots, and tubers can be used as sources for the starch in the chewable matrix. Examples of suitable starch sources include wheat, rice, corn, potatoes, cassava. These and other sources of starch can be used for the compositions described herein.

As is known in the field of starch chemistry, many combinations of starches can be used to achieve the desired properties of the matrix, and a skilled artisan in the field understands that a certain amount of empirical experimentation and observation normally accompanies development and optimization of starch-containing compositions. Such experimentation is to be expected in connection with development of the chewable matrix compositions described herein. By way of example, it can be seen from the graphs in FIG. 19, that the identities and proportions of starches present in the chewable matrix can significantly influence the properties of the matrix, including its setting time (i.e., time to hardening after melting during processing), hardness, and moisture retention.

The starch content of the chewable matrix is preferably selected so that the matrix contains 10-20 wt % amylose and about 40-30 wt % amylopectin. These proportions can be obtained by selecting a starting material having starch in the selected proportion, by mixing starches from various starting materials, or by supplementing starch from natural sources with modified starches such as acid-thinned or high-amylose starches. By way of example, the matrix can contain 30-40 wt % starch obtained from rice in combination with 4-8 wt % starch that is present in a form selected from the group consisting of acid-thinned starches, dextrins, and combinations of these. By way of an alternate example, the matrix can contain 30-40 wt % starch obtained from broken rice grains (i.e., brewer's rice) in combination with 1-7 wt % starch obtained from sago.

Without being bound by any particular theory of operation, it is believed that gelatinization of starch in the chewable matrix during its processing is responsible for the workability and moldability of the matrix material. Preferably, at least about 50 wt % of the starch in the chewable matrix is gelatinized during processing, and it is considered even more preferable that about 80 wt % of the starch in the chewable matrix be gelatinized during processing.

Polysaccharides other than starches (e.g., pectins, agars, carageenans, and vegetable gums such as guar gums) can be included in the matrix. Inclusion of polysaccharides in a chewable matrix can, generally speaking, be expected to increase the rigidity, integrity, and chew time of the chewable matrix, relative to the same matrix tacking the polysaccharide.

Protein

The source of protein used for the chewable medium is not critical and a skilled artisan is able to utilize protein obtained from any of a wide variety of sources to form the chewable matrix of the animal chews described herein. The protein source can, for example, be relatively pure and well-characterized, such as casein and albumin preparations made from milk and eggs, respectively, or they can be less pure and well-characterized mixtures, such as protein-containing waste (or by-product) streams from meat-processing operations. The protein should be suitable for consumption by the target animal (at least following processing of the protein into the chewable matrix of the formed animal chew), and is preferably digestible by the target animal. Preferably, the protein source is one that is considered appetizing by the target animal, such as chicken, beef, or pork by-products for animal chews intended for dogs. Protein isolates, such as those derived from animal tissues, eggs, or plants can be used. Suitable vegetable-derived proteins such as glutei's can be included, and are preferred for animal chews designed to be free of animal products. Use of such appetizing protein sources can reduce or eliminate the need to add flavorants, aromants, or colorants to the matrix for palatability purposes.

The protein of the chewable matrix should be substantially miscible with the starches of the matrix, at least in its melted state, and should form a substantially homogenous matrix when thoroughly mixed with the starches and other ingredients, melted, and shaped into a chew. Without being bound by any particular theory of operation, it is believed that protein present with starches and water in the melt used to form the chewable matrix in the processes described herein substantially intermixes with the starches to form a hybrid starch-protein structure that contributes, at least somewhat to the chewable matrix properties described herein.

A sufficient amount of the protein source should be included in the chewable matrix to confer a protein content to the matrix of about 9-17 wt % in its finished form. The precise amount of protein included in the chewable matrix is not critical. Also not critical is whether this protein content is derived from a single source or by combination of the protein contents of multiple ingredients of the matrix.

In one embodiment, the matrix lacks any ingredient derived from an animal source, but still contains 9-17 wt % protein, the protein being derived from one or more plant sources instead.

It is known that inclusion of protein-containing ingredients in compositions such as the chewable matrix of the animal chews described herein can affect the properties of the matrix, such as those properties that are described herein. The protein-containing ingredients should be selected together with the other ingredients of the chewable matrix so as to yield animal chews having the desired properties described herein. Formulation of such compositions, including empirical experimentation and observation of formula variations is within the level of skill of an ordinary designer in this field, in light of the teachings provided herein.

Water and Humectants

The chewable matrix should include about 14-18 wt % water in its finished form. The matrix preferably includes about 16 wt % water in its final form. During processing, the matrix can contain a greater water content (e.g., to enhance processability of the matrix), but the final water content of the animal chew should be brought within this range in the finished chew. The source and purity of the water is not critical, so long as the water is suitable for consumption by the target animal, at least following processing of the chewable matrix into an animal chew.

Without being bound by any particular theory of operation, it is believed that water present in the matrix hydrates starches and proteins that are present therein, lubricates or facilitates movement of starch and protein chains, and significantly contributes to the physical properties of the matrix.

Several properties, such as ductility and water retention, of the chewable matrix can be improved by including a humectant in the matrix. When a humectant is used in the chewable matrix, it (or a combination of humectants) should be present in an amount not greater than about 12 wt %, and probably in the range from about 2-10 wt %.

Numerous humectants are known in the art and substantially any humectant can be used, so long as it is chemically compatible with the other components of the chewable matrix and is suitable for consumption by the target animal. Examples of humectants suitable for use in animal chews for dogs include glycerol and propylene glycol.

Other Ingredients

The chewable matrix of the animal chews described herein can contain ingredients other than starches, proteins, water, and humectants. Such ingredients can include fillers that do not materially affect any relevant property of the chew, such as ingredients which provide bulk without substantially affecting the hardness, ductility, or resilience of the chew.

The chewable matrix can include ingredients that affect the palatability, nutritiousness, shelf-life, or appearance of the animal chew without substantially affecting its physical properties (e.g., without substantially affecting the hardness, ductility, or resilience of the chew). Examples of such ingredients include vitamins, minerals, other nutrients, flavorants, aromants, colorants, and preservatives. To the extent that any such ingredient that is included in the chewable matrix affects a desired physical property of the animal chew, the content of one or more of starches, proteins, water, and humectants in the formulation can be adjusted to account for such effects and to maintain the properties of the chewable matrix within desired ranges.

Any vitamins, minerals, or other nutrients included in the chewable matrix should be selected to be present in an amount or concentration suitable for ingestion by the target animal. A wide variety of such nutrients are known for animals, and their selection and dosing for consumable compositions such as the animal chews described herein is within the ken of a skilled artisan in this field.

Flavorants, aromants, colorants, and preservatives should be selected and formulated to be present in amounts that are sufficient to achieve their respective functionalities, but also should be selected both to be suitable for consumption by the target animal and so that they do not leave undesirable stains, aromas, or other residue on surfaces contacted by a partially-chewed animal chew. Preservatives, for example, can be selected to inhibit microbial growth in or other spoilage of packaged animal chews during storage, or they can be selected to inhibit microbial growth upon an animal chew that has been gnawed, but not completely consumed, by an animal so as to reduce the likelihood of illness or digestive upset attributable to growth that might otherwise occur on or in a partially-consumed gnawed during the period between gnawing sessions.

Orally Active Ingredients

A particularly important class of ingredients that can be included on or in the chewable matrix of the animal chews described herein are agents which exert a physiological effect upon the target animal when it gnaws upon the animal chew. Examples of orally active ingredients that can be included are dental prophylactic ingredients, breath agents, anti-halitosis agents (including both those which inhibit or prevent onset of halitosis and those which reduce the intensity of or eliminate halitosis) pharmaceutical agents, and combinations of these. Such ingredients can be dispersed substantially homogenously in the chewable matrix, contained within a selected portion of the matrix, contained within a cavity or hollow within the matrix, coated on the matrix, or some combination of these. Such ingredients can also be disposed on or within a portion of the animal chew other than the chewable matrix (e.g., coating, or contained within a hollow of a non-consumable portion of the chew), so that the target animal is exposed to the agent upon gnawing the chewable matrix of the chew.

Active agents included with the chewable matrix can exert their activities in various ways, and the expected or desired mode of action of such agents can influence where (i.e., on or within the matrix) and how the agents are disposed in the chew.

Agents expected or intended to exert their functionality by way of direct contact with the teeth of the target animal should, of course, be disposed within the chew at a location at which direct contact between the teeth and the chew is anticipated, such as on the surface of, throughout the chewable matrix, or both.

Similarly, agents expected or intended to exert their functionality by way of suspension or dissolution in an oral fluid e.g., saliva or mucus of the target animal should be disposed at a location on or in the chew that is anticipated to be placed in fluid communication with such oral fluids upon mastication of the chew. By way of example, agents active in an oral fluid can be situated on the surface of the chewable matrix, on a surface of the chew other than the chewable matrix, within the chewable matrix (i.e., throughout the matrix or within a cavity or hollow therein), or within a hollow in a compressible portion of a non-consumable portion of the chew (i.e., so that the agent is expelled from the hollow upon compression of the non-consumable portion induced by biting by the target animal).

Active agents intended to be carried by a fluid during mastication can be further subdivided into those agents intended to exert their effect substantially only with the oral cavity of the target animal (e.g., water-soluble dental prophylactic agents, such as fluoride or anti-tartar agents, or pharmaceutical agents intended for topical delivery to oral sites of action) and those agents intended for broader systemic or gastrointestinal (GI) delivery to the target animal. The former, orally-acting agents are preferably disposed within the chew at a location at which the agent will contact an oral fluid over a prolonged period of time (i.e., during most or all of the time while the chew is masticated), so as to effect sustained delivery of the agent to oral sites. The latter, systemically- or GI-acting agents can be disposed more flexibly; an tong as the desired dose is administered during mastication of the article, it does not matter whether the dose is delivered as a relatively short-duration bolus e.g., if the agent is disposed in a soluble coating of the chew) or over a longer duration (e.g., if the agent is disposed throughout the chewable matrix and released as it is chewed).

Dental Prophylactic Ingredients

An important class of orally-active agents that can be administered using the animal chew described herein is dental prophylactic ingredients. Examples of dental prophylactic ingredients include abrasives (for scouring tooth surfaces to remove plaque, tartar, and other materials therefrom), anti-tartar agents, fluoride and other tooth-strengthening agents, surfactants and other surface-cleaning agents, and pharmaceutical agents for topical delivery to teeth and gums (e.g., antimicrobial agents, anti-inflammatory agents, and other agents effective to treat or prevent gingivitis).

Abrasives

Use of abrasives for dental cleaning purposes is well known, and substantially any abrasive known for dental cleaning purposes can be incorporated into the animal chews. The identity of the abrasive is not critical. Suitable abrasives include both particulate and fibrous abrasives. If the abrasive is disposed in a consumable portion of the chew (e.g., on or in the chewable matrix) or if the abrasive is attached to a non-consumable portion in a releasable manner (i.e., so that ingestion of the abrasive by the target animal is anticipated), then the abrasive should be selected to be one that is substantially safe for consumption by the target animal. A large variety of such abrasives are known, including abrasives commonly included in human toothpastes other animal dentifrices.

Suitable particulate abrasives include, for example, mineral powders such as gypsum, titanium dioxide, silica, calcium carbonate, and combinations of these. Other acceptable particulate abrasives include naturally-occurring and synthetic polymer particles, such as particulate celluloses and ground or shredded plant materials.

Abrasive particles should be selected to be compatible with and non-irritating to the oral and GI tissues of the target animal, in addition to being suitable for ingestion. In one embodiment, abrasive particles are selected that exert an abrasive effect within the oral cavity and that are capable of partial or total dissolution with a fluid in the GI tract of the target animal so as to provide a dietary source of a mineral for the animal. By way of example, calcium carbonate and gypsum each act as abrasive particles at the relatively neutral pH of the oral cavity, but can partially dissolve at the acidic pH within the stomach of mammals, yielding soluble calcium ions that can be absorbed by the body. For animals susceptible to development of solid mineral bodies within their bladder, kidney, pancreas, gall bladder, or other organ(s), abrasive particles can be selected that will not contribute to such development by avoiding minerals which so contribute, and these are known in the art.

Suitable fibrous abrasives include plant fibers, such as cotton fibers and grain brans (e.g. rice hulls, coconut husk, and shredded wheat bran). Fibrous abrasives also include synthetic fibers (e.g., nylon or rayon fibers) and semi-synthetic fibers (e.g., cellulose fibers isolated from a plant material). Fibers derived from animals (e.g., collagen fibers derived from tendons, ligaments, and other food animal wastes) can also be used.

Abrasive fibers should be selected to be compatible with ingestion by the target animal. Fibers can be selected that are digestible by the animal, partially digestible, or substantially indigestible. When substantially indigestible abrasive fibers are used in the animal chew, the type and amount of the fibers and their anticipated rate of release from the chew, taken together with other chew components that can be expected to contribute to stool formation, should be selected to avoid accumulation to an undesirable degree within the GI tract of the target animals, so as to avoid complications such as intestinal blockage. Fibrous materials that are, for example, too large in size to be safely fed to small target animals can be processed (e.g., by grinding, shredding, cutting, or chemical or enzymatic degradation) to render them safe for use herein. Such considerations are within the ken of as skilled artisan in this field.

Abrasives should be disposed on or in a portion of the chew that will be contacted by the target animal's teeth for an extended period, most preferably in at least the chewable matrix of the chew. Abrasives exert their cleaning effect by way of mechanical abrasion between the teeth and the abrasive. Accordingly, the abrasive should be relatively rigidly fixed on or at a portion of the chew, so as to provide the mechanical support to the abrasive necessary for it to retain a fixed position while a tooth surface scrapes against an abrasive particle or fiber.

Another concern in selection of abrasive particles or fibers is the effect that such particles my exert as wear upon processing machinery, Mineral particles, for example, having a hardness greater than the hardness of a processing part against which flow of particle-containing material is anticipated can be expected to accelerate wear of the machinery. Selection of abrasives and process machinery construction should therefore be considered together.

The amount of abrasive included within the chew is not critical, and greater abrasive action will generally be expected with increasing amount of abrasive. The amount of abrasive should also be selected to achieve the desired degree of dental cleaning, taking into account the method and duration of chewing that the target animal can be expected to perform upon the chew. Furthermore, the effect of the abrasive upon the properties of the chew (e.g., the hardness, ductility, and resilience of the chewable matrix, if the abrasive is included therein) should be taken into account when selecting the identity and amount of the abrasive(s).

Generally speaking, one or more abrasives is preferably included within the chewable matrix of the chew. Abrasive contents up to about 10 wt % for the chewable matrix are generally considered acceptable, and this content may be divided between two or more abrasives, each of which may be particulate or fibrous. By way of example, the chewable matrix may include 5-7 wt % of a fibrous abrasive and 0-3 wt % of a particulate abrasive. By way of further examples, the chewable matrix may include about 5 wt % of a particulate abrasive and 0-5% of a fibrous abrasive.

A skilled artisan is able to determine, at least empirically, an appropriate amount of abrasive to include in the compositions described herein in order to achieve a desired degree of dental cleaning. By way of example, it is desirable that a degree of dental cleaning equivalent to that achieved by brushing a target animal's teeth every other day, every week, or every other week (i.e., using a traditional brush and an animal-appropriate dentifrice) can be achieved by daily provision to the target animal of an animal chew described herein. More preferably, the degree of dental cleaning thus achieved is equivalent to that achieved by daily brushing of the animal's teeth. Abrasive cleaning action effected by abrasives in the chew can, of course, be combined or supplemented with chemically-based cleaning action effected, for example, by polyphosphates or other metal-chelating anti-tartar agents included in the chew formulation.

The degree of dental cleaning (whether achieved by brushing or by chewing a chew described herein) of an animal can be quantified in any of several ways. Such quantification can be made by examining the amount of dental plaque present on the animal's teeth before and after the cleaning. It can be made by examining the amount of tartar present on the animal's teeth before and after the cleaning. It can instead be made by examining the presence, intensity, or extent of gingivitis occurring in the animal before and after cleaning (or following a period of such cleanings, such as over the course of a week or a month). Of course, these criteria can be combined to form a desired standard. Thus, for example, a claim that the chew described herein cleans teeth as effectively as weekly brushing when a chew is administered to an animal every other day can reference a plaque-based standard, meaning that the degree of plaque removal/prevention achieved by chew administration is roughly equivalent to the degree of plaque removal/prevention achieved by brushing.

When present in the chewable matrix, the abrasive may be substantially uniformly dispersed therein, dispersed in discrete regions thereof, coated on the surface of the matrix, or a combination of these. The abrasive may, for example, be thoroughly mixed with the other dry ingredients of the chewable matrix prior to their combination with wet ingredients, resulting in a chewable matrix having the abrasive disposed substantially uniformly throughout. Alternatively, a wet preparation of the abrasive may be crudely mixed with the remaining, hydrated ingredients of the chewable matrix prior to melting and forming, resulting in a chewable matrix having 'pockets' of abrasive material disposed therein (the uniformity of the disposition depending on the degree and aggressiveness of the mixing). In still another alternative, an abrasive may be mixed with an adhesive containing a volatile solvent and the mixture may be sprayed on the exterior of a formed animal chew, resulting in a chew having a thin layer of abrasive adhered to the exterior surface thereof.

In addition to exerting an abrasive effect, an abrasive applied to the surface of an animal chew can serve other purposes, such as lubricating manufacturing components and conferring a desirable texture to the exterior surface of the chew. By way of example, a bolus of melted chewable matrix made as described herein, a mold used to shape it, or both, can be dusted with a particulate mineral or with a powdered cellulose to reduce the degree of adhesion between the melt and the mold (by becoming interposed between the hot melt surface and the mold surface and preventing direct contact therebetween). A chew formed in this manner will have a surface texture determined in part by the texture of the particulate or powder which forms part of its surface. Such a chew may have a rougher texture that is pleasing to the mouth of the target animal, to the hand of a human providing the chew to the target animal, or both.

Abrasives are preferably selected to have a hardness less than the actual or anticipated hardness of the teeth of the target animal. Such abrasives can be expected to scour the surface of the teeth against which they are scraped without damaging the tooth itself (e.g., without scratching tooth enamel).

Anti-Tartar Agents

Anti-tartar agents are another important class of dental prophylactic ingredients that can be included with the animal chews described herein. As with abrasives, anti-tartar agents can be included on or in a chew at substantially any location and in any configuration in which contact between the anti-tartar agent and a tooth surface can be effected. They can, for example, be included at any surface. Or within any material that is anticipated to contact an oral fluid during mastication of the chew.

Anti-tartar agents are preferably situated on, within, or both on the surface of and within the chewable matrix of the animal chews described herein. Such a configuration will tend to enhance contact between the agent and tooth surfaces of the animal, since it is upon the chewable matrix that the target animal can be expected to chew. Preferably, one or more anti-tartar agents is disposed throughout the chewable matrix, so that tooth surfaces are contacted with the agent throughout the period during which the target animal masticates the chew.

The identity of the anti-tartar agent(s) included in the animal chew is not critical. Numerous such agents are known in the art, as are the concentrations at which their respective anti-tartar effects. Substantially any known anti-tartar agent(s) can be used in the animal chews, consistent with the other parameters set forth herein. By way of example, the amount and identity of the agent used should be consistent with the desired properties (e.g., hardness, ductility, and resilience of the chewable matrix) of the chew and the suitability of the agent for ingestion by the target animal.

A suitable class of anti-tartar agents for use as a component of the chewable matrix in the animal chews described herein is metal dictating agents. Many such agents are known and are used in human and veterinary dentifrices. Polyphosphates are common anti-tartar agents, their efficacy and safety for this purpose having long since been established. Suitable polyphosphates include sodium tripolyphosphate, tetrasodium pyrophosphate, sodium hexametaphosphate, and combinations of these. EDTA (ethylenediamine tetraacetic acid) and related compounds are also well known metal-ion chelating agents. Without being bound by any particular theory of operation, metal chelating agents are believed to exert their anti-tartar effects by binding metal ions that help to maintain the structure of tartar on tooth surfaces. Particularly when used in combination with abrasives, anti-tartar agents can lead to tartar removal by weakening the physical structure of tartar. Because the efficacy of metal chelating agents for anti-tartar purposes can be inhibited by the presence of free metal ions, animal chews which include a metal-chelating anti-tartar agent should be formulated to limit free metal ions released from the animal chew upon its mastication.

Green tea extract and other plant extracts are known to have tartar-inhibiting and -removal functionality, and such extracts can be incorporated into the chews described herein.

Tooth-Strengthening Agents

Another class of dental prophylactic ingredients suitable for use in the animal chews described herein is fluoride-containing compounds and other tooth-strengthening agents, such as sodium monofluorophosphate. Such agents and their use for dental prophylactic purposes are well known in the art, and substantially any of them may be included in the animal chews describe herein, so long as the identity(ies) and amount(s) of such agents are consistent with the other parameters of the chews sa forth herein hardness, ductility, and resilience of the chewable matrix and suitability of the agents for ingestion by the target animal).

Surface-Acting Agents

Yet another class of dental prophylactic ingredients suitable for use in the animal chews described herein is surface-acting agents, such as surfactants and tooth enamel-whitening agents. Such agents and their use for dental prophylactic purposes are well known in the art, and substantially any of them may be included in the animal chews describe herein, so long as the identity(ies) and amount(s) of such agents are consistent with the other parameters of the chews set forth herein (e.g., hardness, ductility, and resilience of the chewable matrix and suitability of the agents for ingestion by the target animal).

Prophylactic Pharmaceutical Agents

Still another important class of dental prophylactic ingredients suitable for use in the animal chews described herein is prophylactic pharmaceutical agents intended for topical delivery to teeth and gums. Examples of such pharmaceutical agents include antimicrobial agents, anti-inflammatory agents, and other agents effective to treat or prevent gingivitis. Other examples include antibacterial or antiviral agents intended for topical application to oral lesions. A wide variety of such agents and their use for dental therapeutic and prophylactic purposes are known in the art. Substantially any of them may be included in the animal chews describe herein, so long as the identity(ies) and amount(s) of such agents are consistent with the other parameters of the chews set forth herein (e.g., hardness, ductility, and resilience of the chewable matrix and suitability of the agents for ingestion by the target animal). Veterinary pharmaceutical agents having therapeutic effect are included within the class of dental "prophylactic" ingredients in recognition of the fact that treatment of oral disease symptoms and conditions will often prevent further problems, as well as for the sake of convenience. Terminology notwithstanding, veterinary pharmaceutical ingredients intended for oral topical delivery for solely therapeutic purposes are included within the class of dental prophylactic ingredients for the purposes of this disclosure.

This disclosure does not purport to list all agents having oral activity that could be effectively delivered to the oral cavity of a target animal by way of the animal chews described herein. A skilled artisan can identify agents beyond those explicitly identified herein that can be effectively delivered using the animal chews.

Breath Agents

Instead of, or in addition to dental prophylactic ingredients, the animal chew described herein can be used to administer a breath agent to a target animal. Animals such as dogs frequently exhibit odiferous breath, attributable to a variety of causes, including poor dental hygiene, ingestion (and/or regurgitation) of foul-smelling compositions, and colonization by microorganisms that produce undesirable odors. The tooth-cleaning ingredients and actions of the animal chews described herein can mitigate odors attributable to dental hygiene issues, but may not mitigate other causes. Inclusion of one or more breath agents can address those causes.

Breath agents can be any of at least three types: perfumes, deodorants, and antimicrobial agents. Perfumes are scent-masking agents that obscure the presence of a disagreeable odor. Selection of a suitable perfume should take into account the odor sensitivity of the individual from whom the odor is to be obscured (e.g., typically a dog's care-giver, rather than a dog), Deodorants are compounds which capture or degrade compounds which are detectable as odors. Antimicrobial agents, by contrast, kill, inactivate, or modify the activities of microorganisms that generate odor-causing compounds. Each of these types of breath agent and their use for improving breath scent is known in the art.

Examples of suitable breath agents include plants shredded mint or oregano leaves), plant extracts (e.g., mint or citrus oils, herbs such as spearmint, parsley, or parsley oil, chlorophyll, or a green tea extract), bicarbonate salts (e.g., baking soda), disinfectants menthol), and combinations of these. Other agents known to improve or mitigate undesirable breath odors can also be used.

As with other components of the animal chew, breath agents should be selected and used in amounts consistent with the other parameters of the chews set forth herein (e.g., hardness, ductility, and resilience of the chewable matrix and suitability of the agents for ingestion by the target animal). Because breath agents tend to be used in relatively small amounts, these considerations are often minor, and are in any event within the ken of a skilled artisan in this field.

Pharmaceutical Agents

Instead of, or in addition to dental prophylactic ingredients and breath agents, the animal chew described herein can be used to administer a veterinary pharmaceutical agent to a target animal. Inclusion of topically-applied pharmaceutical agents on or in the animal chew is discussed elsewhere in this disclosure. However, the pharmaceutical agents that can be effectively administered to the target animal are not limited to those intended for topical oral activity. Consumable portions of the animal chew and oral fluids which contact any portion of the animal chew are swallowed by the target animal. As a result, any veterinary agent that is present in these materials is delivered to the tract of the target animal.

Veterinary pharmaceutical agents that can be administered using the animal chew described herein include those intended for topical administration to a GI tract locus proximal to the stomach (e.g., the esophagus). Such agents also include pharmaceutical agents intended for systemic administration by way of absorption through mucosa of the GI tract, such as in the stomach, the intestines, or the bowel of the target animal.

Administration of a veterinary pharmaceutical agent using the animal chew described herein can be particularly beneficial when an extended period of agent administration is desired, Utile agent is dispersed throughout a resilient portion of the animal chew (e.g., the chewable matrix), the agent will be delivered to the target animal's tract only as that resilient portion is ingested. Because the resilience of the animal chew (especially including its chewable matrix) is selectable as described herein, the rate at which a pharmaceutical agent carried in the resilient portion of the chew wilt be administered to a target animal is likewise selectable. The animal chew described herein can thus be used as an extended-delivery drug delivery device for dogs and other animals having a tendency to chew.

The identity of veterinary pharmaceutical agent(s) included in the animal chew is not critical. Agents that are soluble in one or more components of the chewable matrix and which can withstand the melt-processing techniques described herein are preferred, because they can be incorporated into the chewable matrix to yield a chew that delivers the agent over an extended period at a rate limited by the rate at which the chewable matrix is consumed by the target animal. Veterinary pharmaceutical agents can also be applied to the surface of the animal chew in substantially the same ways such agents can be applied to the surface of other objects (e.g., rawhide animal chews).

Taste-Masking Agents

The animal chew described herein is intended to be a highly palatable article that a target animal will desire to masticate. The presence on or in the chew (e.g., as a component of the chewable matrix thereof) of one or more compounds having an undesirable flavor or odor can diminish the palatability of the article. If such a compound is a desired component of the chew, a taste-masking ingredient can be included in an amount sufficient to render the chewable matrix palatable to the animal. Numerous taste-masking compounds and techniques are known in the art, and substantially any of those can be used, so long as they are consistent with the other parameters of the animal chew described herein. By way of example, a taste-masking compound that is highly appetizing to the target animal can overwhelm an undesirable taste imparted by another component of the animal chew. Likewise, encapsulation of the compound having an undesirable taste (e.g., a veterinary pharmaceutical agent intended for systemic delivery) in a material such as polymeric microspheres that does not substantially release the bad-tasting compound in the oral cavity, but does release it in a higher-pH environment such as the stomach, can be employed to mask an undesirable taste of a component.

Chew Time

An important characteristic of the animal chews described herein is the cumulative period of time that a target animal must masticate upon the chewable matrix of the chew in order to completely consume it.

The chew time of an animal chew depends on several factors, including at least the characteristics of the target animal, the composition of the chewable matrix, the size and shape of the chewable matrix, and the geometry of the animal chew (to the extent that the geometry may restrict access of the target animal to the chewable matrix). Other factors e.g., temperature and humidity) may also affect the chew time of the chew, but these factors will tend to be relatively minor under conditions of normal use of the chews, and can be assumed to be approximately equal to ambient indoor conditions in a temperature-controlled residential room at 20 degrees Celsius and 75 percent relative humidity at sea level for the purposes of this disclosure.

Although the characteristics of individual animals will be expected to vary among any group of target animals, artisans in the field of animal chew products routinely identify rough classes of animals. The animal chews described herein can be designed to exhibit an approximate characteristic chew time for rough classes of target animals. Although 'chewing tenacity and strength' ("chew tenacity") is not a common criterion for classification of animals, other physical characteristics, such as body weight or height, can be used as an approximate correlate of this criterion. Other characteristics, such as state of health or vigor, age, and satiety can affect the chewing behavior of an individual target animal at any given point in time. Despite these individual differences, artisans in this field nonetheless are able to roughly classify animals into arbitrary groupings for the purpose of identifying animals having roughly similar chewing properties. The characteristic(s) used to classify target animals are not critical, but should generally be selected to roughly correlate with chew tenacity.

By way of example, dogs are a highly diverse species of animal with numerous recognized breeds of varying sizes and physiques. Nonetheless, dog breeds and individual dogs are commonly classified as "small" (not more than 15 pounds ordinary body weight), "medium" (more than 15, but not more than 35 pounds ordinary body weight), and "large" (more than 35 pounds ordinary body weight) dogs. Alternatively, dogs (and horses) can be characterized by their height-at-withers (withers being the ridge between the animal's shoulder blades), with "small" dogs being characterized as those having a height at withers of not more than 15 inches, "medium" dogs being those having a height at withers of more than 15 inches, but not more than 25 inches, and "large" dogs being those having a height at withers of more than 25 inches. Large dogs will generally consume an animal chew more quickly than a medium dog will consume the same chew, and the medium dog will generally consume the animal chew more quickly than a small dog. Put another way, the chew tenacity of large dogs is greater than that of medium dogs and greater still than that of small dogs.

For illustrative purposes in this disclosure, dogs will be classified as small, medium, or large based on the foregoing ordinary body weight criteria, with ordinary body weight being the average weight of a healthy dog over the course of a week.

Compositions for the chewable matrix of the animal chew described herein as well as the geomarical shape of the chew is described elsewhere in this disclosure. If these two factors which affect chew time are held constant, the two remaining primary variables that can affect chew time are size of the chew and characteristics of the animal. If size of the chew is also held constant, it is apparent that a large dog will consume the chew more quickly than a medium dog, which will, in turn, consume it more quickly than a small dog. If animal chews of a given shape and composition and having roughly equal chew time for the three types of dogs are desired, then the size of the chew must be varied for the three classes of dogs. Thus, an animal chew having a chew time of about 5-10 minutes for a large dog will be larger than an equivalently-shaped and -formulated animal chew having the same chew time for a medium dog, and both of these will be larger than an equivalently-shaped and -formulated animal chew having the same chew time for a small dog. This explanation demonstrates that for a given animal chew formulation and shape, the size of the chew should vary in proportion to a classification of an animal chew tenacity if the chew time of the animal chew is to be approximately equal across the classification.

For dogs, animal chews having a variety of chew times can be made, the chew time depending on the purpose for which the animal chew will be used. For animal chews provided for the purpose of rewarding dog behavior or relieving teething or chewing urge, a chew time of 1-30 minutes can be desirable, with a chew time of about 1-2 minutes or about 2-5 minutes for all classes of dogs being suitable examples. For animal chews provided for the purpose of cleaning dog teeth, a chew time of 10-30 minutes can be desirable. For animal chews provided for the purpose of delivering an active agent over an extended period, the chew time should be approximately equal to that extended period. If the same animal chew formulation is to be used for each of these purposes for all dog classes, then the corresponding animal chew can vary in size. If the same size animal chew is to be used for each of these purposes for all dog classes, then the composition of animal chew can be varied.

The chew time of animal chews intended for dogs should preferably not exceed the attention span of a target dog. By way of example, the animal chew should be completely consumable by the dog within several minutes, such as within about 5, 2, or one minute.

Shape of the Animal Chew

A significant feature of at least one embodiment of the animal chew described herein is its geometric shape, which is selected to enhance the dental cleaning efficacy of the chew. In particular, there are several features of the geometric shape which enhance its dental cleaning efficacy. First, it includes numerous nubs and ridges, preferably over most or substantially all of the surface of the chew. Second, it can have a generally curved shape to prevent it from lying flat on a flat surface (and thereby enhancing the ability of a target animal to pick up the chew from a flat surface for chewing). Third, the chew can have a twisted shape that tends to orient nubs, ridges, edges, or other parts of the chew in a manner that enhances tooth-to-chew contact (the chew can, of course, have both a generally curved shape and a twisted shape, such as the chew illustrated in FIG. 1). Fourth, the chew has a shape that facilitates its production from a molten mass, such as in a rotary or plate mold. The shape of the chew is also relatively compact and lacks sharp edges, both of which reduce the likelihood of damage to the chew during packaging, storage, transportation, storage, and retail sale. Optionally, the chew can have a cavity or hollow which can be empty or which another material can occupy. The chew can also have an overall shape that is pleasing to the target animal or a care-giver of the target animal.

The shape of the chew includes multiple nubs and ridges on its surface. When chewed by a target animal, these nubs and ridges tend to contact the teeth and gums of the target animal at surfaces proximal to the tips of the teeth. Compared with chewing a flat slab of material, chewing of the relatively rough or ridged surface of the chew tends to result in a fuller extent of contact between all areas of the target animal's teeth. The nubs and ridges are preferably disposed and spaced in configurations that accommodate teeth of the target animal between the nubs and ridges, so that biting upon the chew will tend to urge the apices of the nubs and the crests of the ridges toward the roots the animal's teeth and toward its gums as the teeth slide into the spaces between the nubs and ridges. Thus, for target animals having small, relatively closely-spaced teeth, animal chews having relatively closely-spaced nubs and ridges will tend to scour the target animal's teeth more thoroughly than an equivalent chew having more broadly-spaced nubs and ridges. Conversely, an animal chew having relatively broadly-spaced nubs and ridges can effectively scour (i.e., contact and abrade a greater proportion of the tooth surfaces of a target animal having similarly broadly-spaced teeth.

The heights of nubs and ridges on the animal chew are preferably comparable to (i.e., on the order of the same size as, or 10%, 25%, or 50% of) the length that at least some teeth of the target animal extend beyond the gum. Nubs and ridges having these heights are able to abrade teeth near their tips and along a substantial portion of the perimeter faces of these teeth, toward the gum line.

In one embodiment, the animal chew has nubs, ridges, or both, substantially covering the surface of the chew, including at least part of two opposed, substantially parallel faces thereof and part of the intervening transitional surface that extends between the two opposed faces. The nubs and ridges can cover substantially the entirety of each surface of the chew (e.g., as shown in FIG. 1). By way of example, substantially the entirety of each of the two opposed faces can be covered with nubs, and substantially the entire intervening transitional surface 40 can be covered with ridges that extend between the two opposed faces (e.g., as shown in FIG. 6). Such a chew can be relatively easily extricated from a mold formed by two plates that meet at parting line 42, the mold plates each having a cavity corresponding to the shape of half of the chew, since the ridges will tend to slide out of the mold plate cavities as the chew is removed therefrom. By contrast, if the chew had one or more nubs extending outwardly from its transitional surface 40, such nubs could interlock with the corresponding portion of the mold cavity and prevent or inhibit release of the chew from the cavity.

Figure 23F:
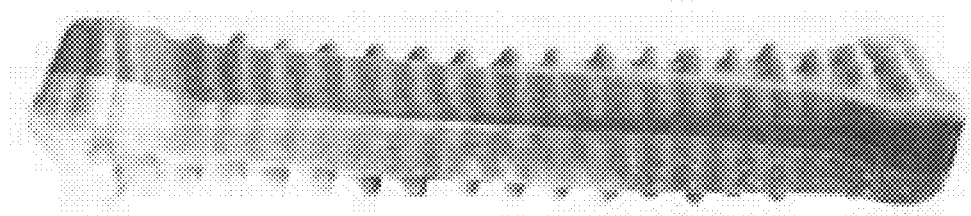
FIG. 23 consists of FIGS. 23A, 23B, 23C, 23D, 23E, 23F, 23G, 23H, and 23J (No figure is designated 231). Each of these figures is an image of an embodiment of the animal chews described herein, with the chew shown in FIG. 23E being broken along its shaft to illustrate that the interior of the chew has a composition visually different from its exterior.
Figure 23G:
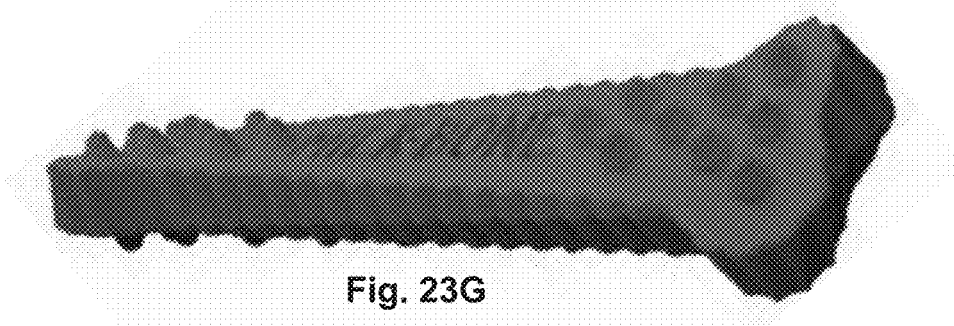
Figure 23H:
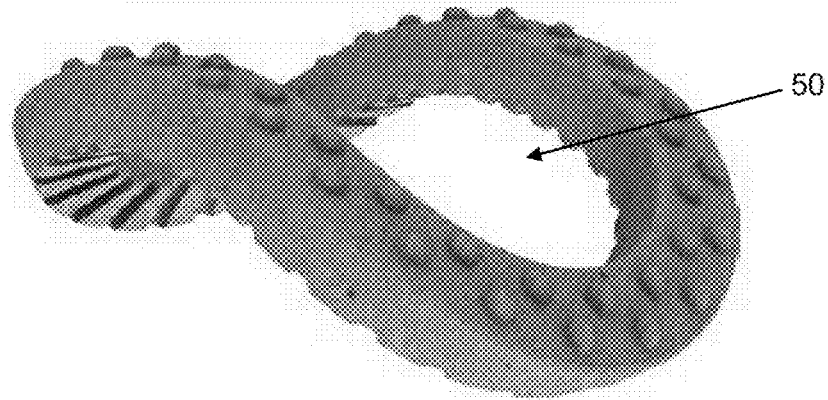
Figure 26C:
FIG. 26 consists of FIGS. 26A, 26B, 26C, 26D, 26E, 26F, 26G, and 26H and depicts a variety of shapes in which the animal chews described herein can be formed.
Figure 26F:
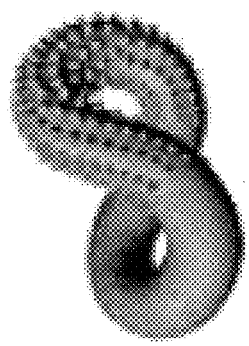
Figure 26B:
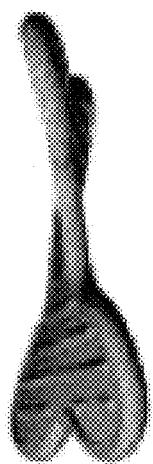
Figure 26E:
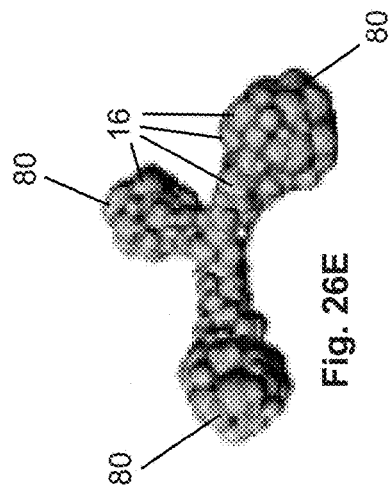
Figure 26H:
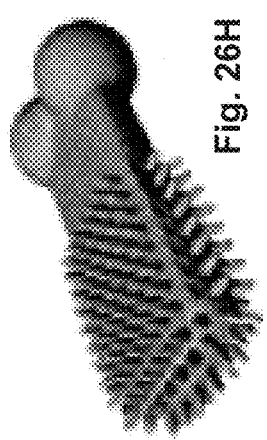
Figure 26A:
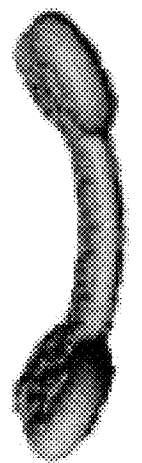
Figure 26D:
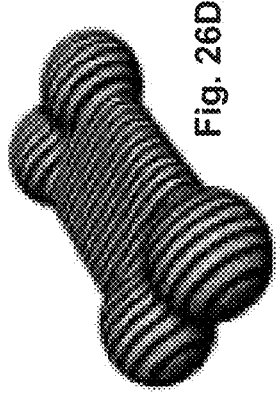

The nubs 12 can have a variety of shapes, but tend to extend generally away from the surface of the chew from which they arise, generally in a direction perpendicular to that surface. Nubs can have substantially any three-dimensional geometric shape, such as conical, frusto-conical, rounded, or domed. The nubs can be relatively sharp (i.e., have an acute apex, rounded or not) as shown in FIG. 12, more rounded and blunt as show in FIG. 5, be approximately hemispherical as shown in FIG. 23H, or even be more nearly globular as shown in FIG. 26E (in which instance the nubs may be indistinguishable from bulges 16 on the chew). The number of nubs disposed on a surface of the pet treats is not critical, nor is their patter or layout. Nubs 12 on a surface can be of substantially uniform size as shown in FIG. 25A, of alternating sizes as shown in FIG. 25B, or of a, variety of sizes.

Figures 24A, 24B, 24C, 24D:
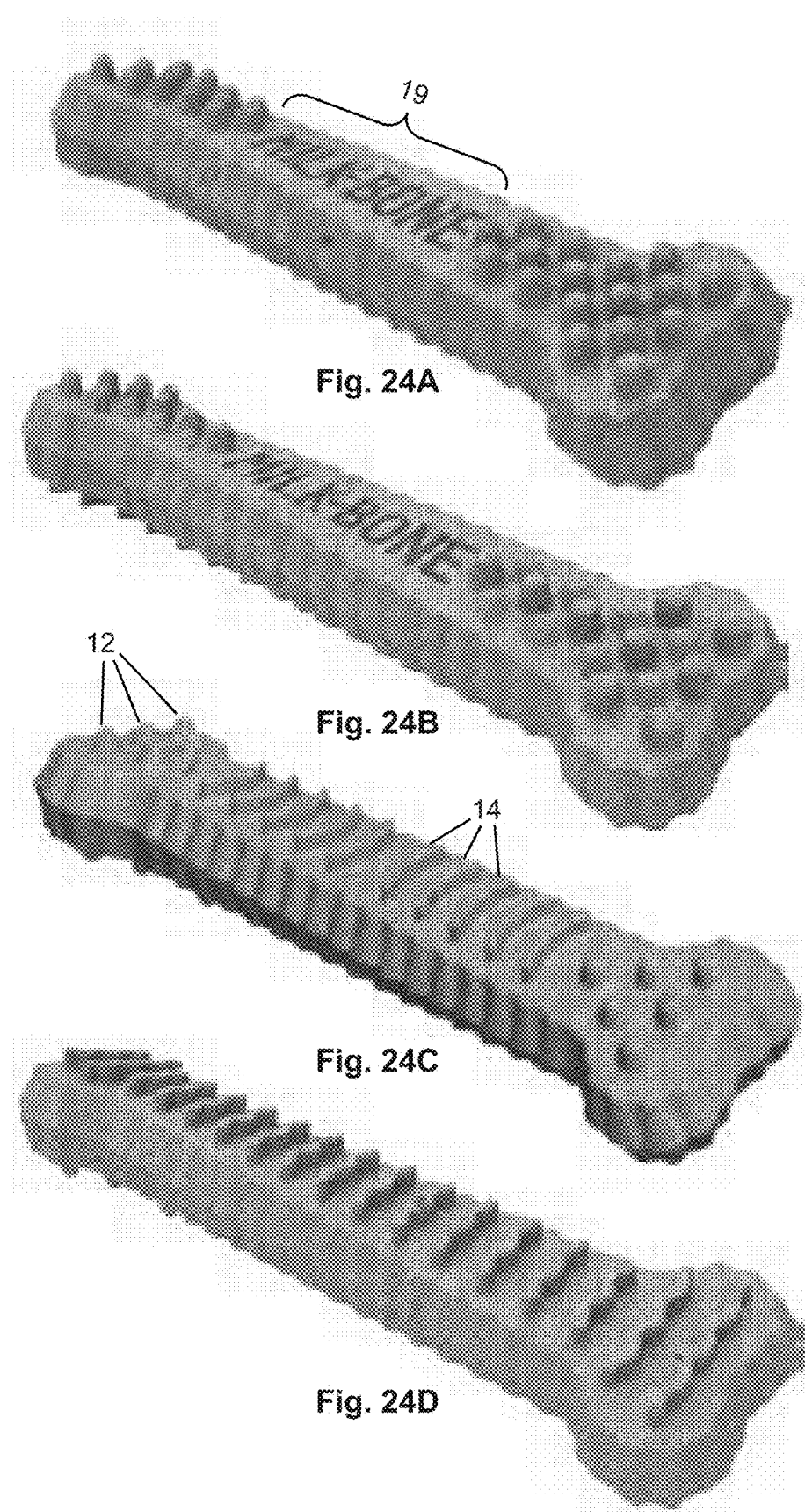
FIG. 24 consists of FIGS. 24A, 24B, 24C, and 24D. Each of these figures is an image that depicts surface features of embodiments of chews described herein. Each of the embodiments has a "twisted dog-bone" shape, which consists of a shaft having a pair of bicondyfic ends, the bicondylic ends of each chew being angularly offset from one another. In the embodiments shown in FIGS. 24A and 24B, text (here, the MILK-BONE registered trademark of Del Monte Corporation, San Francisco Calif.) is molded into the surface of the chew. The embodiment shown in FIG. 24A has rounded conical nubs extending from the front and rear surfaces thereof. The embodiment shown in FIG. 24B has rounded conical nubs extending from the front surface thereof and ridges extending from the rear surface thereof. The embodiment shown in FIG. 24C has both rounded conical nubs and ridges extending from the front and rear surfaces thereof. The embodiment shown in FIG. 24D has ridges extending from the front and rear surfaces thereof.

The shape(s) of ridges 14 present on one or more surfaces of the animal chew are similarly not critical, and an animal chew may include two or more ridges of varying shape, size, direction, and height. By way of example, ridges 14 can extend straight across a surface, such as the ridges 14 having a rounded profile that extend completely across the transitional surface 40 of the chew depicted in FIG. 3. Ridge crests truly also be curved as shown in FIG. 24C or rippled, as shown in FIG. 25C.

As the animal chew is masticated and consumed by the target animal, the chew will tend to crumble and its surface will frequently develop a more irregular shape than its initial shape. This can be beneficial, in that the increasingly-irregular shape can be better able to contact relatively remote tooth surfaces within the mouth of the target animal and improve the dental cleaning efficacy of the chew. Furthermore, degradation of the chew upon mastication can also cause its shape to more nearly approximate the contours of the dentition of the individual target animal, further improving its dental cleaning efficacy.

Figure 17:
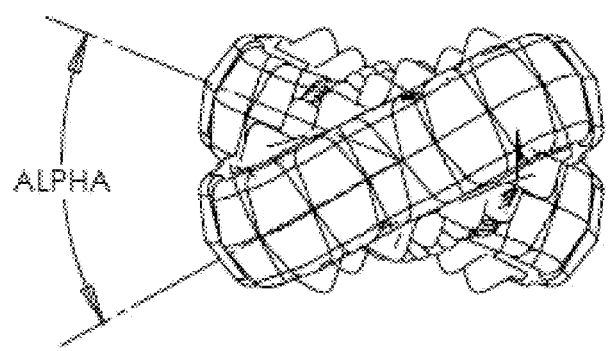
FIG. 17 is an end view of an animal chew as described herein, the chew having a colloquial dog-bone shape in which planes taken through each of the bicondylic ends and intersecting one another along the axis of the shaft are offset from one another by the angle identified in this figure as "ALPHA,"
Figure 18:
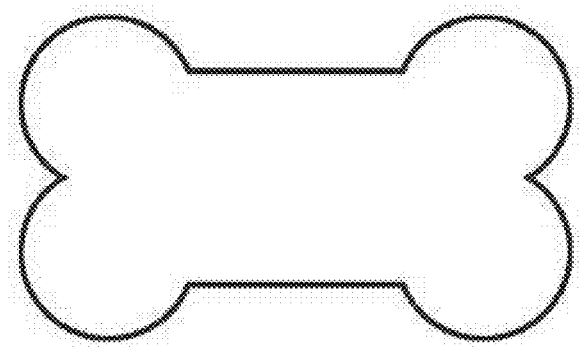
FIG. 18 is an illustration of a colloquial dog-bone shape, which consists of a shaft having a pair of bicondytic ends.

The animal chew can have a generally curved shape as shown in FIGS. 5 and 23H, an axially twisted shape as shown in FIGS. 7, 17, and 27H (i.e., a chew having ends that are rotationally offset from one another about the axis of the shaft, with a degree of axial twist equal to angle alpha is shown in FIG. 17), both as shown in FIG. 3, or neither as shown in FIG. 6. An animal chew having a generally curved shape will not lie against a flat surface with either of its opposed surfaces flush against the flat surface. This feature facilitates grasping of the animal chew by a target animal when the chew rests upon a flat surface. An animal chew having an axially twisted shape will also not lie against a flat surface with either of its opposed surfaces flush against the flat surface and likewise facilitates grasping of the animal chew by a target animal when the chew rests upon a flat surface.

The curved and twisted shapes of the animal chew can result in orientation of nubs and ridges (and corresponding surfaces of the chew from which they extend) at a variety of angles relative to an end 80 of the chew, so that when a target animal grasps the chew at its end (e.g., a dog holding an end between its front paws while gnawing on the opposite end of the chew) nubs and ridges will extend from the opposite end of the chew at a variety of angles and will engage the target animal's teeth at a variety of angles when the animal masticates the chew. The orientation of the chew ends and the nubs and ridges, as well as the animal's efforts to gnaw the chew from various angles, will cause a greater proportion of the surface area of the animal's teeth to be scoured by the chew than if the chew were straight and had nubs and ridges extending therefrom in a more limited number of directions. Thus, the overall-curved and axially-twisted shape of the chew can enhance the dental cleaning efficacy of the chew.

An important aspect of the shape of the animal chew described herein is that the shape can facilitates production of the chew by various methods described herein.

For embodiments in which the chew has two opposed faces substantially parallel to one another (whether or not the opposed faces are planar or curved) and ridges having a substantially uniform profile along their length extend between the two opposed faces about the transitional face of the chew (see, e.g., FIGS. 1-5), the chew can be formed by cutting a slab of chewable matrix in the direction perpendicular to the opposed faces (e.g., using a die having the shape of the perimeter of the opposed faces). The uniformity of the transitional face between the opposed faces in the direction perpendicular to those faces facilitates numerous methods of forming the chew. By way of example, the slab can be cut prior to or as a part of the same molding operation that imparts a texture (e.g., a nub-covered surface) to one or both of the opposed fixes.

For embodiments in which the chew is symmetrical about a plane of symmetry that is twisted by an angle alpha (see FIG. 17, alpha being between −90 and +90 degrees, preferably being between −45 and 45 degrees) along the long axis of the chew (see, e.g., FIGS. 6-16), the chew can be formed between two mold plates, each plate having a cavity that accommodates a portion of the chew including one of the two opposed faces. So tong as the transitional face 40 does not include a portion that extends outwardly therefrom at a position distal (within the mold cavity) to the parting line 42 formed at the interface of the two mold plates, the molded chew can be lifted from the mold cavity without twisting the chew. That is, because the transitional face of the chew the face that contacts the lateral sides of the mold cavities is smooth (even if it is ridged, scalloped, or fluted; see FIG. 31), the chew can be lifted from the cavity perpendicularly to its depth and the margins of the chew so lifted will not impinge upon the lateral sides of the mold cavity. The ease with which the molded chew can be removed from the mold cavity when it has this shape facilitates its manufacture by a variety of molding processes, as described herein.

Similarly, nubs and ridges extending from the opposed faces of the chew are oriented at angles such that the nubs and ridges formed upon molding the chew do not impinge upon the surface of the mold cavity when the molded chew is lifted from the cavity perpendicularly to its depth.

Fabrication of the animal chews and improved resistance to chipping can be conferred by including a chamfer 44 at edges where surfaces would otherwise meet at a sharp (e.g., >45 degree) angle. By way of example, the animal chew depicted in FIG. 32 has a shape that includes a chamfer extending about the perimeter of the visible opposed face (which bears nubs) where it meets the fluted transitional face of the chew.

The animal chew can have a shape that defines a cavity 50 or hollow that is bounded by the body 10 of the chew. The cavity can be left empty (i.e., a void within the body) as shown in FIGS. 23H, 26F, 27D, and 27E-27H, Alternatively, the cavity can have a filling 55 therein, filling a portion or all of the cavity as shown in FIGS. 1-5 and 27A.

Figure 26G:
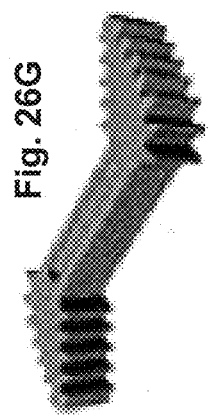

The overall shape of the animal chew is not critical, and preferably is a shape that is pleasing to the target animal or to a care-giver of the target animal. The overall shape need not have any particular relation to the efficacy of the animal chew for any purpose, and can instead be ornamental, whimsical, or selected to evoke another object. By way of example, for animal chews intended for dogs, the chew can have an overall perimeter shape evocative of a generic "bone" (see FIG. 8), it being commonly known that dogs generally favor chewing upon bones. Other overall shapes can be selected, such as rings and loops (FIGS. 23H 26F), rods and sticks (FIGS. 29B, 29C, and 30), toothbrush-like shapes (FIGS. 26G, 28B, and 28F), analogs of cut bones or meats (FIGS. 28A-28E), disks (FIG. 29A), abstract shapes (FIG. 26E), and combinations of these (FIGS. 26A, 26B, 26F, 26H, 27F-27H, FIGS. 28A-28F, and FIG. 3)

An animal chew having the overall perimeter shape of a generic "bone" (see, e.g., FIG. 1C) includes an elongate shaft 70 with two ends 80, each end including one or more condyles 82 (or, more properly one or more shaped parts resembling the condyle of a bone such as a bovine femur). Such a bone-shaped animal chew can be twisted about its long axis, as shown for example in FIG. 7, although it need not be so twisted (compare, e.g., FIGS. 6 and 7). A bone-shaped animal chew can also have a general curved shape, as shown in FIG. 5, wherein the long axis of the chew is curved in the direction of one (a "C"-shaped curved shape) or both (an "S"-shaped curved shape) of the opposed surfaces of the chew, regardless of whether the chew is also twisted about its long axis. The chew illustrated in FIG. 5, for example, exhibits a C-shaped curved shape and is not twisted about its long axis and has bi-lobed condyle-like shapes at both of its ends.

The opposed faces 20 and 30 of the animal chew are preferably approximately parallel to on another across the surfaces of both faces, but they need not be. As shown for example in FIGS. 26C, 26F, 27G, 27H, and 28A-28F, some or all of the opposed faces may be rounded and not parallel to one another, or even a opposed portions of a single rounded face (see, e.g., FIGS. 26E and 26F).

Many animal chews of the type described herein will have opposed first and second surfaces 20 and 30, the opposed surfaces being relatively large relative to the breadth of the transitional face 40 that extends between the opposed surfaces. However, this need not be so. FIG. 30 depicts several embodiments of the animal chew in which the breadth of the transitional face 40 significantly exceeds the size of the two opposed faces 20 and 30. Comparing FIGS. 1 and 30F, it can be seen that the filling 55, when present can be of relatively small size relative to the sizes of the opposed faces (as in FIG. 1), and can be substantially equal in thickness to the breadth of the transitional face 40. However, the size of the filling can substantially exceed the size of both the opposed faces 20 and 30 and the thickness of the transitional face 40, as shown in FIG. 30F.

The animal chew shapes illustrated and described herein are merely illustrative. Animal chews made from the materials described herein, using the processes described herein, having the properties described herein, or a combination of these, can be made in substantially any shape consistent with the parameters set forth herein.

Appearance of the Animal Chew

Apart from their shape, animal chews described herein can have a wide variety of distinct visual appearances. The chews can, for example be made in a variety of colors by adding colorants to the chewable matrix thereof, as shown for example in FIG. 23.

The chew shown in FIG. 23A includes three portions a first portion 22, a second portion 32, and an intermediate portion 52. In this figure, first and second portions 22 and 32 have the same light brown color (regardless of whether they are made from the same chewable matrix material). The intermediate portion 52 has a contrasting blue-green color. Apart from the colorants contained therein, each of the first, second, and intermediate portions 22, 32, and 52 can have the same chewable matrix formulation, or they each can have a distinct formulation.

Similarly in FIG. 23B, the chew portrayed consists of a chewable matrix having first and second portions 22 and 32 that are distinguishable by their color. Apart from the colorants contained therein, the first and second portions 22 and 32 can have the same or different formulations.

Figure 23J:
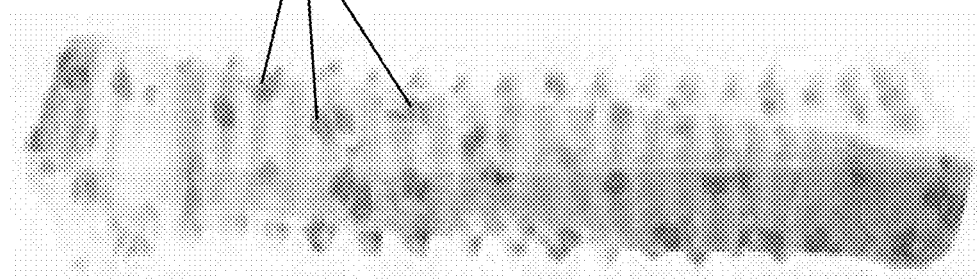

It can be beneficial to use color as an indicator of the type or content of a chewable matrix or another portion of the animal chew. Especially when multiple animal chews are made having similar sizes and shapes, but different formulations, such color coding can aid a target animal's care-giver (or the target animal itself, to the extent the colors can be distinguished by the animal) to differentiate between the different animal chew formulations. Furthermore, the colors selected for chewable matrices having specialized formulations can be evocative of the active agent contained therein. By way of example, chewable matrices containing mint or another breath agent can be colored blue or green, to evoke association with the green of mint plants or the blue color frequently associated with breath-freshening products intended for use in human oral care. White coloration, as shown in FIGS. 23F and 23J can evoke association with tooth-cleaning products, such as human toothpastes and other dentifrices. Red coloration, as shown in FIG. 23G can evoke association with a rubbery material that is not intended for consumption (and, indeed, FIG. 23G is an image of an animal chew of the type described herein that includes no chewable matrix, but is instead constructed of a non-digestible rubbery polymeric material that is substantially resistant to destruction by ordinary chewing action by a dog). Brown coloration (i.e., the color of many prior art consumable dog treats) can evoke a grain- or meat-flavored material and can be used to indicate chewable matrices intended primarily for consumption by an animal. Combinations (see, e.g., FIGS. 23B, 23C, and 23F) of colored matrices can indicate multiple functionalities of animal chews (e.g., consumability and breath-freshening action for the chew depicted in FIG. 23B, breath-freshening and tooth-cleaning actions for the chew depicted in FIG. 23C, and consumability and breath-freshening and tooth-cleaning actions for the chew depicted in FIG. 23F). Coloration of the animal chew or portions thereof (e.g., a whitish exterior portion surrounding a reddish central portion so as to resemble a cut of meat or a natural bone) can be selected to appeal to an animal, to the owner of an animal (i.e., one who purchases the chew for another animal), or both.

Chewable matrices are not the only animal chew components that can be colored to indicate or evoke their functionality. Other portions of chews can be color coded, such as non-consumable portions (red in FIG. 23G), and functional inclusions incorporated as visible particles. For example, visible white particles which indicate or evoke tooth-cleaning functionality can be seen in the consumable brown chew depicted in FIG. 23D. Similarly, breath-freshening functionality is indicated or evoked by the visible blue inclusions 18 that are visible in the white-colored (evocative of breath-freshening and tooth-cleaning activity) chew depicted in FIG. 23J. Likewise, blue and white coloration (evocative of tooth-cleaning functionalities) are visible in the filling 55 that can be seen within the cavity in the cut-open animal chew depicted in FIG. 23E.

In addition to surface shapes such as the nubs, ridges, scalloped or fluted edges, and the overall shapes described herein, the animal chew can have other shapes, such as for ornamental or functional purposes. Many animal chews formed between two matching mold plates as described herein will exhibit a parting line 42, as highlighted in FIG. 7 and as is visible in each figure that makes up FIG. 23 (except FIG. 23H, in which the parting line is difficult to distinguish). The animal chews can include prominent text or other indicia imprinted into, or disposed upon the chew (such as on or in the chewable matrix thereof). By way of example, text 19 depicting the registered trademark MILK-BONE is visible imprinted into the chews depicted in FIGS. 23E, 23G, 24A, and 24B.

The animal chews can include multiple chewable matrices that are linked or connected to one another by a non-consumable portion, such as by a rope or indigestible plastic rod or ring.

In one embodiment, a chew-resistant, non-consumable portion of the animal chew includes an orifice or recess adapted to securely fit around an end of the chewable matrix so that the chewable matrix can be gnawed upon by the target animal and chewed back to the perimeter of the non-consumable portion. So long as the portion of the chewable matrix cannot be extricated from the non-consumable portion by the target animal, the non-chewed portion of the chewable matrix (e.g., a relatively small fragment that remains after the bulk of the chewable matrix has been consumed by the target animal can remain unavailable to the target animal for further consumption. By sequestering the last non-consumed fragment of the chewable matrix, the non-consumable portion can prevent the target animal from swallowing the fragment. The chewable matrix and the non-consumable portion may each have a complementary whimsical shape, such as a toothbrush-shaped chewable matrix having a 'handle' portion that fits snugly within a 'handle' shaped recess in a non-consumable portion made from rubber or chew-resistant plastic and having the shape of a human hand, a dog paw, a representation of a dentist, or the like. The non-consumable portion can also serve as a convenient grip by means of which the target animal can hold the chewable matrix in a relatively fixed position while gnawing upon it.

The chew can be partially or completely coated with an edible material. It can also be partially or completely embedded in a shaped piece of such a material. By way of example, a chew described herein can have a flavored coating sprayed or adhered to most or all of its surface, so that the flavored coating readily induces mastication of the chew by a target animal to release the coating, followed by more sustained chewing upon the chew itself. Similarly by way of example, a chew described herein can be embedded in an easily-eaten matrix, such as a material akin to dog kibble, with the easily-eaten matrix having the shape of a beefsteak or a chicken leg and the chew having the appearance of a bone, some or all of which is revealed upon consumption of the easily-eaten matrix by the animal.

Uses for the Animal Chew

A significant advantage of the animal chews described herein is the ease with which they can be used to achieve their ends, relative to the difficulty of achieving those same ends by other methods.

Previous methods for cleaning the teeth in the animal typically involve brushing or scraping the teeth of the animal with an oral care instrument, such as a toothbrush, scaler, or curette. Such tooth-cleaning methods are often poorly tolerated by animals and are time-consuming and technically difficult to perform even upon a cooperative animal.

When an animal chew as described herein contains a dental prophylactic ingredient (e.g., an anti-tartar agent, an abrasive, or a tooth-strengthening ingredient), prophylactic veterinary dental care can be performed substantially more easily—as easily as selecting an animal chew having an appropriate dental care ingredient in an appropriate amount and providing the animal chew to the target animal. Owing to the appetizing characteristics of the animal chew, the target animal will voluntarily gnaw upon the chew, thereby effecting the desired dental cleaning. The process can be repeated substantially as often as desired.

Previous methods for administering a veterinary pharmaceutical composition to an animal involve delivering the composition to the appropriate body location in a reliable, observable manner. By way of example, topically-delivered compositions are delivered directly to the topical site at which pharmaceutical action is delivered and, if necessary, the animal is prevented from dislodging the medicament through rubbing, licking, or irrigation of the treated site. Particularly when the desired delivery site is within the oral cavity of an animal, preventing the animal from dislodging medication from the application site can be challenging and may require anesthesia of the animal. Systemically-intended compositions delivered by an oral route involve reliably inserting a dosage form into the GI tract of the animal and observing whether or not the animal regurgitates, sequesters (e.g., in a mouth cheek), or otherwise avoids passage of the dosage form to the GI tract.

When an animal chew as described herein is used to administer a veterinary pharmaceutical composition to a target animal, the composition is incorporated into an appropriate part of the chew, and the chew is simply given to the target animal. Owing to the appetizing characteristics of the animal chew, the target animal will voluntarily gnaw upon the chew, thereby effecting delivery of the active agent. The process can be repeated substantially as often as desired, and the dosage administered can be controlled by selecting the amount of the composition incorporated into the animal chew.

Previous methods for delivering nutrients (e.g., calories, vitamins, minerals, or agents active promoting health and favorable appearance of skin or coat) to an animal involve incorporating the nutrients into a food that the animal will voluntarily consume. Alternatively, the nutrients can be incorporated into a dosage form and administered like a veterinary pharmaceutical composition, with the attendant problems discussed herein.

As with tooth-cleaning compositions and pharmaceutical agents, when an animal chew as described herein is used to deliver nutrients to a target animal, the nutrients can simply be incorporated into the chew (together with a taste-masking agent, if necessary), and the chew can be given to the target animal.

The animal chews described herein can, of course, simply be fed to target animals as treats or foodstuffs, just as previously known foodstuffs and treats can be. Provision of treats or foodstuffs to an animal by its care-giver can enhance the emotional bond between the two.

Target animals for which animal chews described herein are believed to be particularly appropriate include animals that tend to enjoy chewing on articles, such as dogs, horses, rodents, and ruminant animals. The shape selected for the animal chew should be chosen based on the preferences of the target animal for which it is intended. For example, dogs tend to enjoy chewing on bulky, relatively rigid articles having a shape that fills a substantial fraction of their oral cavity, which is why 'bone-shaped' animal chews are highlighted in this disclosure for use with dogs. Horses, by contrast, tend to enjoy chewing long, thin articles that exhibit rigidity and toughness similar to that of grasses and grains which they frequently select for chewing. Accordingly, animal chews made from materials like those described herein should have straw-like shapes, such as shapes similar to blades of grass or thin-walled tubes. Ruminant animals likewise tend to favor blade- and straw-like chewing substrates.

Manufacturing Processes

A significant feature of the animal chews describe herein is the ease with which they can be manufactured by a variety of processes. Although the details of various manufacturing processes differ substantially, each of these processes essentially involves two steps: first forming a molten mass from the starch, protein, and water components of the chewable matrix of the chew (optionally together with other ingredients), and then shaping the molten mass into the animal chew described herein before the molten mass cools or hardens sufficiently to inhibit or prevent the shaping.

Formation of the molting mass involves two processes, namely combining the components of the mass and heating the mass sufficiently that at least some fraction of the starch therein undergoes gelatinization. The precise methods and order used to perform these processes is not critical. However, what is believed to be important is that a sufficient fraction of the starch undergoes gelatinization that gelatinized starch chains can bind together the components of the mass upon cooling. While not being bound by any particular theory of operation, it is believed that gelatinized starch chains are able to interact with proteins, with denatured and denaturing protein chains, with water, and with other components of the mass. Upon cooling of the mass, interactions between starch chains and other mass components binds the starch and the other components together and to one another, thereby producing a plastic matrix.

It has been discovered that judicious selection of starches, protein, other mass/matrix components and their respective amounts yields matrices that exhibit rheological properties (e.g., rigidity, deformability, integrity, and toughness) such that the matrices are perceived by various animals as desirable for chewing upon.

Advantageously, the components of the chewable matrices described herein (i.e., starches, proteins, and water) are normal components of animal diets. Thus, in addition to encouraging mastication by animals, the chewable matrices described herein tend to be harmless (or even nutritionally beneficial) to the animals which chew upon them.

Another significant advantage of the chewable matrices is that the matrices can be formed in the presence of a wide variety of compounds beyond those needed for matrix formation. Thus, these compounds can be incorporated into the matrix and released therefrom when it is chewed by animals. Such components can be incorporated into the matrix before it is heated above the starch gelatinization temperature, while the matrix is still molten, or while the matrix is solidifying upon cooling (e.g., for temperature-sensitive ingredients). Because starch gelatinization temperatures tend to be relatively moderate (generally below 100 degrees Celsius and sometimes as low as about 55 degrees Celsius, the molten mass can be formed at temperatures and for periods of time that will not significantly degrade many compounds and compositions having beneficial activities.

In one embodiment, all components that will be included in the chewable matrix are combined and thoroughly mixed. After the mixing is substantially complete (i.e., when the mixture is substantially homogenous), the mixture is heated to the processing temperature. The processing temperature is preferably maintained below the boiling point of the mixture (approximately 100 degrees Celsius for pure water, but typically 110 degrees Celsius or higher for the mixtures described herein). At the processing temperature, at least some of the starch (preferably at least about 50% on a weight basis, and more preferably at least about 80%) undergoes gelatinization. The heated mixture is consider molten or a "melt" at this point, and it exhibits sufficient plasticity that it can be shaped.

The melt is delivered to apparatus or processes which confer a shape to the melt, and the melt is cooled sufficiently quickly that the melt retains the conferred shape. Optionally, additional shape features can be conferred to the melt (e.g., twisting of a molded bolus of the melt) after its initial shaping and while it retains at least limited plasticity. Upon cooling to ambient temperature (about 20 degrees Celsius), the melt is no longer substantially plastic and it will retain the shape(s) conferred to it, at least unless it is again brought to a significantly greater temperature. The shaped and cooled bolus of the melt thus becomes the animal chew described herein.

Mixing of components used to form the melt preferably occurs prior to heating the mixture to form the melt. However, one or more of the components can be preheated, the mixture can be heated during mixing, or a combination of these can be performed. Furthermore, one or more components (e.g., heat-sensitive components) can be added to the mixture after heating has begun, after heating of the melt is stopped, or even as the melt is cooling (so long as the melt retains sufficient plasticity to permit mixing of the component therewith).

In one embodiment, most or all dry components (e.g., starches, fibers, particulates, dry vitamins, and colorants) are thoroughly mixed before liquid components are combined with them. Similarly, some or all liquid components of the melt can be mixed prior to combining them with the dry ingredients. Owing to the substantial viscosity of the mixture that is heated to form the melt, it can be beneficial to mix fluids and free-flowing solids prior to forming the mixture that is subjected to heating.

The apparatus(es) used to mix and heat the mixture are not critical, and substantially any equipment capable of achieving such operations can be used. Equipment designed for performing mixing and heating operations on highly viscous materials, such as plastics, can beneficially be used. By way of example, the melt can be prepared by both mixing its components and heating the resulting mixture in any of a wide variety of extruders that are available. Owing to the importance of controlling the temperature of the melt, an extruder that permits control of the materials passing therethrough is especially suitable for forming the melt.

It is beneficial when using an extruder that venting of gases which exhaust from the melt be possible, such as by modulating the atmospheric pressure (or the internal pressure of the extruder barrel) to which the melt is subjected. A variety of extruders having this functionality are known, and substantially any of them that is otherwise compatible with the methods described herein can be used for melt formation. If the temperature of the melt exceeds its boiling point (or the boiling point of a liquid present as a distinct phase within the melt), then vaporization of the liquid can be expected to occur. Such vaporization will induce formation of bubbles or pores through the matrix, decreasing the integrity and increasing the friability of articles formed from the melt. To the extent that these properties of the formed articles fall outside ranges considered desirable for the animal chews described herein, such vaporization should be avoided, such as by venting of gases prior to final melt formation, temperature control of the melt, or a combination of these.

Substantially any method of shaping the melt can be used to yield the animal chews described herein. Several such methods are exemplified in this disclosure. In addition to those specifically exemplified, substantially any known method of conferring a shape to a viscous molten fluid that stiffens as it cools can be used, such as casting in frangible molds or in a compressed particulate bed or injection molding.

After the desired shape of an animal chew has been conferred upon a bolus of melt, the melt should be cooled so that it will retain the shape. If desired, the bolus can also be dried to reduce the water content of the melt material to a desired value (e.g., to about 14 to 18 wt % for most of the compositions described herein). Such cooling and/or drying preferably is performed in a controlled environment, such as a drying oven in which the temperature and humidity of the oven interior can be controlled. When reduction of moisture content is desired, such reduction is preferably performed at a relatively high temperature (e.g., at 165-185° F.) in order to hasten the process. The moisture content of cooled animal chews can be preserved by packaging the chews in moisture-retaining packaging, such as any of a wide variety of plastic films which retard moisture passage across the film. Inclusion of a humectant, such as one or more of those described herein, can also inhibit moisture loss from the finished animal chew. The proportions of water and humectant in the final product should be selected in amounts sufficient to confer chewable plasticity to the cooled chewable matrix.

Figure 20A:
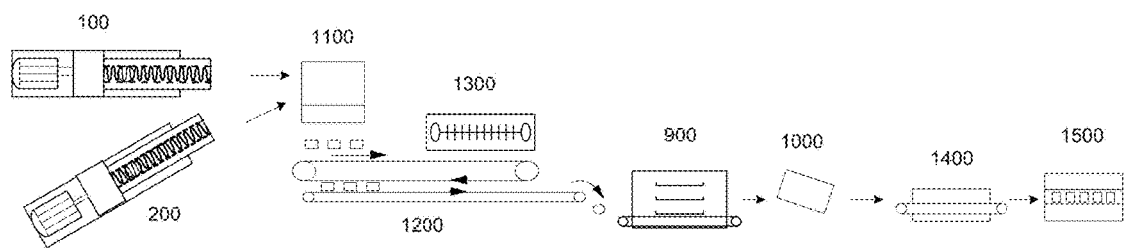
FIG. 20A is a diagram of a billet-forming and molding process for producing animal chews from extruded materials as described herein.
Figure 21A:
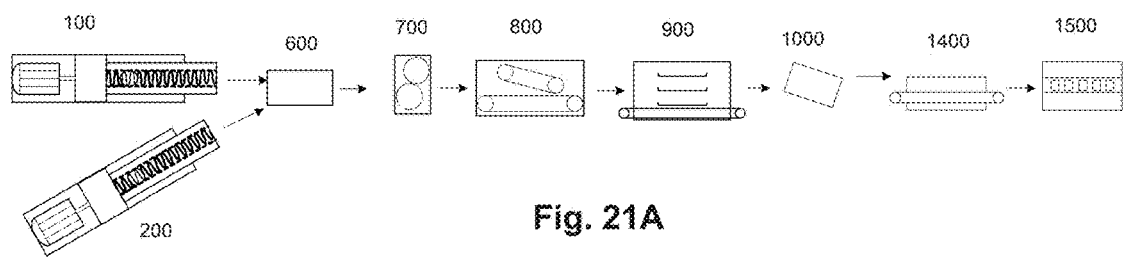
FIG. 21A is a diagram of a roll-molding process for producing animal chews from extruded materials as described herein.
Figure 22A:
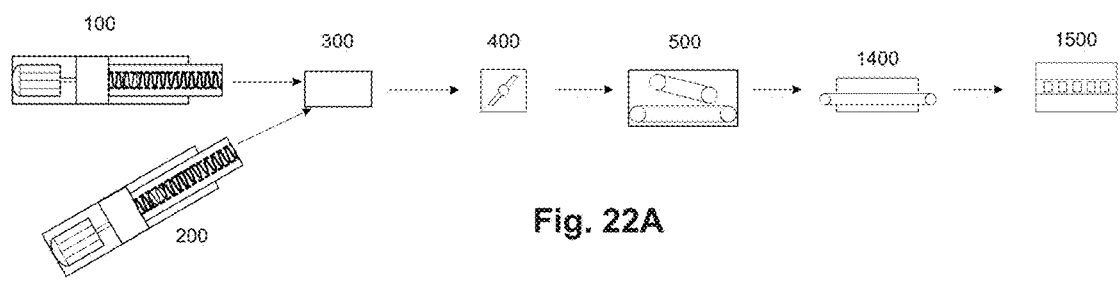
FIG. 22A is a diagram of a conveyor molding process for producing animal chews from extruded materials as described herein.

Three methods for making the animal chew are illustrated in FIGS. 20-22.

Each of the three methods involves forming a melt using one or more extruders. A body extruder 100 mixes and melts the starch, protein, and water ingredients of the chewable matrix, together with any other components desired for inclusion in the chewable matrix. Substantially any extrusion apparatus capable of sufficient heating and mixing to produce a substantially homogenous melt at a temperature in excess of the gelatinization temperature of at least most of the starch in the mixture can be used, such as commercially available twin-screw cooker-extruder. Selection of an appropriate extruder is within the ken of an ordinary artisan in this field, in view of the desired processing capacity of the apparatus and temperature of the extrudate.

If desired, a second extruder, herein designated a filling extruder 200 for illustrative purpose, can be used to provide a second melt that can be coextruded with the first melt obtained from the body extruder 100. The first and second melts can be used to generate animal chews having a body with a filling in a cavity or hollow thereof to form a body comprising multiple chewable matrices (see, e.g., FIG. 23B), or a combination of these. Additional extruders can also be used to provide yet more melts which can be combined with the first and second melts, if desired.

The melts from body and filler extruders 100 and 200 (if present) are combined and processed further in the three processes illustrated in FIGS. 20-22.

FIG. 20 illustrates a compression molding process for making the chews described herein. Compression molding is commonly used Dora variety of rubbers and thermosetting plastics, but the process described herein differs substantially. Compression molding techniques used for rubber and plastic involve filling a mold with a resin or particulate matter and heating the mold under pressure to heat and set the resin or plastic. Compression molding techniques tend not to be used for consumable foods or animal products for a variety of reasons, such as the unsuitability of the components of most such products for such processing, the substantial irreversibility of the process, and incompatibility of desired product shapes with such processing. The compression molding process illustrated in FIG. 20 is amenable to continuous and semi-continuous production of molded articles, such as the animal chew described herein.

The animal chews described herein have a composition that is well-suited to compression molding. The chews are made using materials that are molten or resemble molten plastic materials. The chews are formed while their material is in its molten or molten-like state. It is desirable that the chews attain an irreversible shape upon molding. The chews have shapes (e.g., complex surfaces, such as the closely-spaced raised nubs and an overall 'twisted' conformation) that are amenable to molding under pressure, and which are preferably formed by molding under pressure. Because the chews described herein can be made from a molten, plastic extrudate, it can be unnecessary to heat the molds in which the extrudate is compressed (unlike many known compression molding processes). Thus, even though compression molding process are known in a general sense, their application to making pet chew products is believed to be uncommon or even unprecedented, especially for the formulations described herein.

FIG. 20 illustrates a process involving formation of individual billets of melt, followed by shaping of the billets within a two-piece mold. Combined melt obtained from body and Idler extruders 100 and 200 is fed to a portioning manifold 1100, which portions the melt into individual billets, each of which is ultimately used to form a single animal chew. The billets are warmed sufficiently (generally at the time they exit the extruder) that they have a moldable, plastic texture suitable for forming in a compression mold. The billets are kept in a warm, plastic state at least until they are molded. Extrudate retains substantial heat as it emerges from an extruder, and transport and manipulation of extrudate delivery to and processing by a portioning manifold) can often be achieved without substantial diminishment of its moldability. Of course, supplemental heating can be performed to 'boost' the moldability an extrudate portion if desired.

An individual billet is delivered between two mold forms, herein designated a bottom stamping former 1200 and a top stamping former 1300. The two mold forms define the three-dimensional shape of a desired animal chew (such as one of the chews described herein) when they are compressed together. The plates are so compressed with the stilt-plastic billet interposed between them within the matching molding cavities of the two plates. An example of one of the two mold forms is shown in FIG. 20B, with a molded billet present in the molding cavity thereof; a matching mold form is visible in the background. Once formed, the billet is cooled to a temperature at which it retains its form. Thereafter, the formed billet is transferred to an oven dryer 900 to reduce its moisture content to a desired love, and thence to a tumbler 1000 in which the formed billet is tumbled with other formed billets or other materials to remove excess material or flashing resulting from overfill of the molding cavities beyond its capacity. Tumbled formed billets are further cooled in a cooler 1400 to reduce their temperature before they are transferred to a packager 1500 which seals the thus-formed animal chew in a package to inhibit further loss of moisture from the animal chew.

The bottom and top stamping formers 1200 and 1300 can, for example, be corresponding parts of a compression molding system of the type that is commonly used in the plastics industry to form plastic bottle caps. In a device of this type, billets of melt generated by the portioning manifold 1100 are delivered to a rotating table having stations which bear individual bottom forming plates. Filling the bottom forming plate takes place at one station, followed by compression of the billet at one or more different stations along the rotation table. Joining of a bottom and top forming plates compresses the billet into a shape described herein.

An embodiment of an apparatus suitable for the portioning and molding operations of the compression molding process illustrated in FIG. 20 is shown in FIGS. 20C and 20D. FIG. 20C is top view of the apparatus, and FIG. 20D is side view showing some aspects of it. This apparatus can take the place of the portioning manifold 1100, the top stamping former 1300, and the bottom stamping former 1200 in FIG. 20A.

In FIG. 20C, two intermeshing rotary devices are shown, each having plates linked about the periphery of a rotating hub. The rotary device on the left (rotating clockwise in this view) is a portioner 1150 (akin to portioning manifold 1100 in FIG. 20A) that is adapted to work with the rotary device on the right (rotating counter-clockwise in this view), which is a rotary molder 1250 (combining the functionality of the bottom- and top-stamping formers 1200 and 1300 in FIG. 20A). A conveyor 1290 carries formed pet chews 1 to the right, away from the rotary molder 1250 in FIG. 20C.

In the FIG. 20C, the portioner 1150 is depicted having eight portioner plates 1170 equally spaced about the periphery of a hub 1160 that rotates about a shaft 1180. Each portioner plate 1170 bears a void 1175 (not shown in FIG. 20C) that extends completely through the portioner plate 1170, has a controlled volume (i.e., that of the desired charge to be contained within the void 1175), and a shape that approximates the outline of the lower molding cavities 1282 of the lower mold plates 1280 of the rotary molder 1250. Advantageously, the portioner plates can be changed to change the billet volume described herein. The portioner 1150 rotates each portioner plate 1170 past the extrudate feed line 110 to facilitate filling of the plate's void with extrudate. Filling occurs in the void of the portioner plate at the "12 o'clock" position of the portioner 1150 in FIG. 20C. The void 1175 is filled with extrudate delivered by the extrudate feed line 110, and the bolus of extrudate with which the void is filled is termed the "charge."

After the void 1175 in the portioner plate 1170 is filled, the portioner hub 1160 rotates until the portioner plate 1170 is aligned (at the "3 o'clock" position of the portioner 1150 in FIG. 20C) between upper mold plate 1270 and lower mold plate 1280 (visible in FIG. 20D) of the rotary molder 1250. The charge is there expelled from the void into the lower plate of the molder. Such expulsion can occur under gravity, or the charge can be urged out of the void 1175 by a knock-out device 1195 such as a pneumatic piston or a metal strip resiliently opposed against the upper face of the portioner plate 1170 and aligned with void 1175. The charge is sufficiently ductile at this point that it can be molded by the rotary molder 1250.

Upon expulsion into the lower molding cavity 1282 of the lower mold plate 1282 (at the "9 o'clock" position of the rotary molder 1250 in FIG. 20C), the charge initially has a shape that does not completely fill the lower molding cavity 1282, but is contained within it. The upper mold plate 1270 does not contact the charge or the lower mold plate 1280 at this position.

Portioner 1150 is illustrated in FIGS. 20C and 20D as a rotating disk-shaped hub 1160 having discrete portioner plates 1170 mounted about its circumference. These two elements can be combined, for example in the form of a larger disk-shaped hub 1160 which has no attached portioner plates 1170, but which bears within the hub 1160 the voids 1175 in the same relative positions about the shaft 1180 of the portioner 1150 as shown in FIGS. 20C and 20D. FIG. 20C includes a few informalities, in that the upper mold plates 1270 in approximately the "8 o'clock," "9 o'clock," and "10 o'clock" positions of the rotary molder 1250 ought to obscure the three corresponding portioner plates 1170 and all or a portion of the voids 1175 extending therethrough (since the portioner plates 1170 are interposed between the upper mold plates 1270 and the lower mold plates 1280, which are obscured by the upper mold plates in FIG. 20C). Furthermore, upper mold plates 1270 should obscure portions of the conveyor 1290, but are treated as transparent for this purpose in FIG. 20C. In FIG. 20D, shafts 1264 and 1180 are shown crossing multiple components (e.g., drive wheels 1162 and 1262, bottom plate 1192, hub 1260, and a pair of upper and lower mold plates, even though the shaft would normally be obscured by those items (i.e., those items are treated as transparent for this purpose in FIG. 20D). Similarly, the edges of hub 1260 are shown crossing several mold plates, even though those edges would normally be obscured by the plates (i.e., the plates are treated as transparent for this purpose in FIG. 20D). Not shown in FIG. 20D for the purpose of illustration are hub 1160, connections between mold plates and hub 1260, mold plates on the 'upper' half of rotary molder 1250 in FIG. 20C, and mechanisms for moving, inclining, and declining mold plates.

As the lower mold plate 1280 is rotated in a horizontal plane (from the "9 o'clock" to about the "6 o'clock" position of the rotary molder 1250 in FIG. 20C, the rotary molder 1250 urges the upper mold plate 1270 downwardly until it contacts the lower mold plate 1280. Downward motion of upper plate 1270 is imparted by a mechanism within the hub 1260, connected by upper plate connector 1274. Prior to the upper and lower mold plates 1270 and 1280 contacting one another, the upper molding cavity 1272 in the upper mold plate 1270 contacts the still-ductile charge; further lowering of the upper mold plate 1270 compresses the charge within and between the upper and lower molding cavities 1272 and 1282, causing the charge to fill the cavities completely. Any excess charge (i.e., beyond the volume defined by the closed molding cavities) can be expelled at the seam between the upper and lower mold plates 1270 and 1280 and form a flash that can be removed (e.g., in tumbler 1000 in FIG. 20A). Upon contact of the upper and lower mold plates 1270 and 1280, the upper and tower molding cavities 1272 and 1282 are in their most-closely-opposed conformation, and they are held in this conformation momentarily as the hub 1260 of the rotary molder 1250 continues to rotate. The upper and tower mold plates 1270 and 1280 can be cooled (e.g., by a gas or liquid contacting the plates) before the plates are separated from one another. Such cooling can stiffen the now-shaped charge and contribute to its conformational stability upon de-molding.

Beginning at about the "3 o'clock" position of the rotary molder 1250 in FIG. 20C, the upper mold plate 1270 is lifted away from the lower mold plate 1280, separating the upper and tower molding cavities 1272 and 1280. The now-shaped charge can rest in or adhere to one or the other of the upper mold plates 1270 and 1280, and will usually rest in the lower mold plate 1280 unless it adheres to the upper mold plate 1270. The upper mold plate 1270 appears to get smaller between the "3 o'clock" and the "12 o'clock" position of the rotary molder 1250 in FIG. 20C because the distal ends of the upper and lower mold plates 1270 and 1280 are being inclined outwardly away from one another (i.e., they are being opened apart outwardly and perpendicularly to the horizontal plane, like a clam shell anchored at its hinge to the hub 1260). This inclination/opening continues until both the upper and lower mold plates 1270 and 1280 are vertical at the "12 o'clock" position in FIG. 20C. In this configuration, the formed charge (which is sufficiently rigid to hold its molded shape) tumbles out of the molding cavity in which it is lodged onto the conveyor 1290 in the shape of a pet chew 1. In the event the charge adheres to the molding cavity in which it is lodged, it can be dislodged pneumatically or mechanically, using any known device or method known in the molding arts, Advantageously, the mold plates can be replaced as they wear or when a different size or shape of pet chew is desired.

After shaped charges are discharged from the rotary molder 1240 (at the "12 o'clock" position in FIG. 20C), the upper and tower mold plates 1270 and 1280 are declined back into the horizontal position (at about the "10 o'clock" position of the rotary molder 1250 in FIG. 20C) to align them for having another charge deposited therebetween by the portioner 1150. The upper and lower mold plates 1270 and 1280 can be cleaned or lubricated (e.g., sprayed with an edible oil) between dislodgement of one formed charge and deposition therebetween of a fresh charge from the portioner 1150. Such cleaning and lubrication can facilitate dislodgement of formed charges and maintain cleanliness of the upper and lower molding cavities 1272 and 1282.

FIG. 20D illustrates a side view of the same apparatus shown in FIG. 20C. The apparatus rests upon a floor F and is supported, for example, by several legs 1052, the precise arrangement of which is not critical. The components of the apparatus can be contained within a housing 1050. The apparatus can include a variety of supports, material inlets and outlets, and power, heat, or coolant inlets and outlets to facilitate its operation. The housing can serve to prevent environmental contamination (e.g., by dust or grime) of the pet chew product and its precursors, can protect operators against hazards such as heat, electricity, and mechanical movement of the apparatus components. The housing can be openable or removable to permit access to the components of the apparatus and materials passing therethrough. The precise arrangement of housing, support, and access components is not critical.

In FIG. 20D, two thin, horizontally-oriented rectangles, each opposed against the other at one end represent an edge-on view of a pair of rotary drive mechanisms. Portioner drive wheel 1162 drives rotation of the portioner 1150. Rotary molder drive wheel 1262 drives rotation of the rotary molder 1250. Rotations of the portioner 1150 and the rotary molder 1250 are coordinated, so pardoner plate voids 1175 are aligned with lower molding cavities 1282 during discharge of charges from the voids into the cavities. Such coordination facilitates proper insertion of charge into the molding cavities, complete filling of the cavities with charge, and minimization of wasted charge. Coordination of the portioner and rotary molder drive wheels 1162 and 1262 can be achieved by any known method such as direct perimeter-to-perimeter contact (as shown in FIG. 20D), by interlocking circumferential gears, by coordinated drive belts, by a chain drive, by coordinated motors, or by separate control of each of the two wheels.

A shaft 1180 extends between the portioner drive wheel 1162 and the hub 1160 to which the portioner plates 1170 are circumferentially attached. By means of this shaft 1180, torsional power applied to the portioner drive wheel 1162 is transmitted to the hub 1160 and the portioner plates 1170, resulting in their rotation. Similarly, a shaft 1264 extends between the rotary molder drive wheel 1262 and the hub 1260 to which upper mold plates 1270 and lower mold plates 1280 are attached. Torsional power applied to the rotary molder drive wheel 1262 will drive rotation of the hub 1260 and the upper and lower mold plates 1270 and 1280. By use of conventional mechanical components (e.g., cams, bearings, raceways, and mechanical deflectors) torsional power applied to the shaft 1264 can also be used to drive movement of upper and lower mold plates 1270 and 1280 toward and away from one another, inclination and declination of the upper and lower mold plates 1270 and 1280, and mechanical shaking or rattling of the plates to dislodge formed charges therefrom.

In the portioner 1150, three plates are shown (edge-on) aligned with the extrudate feed line 110 in FIG. 20D. The top plate 1191 and the bottom plate 1192 are fixed in location relative to the extrudate feed line 110. The top plate 1191 and extrudate feed line 110 are not shown in FIG. 20C. A portioner plate 1175 is shown in FIG. 20D interposed between the top plate 1191 and the bottom plate 1192. That portioner plate 1170 is present at the "12 o'clock" position of the portioner 1150 shown in FIG. 20C. The void 1175 in that portioner plate 1170 is aligned with the extruder feed line 110 closely opposed against the top plate 1191 and the bottom plate 1192. The bottom plate 1192 completely obscures the void 1175 at its opposed face. The top plate 1191 has an orifice (not shown in the figures) extending through which extrudate can pass from the extrudate feed line 110 into the void 1175. The top plate 1191 also obscures the void 1175 as the it rotates out of alignment with the orifice, thereby completely closing off the void 1175 between the top plate 1191 and the bottom plate 1192, defining a fixed volume for the charge. That fixed volume can be selected by varying the thickness of the portioner plate 1170 (and the corresponding separation of the top and bottom plates 1191 and 1192) and the shape and dimensions of the void 1175.

As the filled portioner plate 1170 and the void 1175 carrying the charge moves to the right in FIG. 20D (corresponding to rotation of the plate 1170 to the "3 o'clock" position of the portioner 1150 in FIG. 20C), a knock-out device 1195 causes the charge to be expelled from the void 1175 in the portioner plate 1170 into the lower molding cavity 1282.

In FIG. 20D, descent of the upper mold plate 1270 toward and against the lower mold plate 1280 can be seen for the mold plate pairs moving left-to-right in the figure (i.e., the mold plates shown in the lower half of FIG. 20C—the mold plates in the upper half of FIG. 20C are not shown in FIG. 20D). Also visible between the mold plates in FIG. 20D is the charge, which does not have the shape of the upper molding cavity 1272 until the upper and lower mold plates 1270 and 1280 are urged against each other.

The compression molding process described herein and the apparatus illustrated in FIGS. 20C and 20D can be used to make other products in addition to the animal chews described herein. By way of example, they can be used in manufacture of biscuits and confections intended for human consumption, or for other products having a shape and composition suitable for compression molding.

A significant advantage of this compression molding process is that the 'twisted' conformation of the shaft of the animal chew (see, e.g., FIG. 10) can be imparted to the chew without performing a physical twisting operation upon the chew. Instead, the 'twisted' conformation can be made through a simple molding process. In such a molding process, one lateral edge 83 of a condyle 82 of a bone-shaped chew is set substantially deeper into a molding plate than the opposite lateral edge 84 of the same condyle 82. Even though the material that fills the mold is not necessarily physically twisted, the condyle 82 nonetheless attains a 'twisted' conformation upon molding, as can be seen from the parting line 42 (which forms at the edge at which the two molding cavities used to form a chew, for example, the chew shown in FIG. 10, meet).

FIG. 21 illustrates a process involving simultaneous molding and cutting of melt to form intermediate bodies which are thereafter subjected to further shaping prior to cooling to yield the animal chew. In this process, combined melt obtained from body and filler extruders 100 and 200 is fed to a coextrusion head 600 to form a continuous rope-like melt. The melt rope is fed under pressure into matched molding cavities of a die roll molder 700 (side and end-on views of a nozzle used to feed the melt rope between the rollers of the die roll molder are shown in FIGS. 21B and 21C) to yield intermediate bodies severed from the melt rope, the intermediate bodies having a shape conferred upon them by the die roll molder 700. The intermediate bodies, which remain at a sufficiently high temperature that they remain plastic, are fed into a forming system (800) which manipulates the intermediate bodies (e.g., by twisting or bending them) to further shape them into the final desired shape of the animal chew. Formed bodies are passed into an oven dryer 900 to reduce their moisture content and thence to a tumbler 1000, cooler 1400, and packaging system 1500 as described above.

FIG. 22 illustrates a process involving formation of cutting intermediate bodies from an extruded melt having a perimeter shape that is approximately that of the desired perimeter shape of the final animal chew, followed by passage of the intermediate bodies through a forming system 500 that confers additional shape features to the intermediate bodies prior to cooling them to form the final animal chew. In this process, extruded melted is delivered to a die manifold which shapes the melt into a rope-like mass having a perimeter shape that is approximately that of the desired perimeter shape of the final animal chew. The rope-like mass is delivered to a cutter 400 that divides the rope into slices cut approximately perpendicular to the long axis of the rope. The slices are delivered to a forming conveyor 500 which confers shape features to the slice faces bounded by the rope perimeter. As shown in FIGS. 22B and 22C illustrate the construction of the forming conveyor, including convex shaping members 510 (further illustrated in FIGS. 22Ci and 22Cii) and concave shaping members 520 between which the slices are compressed to confer shape thereto. The spacing between the convex and concave shaping members 510 and 520, which are attached to separate opposed conveyers can be adjusted to varying the imprint resolution imparted to the formed slices. After being shaped in the forming conveyor 500, the formed slices are transferred to a cooler 1400 and thence to a packager 1500.

EXAMPLES

The subject matter of this disclosure is now described with reference to the following Examples. These Examples are provided for the purpose of illustration only, and the subject matter is not limited to these Examples, but rather encompasses all variations which are evident as a result of the teaching provided herein.

Example 1

Table 1 lists illustrative recipe ranges for some embodiments of the animal chew described herein. Also listed are more specific formulas for two particular embodiments, designated "Harder Recipe 1" and "Softer Recipe 1" formulations, Components are listed as percentage by weight of the melt, prior to heating, rather than by weight percentage in the chewable matrix formed from the melt (as disclosed elsewhere in this disclosure), Note that the amount of water, including humectants, can be substantially greater than the final water content of the chewable matrix of the animal chew. This difference is attributable to

TABLE 1

| Components Combined to Form Melt | General Proportion (wt %) | Harder Recipe 1 (wt %) | Softer Recipe 1 (wt %) |
|---|---|---|---|
| Proteins | 5-20 | 9 | 11 |
| Starches | 30-60 | 51 | 48 |
| Abrasive Fibers and or Particles | 3-9 | 7 | 7 |
| Flavor and Aroma Enhancers | 0-6 | 3 | 2 |
| Water (optionally including one or more humectants) | 24-30 | 25 | 26 |
| Other ingredients (e.g., Preservatives, Minerals, Vitamins, Colorants, Flavorants, Aromants, Fillers) | 3-7 | 5 | 6 |
| Total | | 100 | 100 |

A variety of different matrix formulations were formed with varying proportions of CRISP FILM and ELASTIGEL starches, brewer's rice, and powdered cellulose. The effects of these proportions on setting time (results shown in FIGS. 19A and 19C), hardness (results shown in FIG. 19B), and moisture retention (results shown in FIG. 19D) were determined.

Example 2

Another exemplary formula for the components that are combined to form a melt as described herein is shown in Table 2. As in Example 1, proportions shown are weight of each ingredient as a percentage of the weight of the combination. The water content of this combination is greater than the final water content of animal chews formed from the melt prepared from the combination, owing to water loss from the composition during melt formation and subsequent controlled drying of the formed animal chew.

In each of Table 2A, 2B, and 2C, STTP is sodium tri polyphosphate, Each of CRISPF and ELASTIGEL is a trademark of Corn Products Development

TABLE 2A

Melt Ingredients.

Proportion of Ingredient(s), wt % of total formula Formula Name

| Ingredient(s) | A | B | C | D | E | F |
|---|---|---|---|---|---|---|
| Ground Brewers Rice | 38.7 | 45.5 | 40.6 | 49.6 | 36.3 | 47.1 |
| Water | 23.1 | 23.1 | 23.1 | 23.1 | 23.1 | 23.1 |
| Chicken by-product meal | 8.39 | 8.39 | 8.39 | 8.39 | 8.39 | 8.39 |
| CRISPFILM Brand Modified Food Starch | 7.51 | 0.00 | 8.00 | 0.80 | 2.85 | 0.00 |
| ELASTIGEL Brand Modified Food Starch | 1.88 | 4.80 | 3.36 | 3.97 | 8.00 | 8.00 |
| Cellulose Powder | 7.04 | 4.80 | 3.20 | 0.80 | 8.00 | 0.00 |
| Propylene Glycol | 5.02 | 5.02 | 5.02 | 5.02 | 5.02 | 5.02 |
| Powdered Gypsum | 2.11 | 2.11 | 2.11 | 2.11 | 2.11 | 2.11 |
| Bone Phosphate | 2.11 | 2.11 | 2.11 | 2.11 | 2.11 | 2.11 |
| Flavorants, Aromants, and Colorants | 2.16 | 2.16 | 2.16 | 2.16 | 2.16 | 2.16 |
| STPP | 1.00 | 1.00 | 1.00 | 1.00 | 1.00 | 1.00 |
| Vitamins and Minerals | 0.106 | 0.106 | 0.106 | 0.106 | 0.106 | 0.106 |
| Preservative(s) | 0.906 | 0.906 | 0.906 | 0.906 | 0.906 | 0.906 |
| Approximate Starch Content, wt % | 38.7 | 39.8 | 41.8 | 43.0 | 37.9 | 43.8 |

TABLE 2B

Melt Ingredients.

Proportion of Ingredient(s), wt % of total formula Formula Name

| Ingredient(s) | G | H | I | J | K | L |
|---|---|---|---|---|---|---|
| Ground Brewers Rice | 47.1 | 36.3 | 36.3 | 45.6 | 47.1 | 40.6 |
| Water | 23.1 | 23.1 | 23.1 | 23.1 | 23.1 | 23.1 |
| Chicken by-product meal | 8.39 | 8.39 | 8.39 | 8.39 | 8.39 | 8.39 |
| CRISPFILM Brand Modified Food Starch | 0.00 | 8.00 | 8.00 | 4.76 | 8.00 | 4.32 |
| ELASTIGEL Brand Modified Food Starch | 0.00 | 8.00 | 2.84 | 0.00 | 0.00 | 4.32 |
| Cellulose Powder | 8.00 | 2.80 | 8.00 | 4.76 | 0.00 | 5.88 |
| Propylene Glycol | 5.02 | 5.02 | 5.02 | 5.02 | 5.02 | 5.02 |
| Powdered Gypsum | 2.11 | 2.11 | 2.11 | 2.11 | 2.11 | 2.11 |
| Bone Phosphate | 2.11 | 2.11 | 2.11 | 2.11 | 2.11 | 2.11 |
| Flavorants, Aromants, and Colorants | 2.16 | 2.16 | 2.16 | 2.16 | 2.16 | 2.16 |
| STPP | 1.00 | 1.00 | 1.000 | 1.000 | 1.000 | 1.000 |
| Vitamins and Minerals | 0.106 | 0.106 | 0.106 | 0.106 | 0.106 | 0.106 |
| Preservative(s) | 0.906 | 0.906 | 0.906 | 0.906 | 0.906 | 0.906 |
| Approximate Starch Content, wt % | 37.0 | 42.5 | 38.0 | 40.0 | 44.1 | 39.4 |

TABLE 2C

Melt Ingredients.

Proportion of Ingredient(s), wt % of total formula Formula Name

| Ingredient(s) | M | N | O | P | Q |
|---|---|---|---|---|---|
| Ground Brewers Rice | 45.6 | 40.6 | 55.1 | 31.1 | 33.7 |
| Water | 23.1 | 23.1 | 23.1 | 23.1 | 23.1 |
| Chicken by-product meal | 8.39 | 8.39 | 8.39 | 8.39 | 8.39 |
| CRISPFILM Brand Modified Food Starch | 4.76 | 3.32 | 0.00 | 8.00 | 7.51 |
| ELASTIGEL Brand Modified Food Starch | 4.80 | 8.00 | 0.00 | 8.00 | 1.88 |
| Cellulose Powder | 0.00 | 3.24 | 0.00 | 8.00 | 7.04 |
| Propylene Glycol | 5.02 | 5.02 | 5.02 | 5.02 | 5.02 |
| Supplement (see notes) | — | — | — | — | 5.00 |
| Powdered Gypsum | 2.11 | 2.11 | 2.11 | 2.11 | 2.11 |
| Bone Phosphate | 2.11 | 2.11 | 2.11 | 2.11 | 2.11 |
| Flavorants, Aromants, and Colorants | 2.16 | 2.16 | 2.16 | 2.16 | 2.16 |
| STPP | 1.000 | 1.000 | 1.000 | 1.000 | 1.00 |
| Vitamins and Minerals | 0.106 | 0.106 | 0.106 | 0.106 | 0.106 |
| Preservative(s) | 0.906 | 0.906 | 0.906 | 0.906 | 0.906 |
| Approximate Starch Content, wt % | 44.1 | 41.7 | 43.2 | 38.4 | 38.7-43.7 |

Note:
In Table 2C, the ingredient identified as "Supplement" can be any of a gelatin, a gluten (e.g., wheat or gluten), a casein (e.g., sodium or calcium caseinate), dextrose, a dextrin, protein isolates (e.g., wheat protein isolate), and protein-containing vegetable extracts (e.g., soy concentrates).

TABLE 3

List of Part Numbers and Abbreviations in FIGS.

| | |
|---|---|
| 1 | Pet Chew |
| 10 | Body |
| 12 | Nub |
| 14 | Ridge |
| 16 | Bulge |
| 17 | Topographical Characters |
| 18 | Visible inclusions |
| 20 | First Surface |
| 22 | First Portion of Body |
| 30 | Second Surface |
| 32 | Second Portion of Body |
| 40 | Transitional Surface |
| 42 | Parting Line |
| 44 | Chamfer |
| 50 | Cavity (within or through Body) |
| 52 | Intermediate Portion |
| 55 | Filling (within Cavity) |
| 60 | Interior of Body |
| 70 | Shaft |
| 80 | End (of Pet Chew) |
| 82 | Condyle |
| 83 | One Lateral Edge |
| 84 | Other Lateral Edge |
| 90 | Sheath |

TABLE 3-continued

List of Part Numbers and Abbreviations in FIGS.

| | |
|---|---|
| 100 | Body Extruder |
| 110 | Extrudate Feed Line |
| 200 | Filling Extruder |
| 300 | Die Manifold |
| 400 | Cutter |
| 500 | Forming Conveyor |
| 510 | convex shaping member |
| 520 | concave shaping member |
| 600 | Coextrusion Head |
| 700 | Die Roll Molder |
| 800 | Forming System |
| 900 | Oven Dryer |
| 1000 | Tumbler |
| 1050 | Housing |
| 1052 | Legs |
| 1100 | Portioning Manifold |
| 1150 | Portioner |
| 1160 | Hub |
| 1162 | Drive Wheel |
| 1170 | Portioner Plate |
| 1175 | Void |
| 1180 | Shaft |
| 1191 | Top Plate |
| 1192 | Bottom Plate |
| 1195 | Knock-Out Device |
| 1200 | Bottom Stamping Former |
| 1250 | Rotary Molder |
| 1260 | Hub |
| 1262 | Drive Wheel |
| 1264 | Shaft |
| 1270 | Upper Mold Plate |
| 1272 | Upper Molding Cavity |
| 1274 | Upper Plate Connector |
| 1280 | Lower Mold Plate |
| 1282 | Lower Molding Cavity |
| 1290 | Conveyor |
| 1300 | Top Stamping Former |
| 1400 | Cooler |
| 1500 | Packager |
| R | Radius of Shaft curvature |
| F | Floor |

The disclosure of every patent, patent application, and publication cited herein is hereby incorporated herein by reference in its entirety.

While this subject matter has been disclosed with reference to specific embodiments, it is apparent that other embodiments and variations can be devised by others skilled in the art without departing from the true spirit and scope of the subject matter described herein. The appended claims include all such embodiments and equivalent variations.

What is claimed is:

1. An animal chew having a consumable portion, the consumable portion comprising a chewable matrix and having dimensions selected to fit within the oral cavity of the animal, wherein the chewable matrix comprises:
   i) about 9-17 wt % protein,
   ii) about 30-40 wt % starch, said starch providing from 10 to about 20% amylose by weight of said chewable matrix,
   iii) water and, optionally, a humectant, in amounts sufficient to confer chewable plasticity to the chewable matrix, and
   iv) a temporally efficacious amount of an orally active ingredient.

2. The chew of claim 1, wherein at least about 50 wt % of the starch in the chewable matrix is gelatinized.

3. The chew of claim 2, wherein at least about 80 wt % of the starch in the chewable matrix is gelatinized.

4. The chew of claim 1, wherein the chewable matrix comprises a humectant.

5. The chew of claim 4, wherein the humectant is selected from the group consisting of glycerol, propylene glycol, and a combination of these, and is present in an amount that is about 4-12 wt % of the chewable matrix.

6. The chew of claim 1, wherein the chewable matrix further comprises one or more additional ingredients selected from the group consisting of vitamins, minerals, flavorants, aromants, colorants, and preservatives.

7. The chew of claim 1, wherein the orally active ingredient is selected from the group consisting of dental prophylactic ingredients, breath agents, pharmaceutical agents, and combinations of these.

8. The chew of claim 1, wherein the orally active ingredient is a dental prophylactic ingredient.

9. The chew of claim 8, wherein the dental prophylactic ingredient is an abrasive.

10. The chew of claim 9, wherein the chewable matrix comprises 2-10 wt % of at least one abrasive.

11. The chew of claim 9, wherein the abrasive is fibrous.

12. The chew of claim 11, wherein the chewable matrix comprises 5-7 wt % of the fibrous abrasive.

13. The chew of claim 11, wherein the fibrous abrasive is a cellulose.

14. The chew of claim 13, wherein the cellulose has a number-average fiber length not greater than about 500 micrometers.

15. The chew of claim 13, wherein the cellulose is substantially uniformly dispersed in the chewable matrix.

16. The chew of claim 8, wherein the dental prophylactic ingredient is an anti-tartar agent.

17. The chew of claim 16, wherein the anti-tartar agent is a polyphosphate selected from the group consisting of sodium tripolyphosphate, tetrasodium pyrophosphate, sodium hexametaphosphate, and combinations of these.

18. The chew of claim 1, wherein the orally active ingredient is a breath agent.

19. The chew of claim 18, wherein the orally active ingredient is selected from the group consisting of plants, plant extracts, bicarbonate salts, and combinations of these.

20. The chew of claim 1, having a 'bone-shaped' conformation including an elongate shaft interposed between two flattened bi-lobed ends.

21. The chew of claim 20, wherein the flattened ends are rotationally offset from one another about the axis of the shaft.

22. The chew of claim 1, wherein the consumable portion has a plurality of nubs extending outwardly therefrom, the nubs having dimensions compatible with being interposed between teeth of the animal when the animal grasps the chew in its mouth.

23. The chew of claim 1, wherein the chewable matrix exhibits sufficient integrity that a substantial portion of the consumable portion of the chew will remain non-consumed by the animal after at least one minute of composite chewing time.

24. A method for cleaning the teeth of an animal, the method comprising providing to the animal the chew of claim 1, and inducing the animal to chew thereupon, the chewable matrix of the chew comprising at least one ingredient that renders the chew appetizing to the animal, the ingredient selected from the group consisting of a flavorant, an aromant, and combinations of these.

25. The chew of claim 1, wherein the chewable matrix exhibits sufficient friability that all of the consumable portion of the chew can be consumed by the animal in not more than four hours of composite chewing time.

26. The chew of claim 1, wherein the chewable matrix exhibits sufficient friability that all of the consumable portion of the chew can be consumed by the animal in not more than 2 hours of composite chewing time.

27. The chew of claim 1, wherein the chewable matrix exhibits sufficient friability that all of the consumable portion of the chew can be consumed by the animal from about 30 seconds to no more than four hours of composite chewing time.

28. The chew of claim 1, wherein the chewable matrix exhibits sufficient friability that all of the consumable portion of the chew can be consumed by the animal from about 30 seconds to no more than two hours of composite chewing time.

29. The chew of claim 1, wherein the texture and shape of the chewable matrix and the content of the orally active ingredient in the chew are sufficient to limit plaque accumulation on the teeth of an animal that is provided one chew every day at least about as much as brushing the animal's teeth using a veterinary dentifrice every other day.

30. The chew of claim 1, wherein the texture and shape of the chewable matrix and the content of the orally active ingredient in the chew are sufficient to limit tartar accumulation on the teeth of an animal that is provided one chew every day at least about as much as brushing the animal's teeth using a veterinary dentifrice every other day.

31. The chew of claim 1, wherein the texture and shape of the chewable matrix and the content of the orally active ingredient in the chew are sufficient to limit the extent of gingivitis in an animal that is provided one chew every other day at least about as much as brushing the animal's teeth using a veterinary dentifrice every other day.

32. The chew of claim 1, wherein the texture and shape of the chewable matrix and the content of the orally active ingredient in the chew are sufficient to limit the incidence of halitosis in an animal that is provided one chew every day at least about as much as brushing the animal's teeth using a veterinary dentifrice every other day.

33. The chew of claim 1, wherein the chewable matrix exhibits sufficient rigidity that the chewable matrix does not fracture until it has been chewed at least about 10 times by the animal.

34. The chew of claim 1, wherein the chewable matrix exhibits sufficient rigidity that the chewable matrix does not fracture until it has been chewed at least about 25 times by the animal.

35. The chew of claim 1, wherein the chewable matrix exhibits sufficient integrity that a substantial portion of the consumable portion of the chew will remain non-consumed by the animal after at least 30 seconds of composite chewing time.

36. The chew of claim 1, wherein the chewable matrix exhibits sufficient ductility that the animal is able to leave a visible indentation in the surface of the chewable matrix upon biting the chew one time.

* * * * *